(12) United States Patent
Lashinski et al.

(10) Patent No.: US 12,303,116 B2
(45) Date of Patent: May 20, 2025

(54) DEVICES, SYSTEMS, AND METHODS FOR OCCLUDING CAVITIES WITHIN THE BODY

(71) Applicant: Laminar, Inc., Santa Rosa, CA (US)

(72) Inventors: Randall T. Lashinski, Windsor, CA (US); Joshua J. Dwork, Santa Rosa, CA (US)

(73) Assignee: Laminar, Inc., Santa Rosa, CA (US)

( * ) Notice: Subject to any disclaimer, the term of this patent is extended or adjusted under 35 U.S.C. 154(b) by 394 days.

(21) Appl. No.: 17/208,435

(22) Filed: Mar. 22, 2021

(65) Prior Publication Data

US 2021/0298728 A1 Sep. 30, 2021

Related U.S. Application Data

(60) Provisional application No. 62/994,240, filed on Mar. 24, 2020.

(51) Int. Cl.
*A61B 17/00* (2006.01)
(52) U.S. Cl.
CPC ............... *A61B 17/0057* (2013.01); *A61B 2017/00592* (2013.01); *A61B 2017/00632* (2013.01); *A61B 2017/00663* (2013.01); *A61B 2017/00668* (2013.01)
(58) Field of Classification Search
CPC ...... A61B 17/0057; A61B 2017/00592; A61B 2017/00632; A61B 2017/00663; A61B 2017/00668
See application file for complete search history.

(56) References Cited

U.S. PATENT DOCUMENTS

| | | | |
|---|---|---|---|
| 5,006,106 A | | 4/1991 | Angelchik |
| 5,810,851 A | * | 9/1998 | Yoon ................. A61B 17/064 606/139 |
| 5,919,207 A | * | 7/1999 | Taheri ............... A61B 17/0057 606/139 |
| 6,113,611 A | * | 9/2000 | Allen ................. A61B 17/068 606/151 |
| 6,290,674 B1 | | 9/2001 | Roue et al. |

(Continued)

FOREIGN PATENT DOCUMENTS

| | | |
|---|---|---|
| EP | 1441649 B1 | 8/2011 |
| EP | 3342354 A1 | 7/2018 |

(Continued)

OTHER PUBLICATIONS

U.S. Appl. No. 17/862,241, filed Jul. 11, 2022, Lashinski et al.

(Continued)

*Primary Examiner* — Alexander J Orkin
(74) *Attorney, Agent, or Firm* — Frost Brown Todd LLC

(57) ABSTRACT

Disclosed are embodiments of a device for closing or occluding a cavity or opening within a body. Some embodiments of the device can include an implant configured to be deployed within the cavity, configured to be expanded or moved against a wall portion of the cavity, and configured to twist at least a portion of the cavity when the implant is rotated. Thereafter, a securing element, staple, suture, or other fastener can be implanted in the gathered tissue to hold the tissue in the gathered state, thereby occluding the opening of the cavity. The implant can remain in the cavity or be removed.

36 Claims, 41 Drawing Sheets

(56) References Cited

U.S. PATENT DOCUMENTS

| | | | |
|---|---|---|---|
| 6,463,331 B1 | 10/2002 | Edwards | |
| 6,626,930 B1 * | 9/2003 | Allen | A61B 17/0401 |
| | | | 606/213 |
| 6,652,556 B1 | 11/2003 | VanTassel et al. | |
| 6,773,440 B2 | 8/2004 | Gannoe et al. | |
| 6,969,396 B2 | 11/2005 | Krolik et al. | |
| 7,025,756 B2 | 4/2006 | Frazier et al. | |
| 7,044,134 B2 | 5/2006 | Khairkhahan et al. | |
| 7,115,110 B2 | 10/2006 | Frazier et al. | |
| 7,122,043 B2 | 10/2006 | Greenhalgh et al. | |
| 7,128,073 B1 | 10/2006 | van der Burg et al. | |
| 7,226,458 B2 | 6/2007 | Kaplan et al. | |
| 7,320,665 B2 | 1/2008 | Vijay | |
| 7,357,815 B2 | 4/2008 | Shaoulian et al. | |
| 7,442,207 B2 | 10/2008 | Rafiee | |
| 7,559,936 B2 * | 7/2009 | Levine | A61B 17/0682 |
| | | | 606/139 |
| 7,566,336 B2 | 7/2009 | Corcoran et al. | |
| 7,645,285 B2 | 1/2010 | Cosgrove et al. | |
| 7,648,532 B2 | 1/2010 | Greenhalgh et al. | |
| 7,655,040 B2 | 2/2010 | Douk et al. | |
| 7,695,510 B2 | 4/2010 | Bloom et al. | |
| 7,713,282 B2 | 5/2010 | Frazier et al. | |
| 7,722,641 B2 | 5/2010 | van der Burg et al. | |
| 7,727,249 B2 | 6/2010 | Rahmani | |
| 7,736,392 B2 | 6/2010 | Starkebaum | |
| 7,758,639 B2 | 7/2010 | Mathis | |
| 7,780,683 B2 | 8/2010 | Roue et al. | |
| 7,828,716 B2 | 11/2010 | Burton et al. | |
| 7,984,717 B2 | 7/2011 | Tropsha et al. | |
| 8,043,329 B2 | 10/2011 | Khairkhahan et al. | |
| 8,070,671 B2 | 12/2011 | Deem et al. | |
| 8,097,015 B2 | 1/2012 | Devellian | |
| 8,197,496 B2 | 6/2012 | Roue et al. | |
| 8,236,050 B2 | 8/2012 | Bolling et al. | |
| 8,287,557 B2 | 10/2012 | To et al. | |
| 8,323,309 B2 | 12/2012 | Khairkhahan et al. | |
| 8,443,808 B2 | 5/2013 | Brensel et al. | |
| 8,512,403 B2 | 8/2013 | Navia et al. | |
| 8,523,897 B2 | 9/2013 | van der Burg et al. | |
| 8,551,161 B2 | 10/2013 | Dolan | |
| 8,603,137 B2 | 12/2013 | Voss et al. | |
| 8,690,911 B2 | 4/2014 | Miles et al. | |
| 8,758,395 B2 | 6/2014 | Kleshinski et al. | |
| 8,764,793 B2 | 7/2014 | Lee | |
| 8,771,297 B2 | 7/2014 | Miller et al. | |
| 8,777,926 B2 | 7/2014 | Chang et al. | |
| 8,784,469 B2 | 7/2014 | Kassab | |
| 8,784,482 B2 | 7/2014 | Rahdert et al. | |
| 8,840,641 B2 | 9/2014 | Miles et al. | |
| 8,845,711 B2 | 9/2014 | Miles et al. | |
| 8,851,077 B2 | 10/2014 | Brensel et al. | |
| 8,968,284 B2 | 3/2015 | Thomas et al. | |
| 9,023,080 B2 | 5/2015 | Ciobanu et al. | |
| 9,089,311 B2 | 7/2015 | Fortson et al. | |
| 9,095,363 B2 | 8/2015 | Van Bladel et al. | |
| 9,186,152 B2 | 11/2015 | Campbell et al. | |
| 9,220,487 B2 | 12/2015 | Davis et al. | |
| 9,314,249 B2 | 4/2016 | Kreidler et al. | |
| 9,326,857 B2 | 5/2016 | Carledge et al. | |
| 9,358,009 B2 | 6/2016 | Yock et al. | |
| 9,427,220 B2 | 8/2016 | Whitman et al. | |
| 9,554,804 B2 | 1/2017 | Erzberger et al. | |
| 9,572,584 B2 | 2/2017 | Miles et al. | |
| 9,592,058 B2 | 3/2017 | Erzberger et al. | |
| 9,597,086 B2 | 3/2017 | Larsen et al. | |
| 9,615,926 B2 | 4/2017 | Lashinski et al. | |
| 9,649,115 B2 | 5/2017 | Edmiston et al. | |
| 9,662,117 B2 | 5/2017 | Forsell | |
| 9,675,360 B2 | 6/2017 | Baker | |
| 9,693,780 B2 | 7/2017 | Miles et al. | |
| 9,693,781 B2 | 7/2017 | Miles et al. | |
| 9,707,124 B2 | 7/2017 | Brensel et al. | |
| 9,717,488 B2 | 8/2017 | Kassab | |
| 9,763,666 B2 | 9/2017 | Wu et al. | |
| 9,795,480 B2 | 10/2017 | Bolling et al. | |
| 9,795,481 B2 | 10/2017 | Callas et al. | |
| 9,808,253 B2 | 11/2017 | Li et al. | |
| 9,826,980 B2 | 11/2017 | Figulla et al. | |
| 9,883,864 B2 | 2/2018 | Miles et al. | |
| 9,918,719 B2 | 3/2018 | Konstantino et al. | |
| 9,937,042 B2 | 4/2018 | Cabiri et al. | |
| 9,987,017 B2 | 6/2018 | Smith et al. | |
| 10,064,628 B2 | 9/2018 | Edmiston et al. | |
| 10,071,226 B2 | 9/2018 | Hsueh et al. | |
| 10,098,640 B2 | 10/2018 | Bertolero et al. | |
| 10,143,456 B2 | 12/2018 | Javois | |
| 10,143,478 B2 | 12/2018 | Forbes | |
| 10,238,398 B2 | 3/2019 | Hughett, Sr. et al. | |
| 10,278,705 B2 | 5/2019 | Amin et al. | |
| 10,299,799 B1 | 5/2019 | DeMeritt | |
| 10,307,165 B2 | 6/2019 | Henderson et al. | |
| 10,307,620 B2 | 6/2019 | Burdette | |
| 10,386,990 B2 | 8/2019 | Shikham et al. | |
| 10,405,866 B2 | 9/2019 | Chakroborty et al. | |
| 10,420,564 B2 | 9/2019 | Miles et al. | |
| 10,433,998 B2 | 10/2019 | Keren et al. | |
| 10,441,258 B2 | 10/2019 | Corcoran et al. | |
| 10,531,878 B2 | 1/2020 | Slaughter et al. | |
| 10,537,332 B2 | 1/2020 | Edmiston et al. | |
| 10,582,929 B2 | 3/2020 | Miles et al. | |
| 10,582,930 B2 | 3/2020 | Miles et al. | |
| 10,624,648 B2 | 4/2020 | Li et al. | |
| 10,631,969 B2 | 4/2020 | Edmiston et al. | |
| 10,695,070 B2 | 6/2020 | Miles et al. | |
| 10,702,274 B2 | 7/2020 | Groothuis et al. | |
| 10,709,432 B2 | 7/2020 | Ma | |
| 10,709,454 B2 | 7/2020 | Li et al. | |
| 10,722,240 B1 | 7/2020 | Melanson et al. | |
| 10,758,241 B1 | 9/2020 | Lashinski et al. | |
| 10,898,202 B2 | 1/2021 | Slaughter et al. | |
| 11,039,822 B2 | 6/2021 | Wang et al. | |
| 11,116,510 B2 | 9/2021 | Melanson et al. | |
| 11,123,080 B2 | 9/2021 | Lashinski et al. | |
| 11,219,462 B2 | 1/2022 | Lashinski et al. | |
| 11,399,843 B2 | 8/2022 | Lashinski et al. | |
| 11,432,809 B2 | 9/2022 | Inouye et al. | |
| 11,497,505 B2 | 11/2022 | Slaughter et al. | |
| 11,540,835 B2 | 1/2023 | Groothuis et al. | |
| 11,540,836 B2 | 1/2023 | Wang et al. | |
| 11,547,417 B2 | 1/2023 | Li et al. | |
| 11,596,533 B2 | 3/2023 | Inouye et al. | |
| 2001/0005787 A1 * | 6/2001 | Oz | A61B 17/1285 |
| | | | 606/205 |
| 2003/0040771 A1 | 2/2003 | Hyodoh et al. | |
| 2003/0057156 A1 | 3/2003 | Peterson et al. | |
| 2003/0181942 A1 | 9/2003 | Sutton et al. | |
| 2003/0225420 A1 * | 12/2003 | Wardle | A61B 17/068 |
| | | | 606/151 |
| 2004/0186566 A1 * | 9/2004 | Hindrichs | A61F 2/2487 |
| | | | 623/2.37 |
| 2005/0004652 A1 | 1/2005 | van der Burg et al. | |
| 2005/0177180 A1 * | 8/2005 | Kaganov | A61B 17/0057 |
| | | | 606/151 |
| 2005/0187568 A1 * | 8/2005 | Klenk | A61B 17/0057 |
| | | | 606/153 |
| 2005/0273119 A1 * | 12/2005 | Widomski | A61B 17/0057 |
| | | | 606/151 |
| 2005/0288722 A1 | 12/2005 | Eigler et al. | |
| 2006/0287661 A1 | 12/2006 | Bolduc et al. | |
| 2007/0073337 A1 * | 3/2007 | Abbott | A61B 17/0057 |
| | | | 606/213 |
| 2007/0118213 A1 * | 5/2007 | Loulmet | A61F 2/2457 |
| | | | 606/151 |
| 2007/0198057 A1 | 8/2007 | Gelbart et al. | |
| 2008/0249566 A1 * | 10/2008 | Harris | A61F 5/0086 |
| | | | 606/220 |
| 2008/0294175 A1 | 11/2008 | Bardsley et al. | |
| 2008/0319254 A1 | 12/2008 | Nikolic et al. | |
| 2009/0171386 A1 | 7/2009 | Amplatz et al. | |
| 2009/0209986 A1 | 8/2009 | Stewart et al. | |
| 2010/0030328 A1 * | 2/2010 | Seguin | A61F 2/2466 |
| | | | 623/2.11 |

(56) References Cited

U.S. PATENT DOCUMENTS

| | | |
|---|---|---|
| 2010/0185235 A1 | 7/2010 | Kassab et al. |
| 2011/0054515 A1 | 3/2011 | Bridgeman et al. |
| 2011/0178537 A1 | 7/2011 | Whitman |
| 2012/0221042 A1 | 8/2012 | Schwartz et al. |
| 2012/0265296 A1 | 10/2012 | McNamara et al. |
| 2012/0283585 A1 | 11/2012 | Werneth et al. |
| 2012/0316584 A1 | 12/2012 | Miles et al. |
| 2013/0197570 A1 | 8/2013 | Ebata et al. |
| 2013/0338686 A1 | 12/2013 | Ruiz |
| 2014/0018841 A1 | 1/2014 | Peiffer et al. |
| 2014/0135817 A1 | 5/2014 | Tischler et al. |
| 2015/0005809 A1 | 1/2015 | Ayres et al. |
| 2015/0005810 A1 | 1/2015 | Center et al. |
| 2015/0209049 A1 | 7/2015 | Bernstein et al. |
| 2015/0342612 A1 | 12/2015 | Wu et al. |
| 2016/0058434 A1 | 3/2016 | Delaloye et al. |
| 2016/0095603 A1 | 4/2016 | McGuckin, Jr. et al. |
| 2016/0270810 A1 | 9/2016 | Vardi et al. |
| 2016/0278749 A1 | 9/2016 | Javois et al. |
| 2017/0095256 A1 | 4/2017 | Lindgren et al. |
| 2017/0202575 A1 | 7/2017 | Stanfield et al. |
| 2017/0224354 A1 | 8/2017 | Tischler et al. |
| 2017/0258475 A1 | 9/2017 | Mellmann et al. |
| 2017/0340336 A1 | 11/2017 | Osypka |
| 2018/0055496 A1 | 3/2018 | Hou et al. |
| 2018/0235640 A1 | 8/2018 | Slaughter et al. |
| 2018/0289487 A1 | 10/2018 | Alexander et al. |
| 2018/0303488 A1 | 10/2018 | Hill |
| 2018/0310925 A1 | 11/2018 | Inouye et al. |
| 2018/0310926 A1 | 11/2018 | Delaloye et al. |
| 2019/0069901 A1 | 3/2019 | Forbes |
| 2019/0083075 A1 | 3/2019 | Onushko et al. |
| 2019/0099195 A1 | 4/2019 | Carroll et al. |
| 2019/0167242 A1 | 6/2019 | Rowe et al. |
| 2019/0183512 A1 | 6/2019 | Subramaniam et al. |
| 2019/0192754 A1 | 6/2019 | Kassab et al. |
| 2019/0209179 A1 | 7/2019 | Subramaniam et al. |
| 2019/0209180 A1 | 7/2019 | Kealey et al. |
| 2019/0321176 A1 | 10/2019 | Lashinski et al. |
| 2019/0374229 A1 | 12/2019 | Anderson et al. |
| 2020/0008870 A1 | 1/2020 | Gruba et al. |
| 2020/0038004 A1 | 2/2020 | Corcoran et al. |
| 2020/0107836 A1 | 4/2020 | O'Halloran et al. |
| 2020/0107837 A1 | 4/2020 | Slaughter et al. |
| 2020/0139102 A1 | 5/2020 | Ziebol et al. |
| 2020/0155164 A1 | 5/2020 | Edmiston et al. |
| 2020/0214714 A1 | 7/2020 | Li et al. |
| 2020/0305887 A1 | 10/2020 | Lashinski et al. |
| 2021/0113212 A1 | 4/2021 | Lashinski et al. |
| 2021/0137507 A1 | 5/2021 | Keren et al. |
| 2021/0212674 A1 | 7/2021 | Wang et al. |
| 2021/0369284 A1 | 12/2021 | Lashinski et al. |
| 2022/0022854 A1 | 1/2022 | Lashinski et al. |
| 2022/0040451 A1 | 2/2022 | Urbanski et al. |
| 2022/0087741 A1 | 3/2022 | Lashinski et al. |
| 2022/0175390 A1 | 6/2022 | Lee et al. |
| 2022/0175392 A1 | 6/2022 | Jayaraman |
| 2022/0211386 A1 | 7/2022 | Amplatz et al. |
| 2022/0218356 A1 | 7/2022 | Inouye et al. |
| 2022/0240941 A1 | 8/2022 | Lashinski et al. |
| 2022/0257955 A1 | 8/2022 | Zarbatany et al. |
| 2022/0370056 A1 | 11/2022 | Inouye et al. |
| 2022/0401109 A1 | 12/2022 | Zarbatany et al. |
| 2023/0033509 A1 | 2/2023 | Lashinski et al. |
| 2023/0048873 A1 | 2/2023 | Onushko et al. |
| 2023/0084301 A1 | 3/2023 | Groff et al. |
| 2023/0130379 A1 | 4/2023 | Akpinar et al. |
| 2023/0263531 A1 | 8/2023 | Lashinski et al. |
| 2023/0310018 A1 | 10/2023 | Lashinski et al. |

FOREIGN PATENT DOCUMENTS

| | | |
|---|---|---|
| EP | 3013249 | 8/2018 |
| EP | 3 494 902 | 6/2019 |
| EP | 3 632 337 | 4/2020 |
| EP | 3340890 B1 | 7/2022 |
| JP | 2010527742 A | 8/2010 |
| JP | 2016168173 A | 9/2016 |
| WO | WO 2004/082532 | 9/2004 |
| WO | WO 2008/150346 A1 | 12/2008 |
| WO | WO 2013/009998 A2 | 1/2013 |
| WO | WO 2015/189307 | 12/2015 |
| WO | WO 2017/035363 A1 | 3/2017 |
| WO | WO 2018/071717 A1 | 4/2018 |
| WO | WO 2018/178979 | 10/2018 |
| WO | WO 2019/212894 | 11/2019 |
| WO | WO 2020/074738 | 4/2020 |
| WO | WO 2020/198259 | 10/2020 |
| WO | WO 2021/194964 | 9/2021 |
| WO | WO 2022/010931 A1 | 1/2022 |
| WO | WO 2022/047333 | 3/2022 |
| WO | WO 2023/137343 A1 | 7/2023 |
| WO | WO 2023/192189 A1 | 10/2023 |

OTHER PUBLICATIONS

PCT Search Report and Written Opinion for PCT Application No. PCT/US2021/023475 dated Aug. 30, 2021; 25 pages.

U.S. Appl. No. 18/15311, filed Jan. 11, 2023, Lashinski et al.

U.S. Appl. No. 18/190,661, filed Mar. 27, 2023, Lashinski et al.

U.S. Appl. No. 17/180,121, filed Feb. 19, 2021, Lashinski et al.

WATCHMAN® Left Atrial Appendage Closure Device, Patient Information Guide; Boston Scientific; 9 pages.

WATCHMAN® Left Atrial Appendage Closure Device, Product Brochure; 6 pages dated as copyright 2018.

"Watchman Stroke Device Lawsuit;" https://www.nationalinjuryhelp.com/watchman-stroke-device-lawsuit/; 7 pages.

Cardia Delivery System, 1 page, dated as available at http://www.cardia.com/ds.html on Mar. 7, 2019 by the Wayback Machine internet archive (accessed and printed on May 6, 2020).

Cardia Fenestrated Fontan Closure System, 1 page, dated as available at http://www.cardia.com/fontan.html on Feb. 11, 2019 by the Wayback Machine internet archive (accessed and printed on May 6, 2020).

Densford, Fink, "Prominent cardiologist calls for a halt to Watchman implants;" https://www.massdevice.com/prominent-cardiologist-calls-for-a-halt-to-watchman-implants/; Nov. 10, 2016; 12 pages.

Kelley Drye & Warren LLP, "Texas Court dismisses off-label device marketing FCA case;" Lexology; Oct. 27, 2010; 2 pages.

Perriello, Brad, "Jury hands Covidien's ev3 subsidiary a possible $275M loss;" https://www.massdevice.com/jury-hands-covidiens-ev3-subsidiary-possible-275m-loss/; Aug. 13, 2013; 12 pages.

Rosenthal et al., "What is the efficacy and safety of devices for left atrial appendage (LAA) closure/litigation in atrial fibrillation (Afib) AF)?;" Medscape; Jul. 25, 2019; 2 pages.

Ultrasept Cribriform Device, 1 page, dated as available at http://www.cardia.com/cribriform.html on Feb. 11, 2019by the Wayback Machine internet archive (accessed and printed on May 6, 2020).

Ultrasept Left Atrial Appendage Closure Device, 1 page, dated as available at http://www.cardia.com/laa.html on Mar. 7, 2019 by the Wayback Machine internet archive (accessed and printed on May 6, 2020).

Ultrasept Patent Foramen Ovale Closure Device, 1 page dated as available at http://www.cardia.com/pfo.html on of Mar. 7, 2019 by the Wayback Machine internet archive (accessed and printed on May 6, 2020).

Ultrasept Atrial Septal Defect Closure Device, http://www.cardia.com/asd.html, 1 page, dated as available as of March 7, 2019by the Wayback Machine internet archive (accessed and printed on May 6, 2020).

Search Report and Written Opinion for PCT Application No. PCT/US2020/024513 mailed Jun. 15, 2020; 21 pages.

* cited by examiner

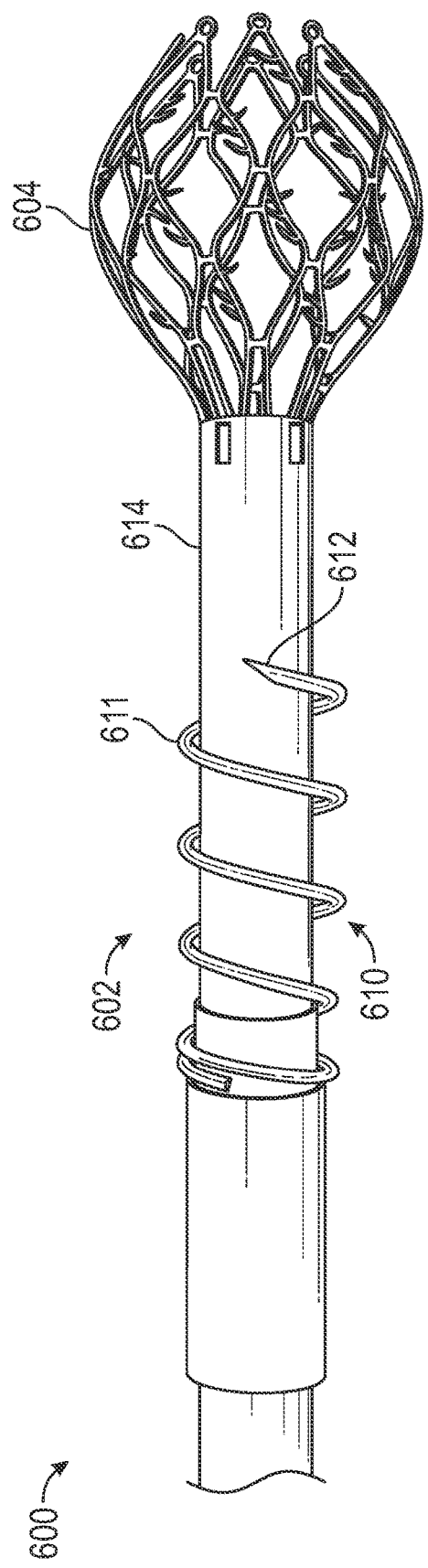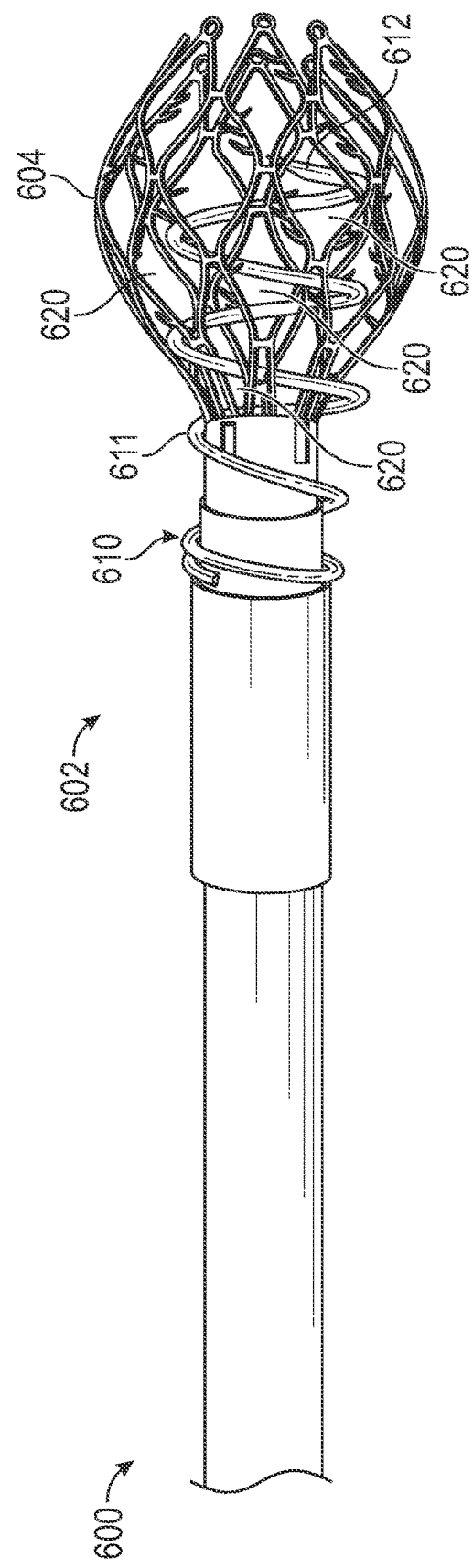

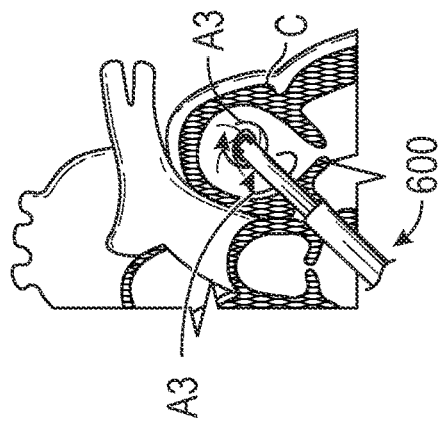
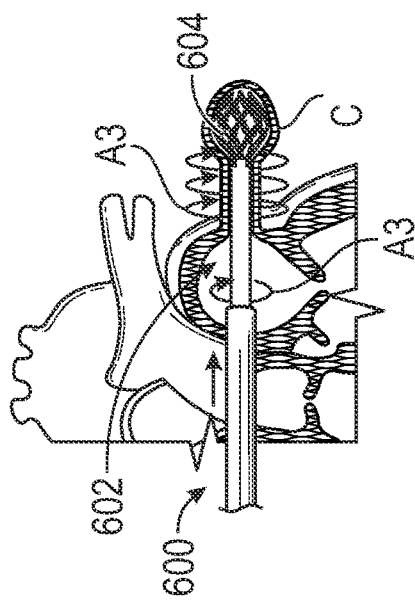
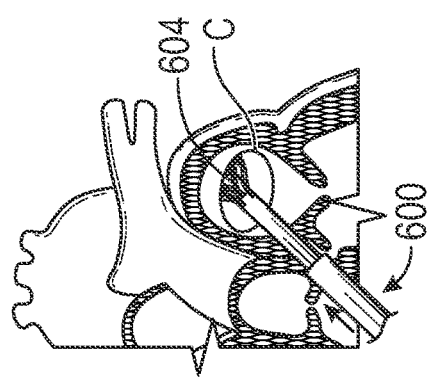
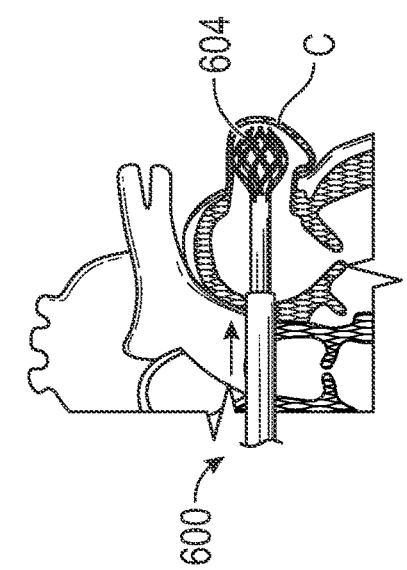
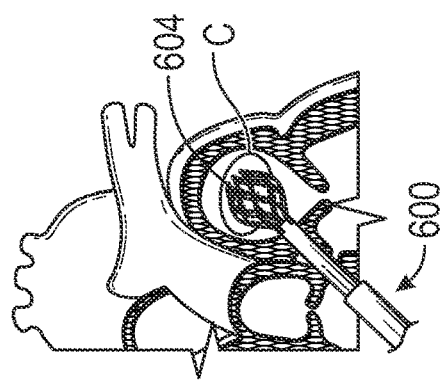
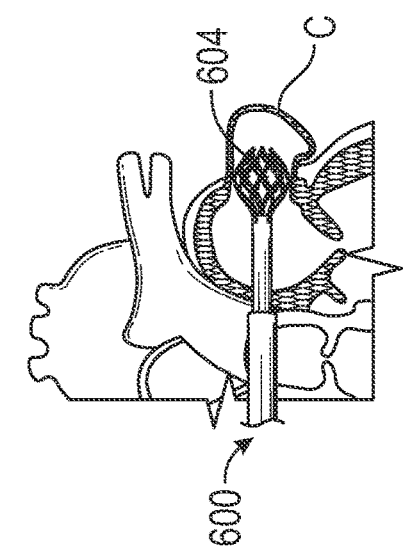

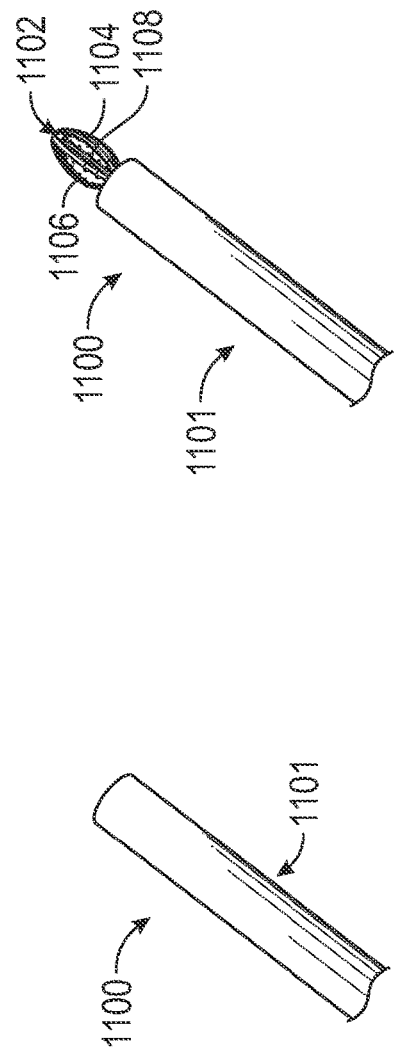
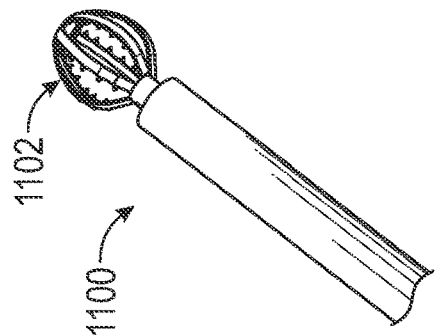
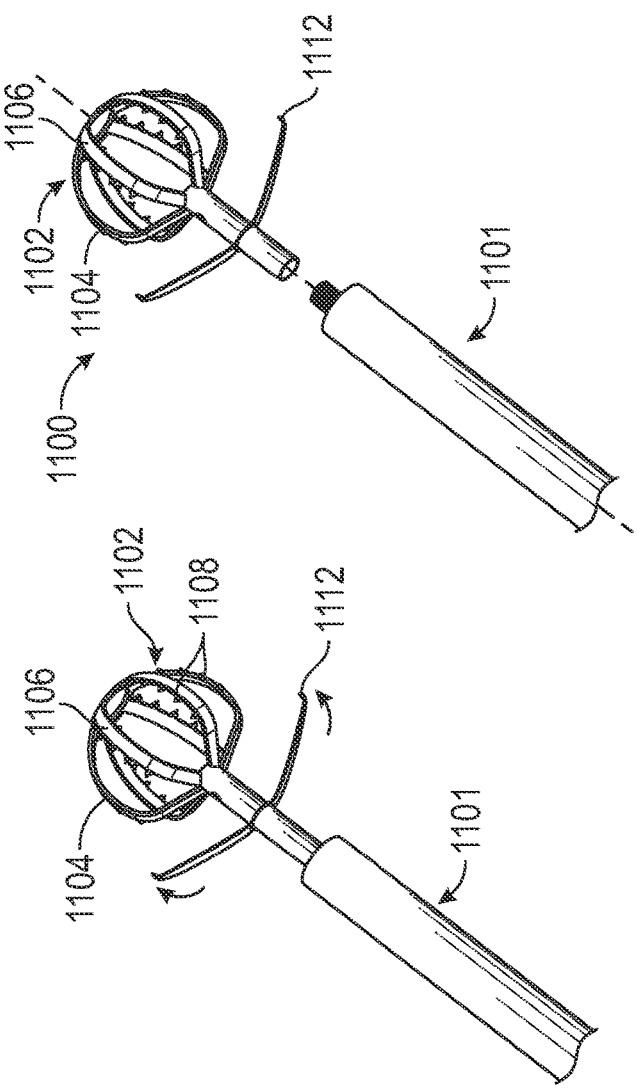
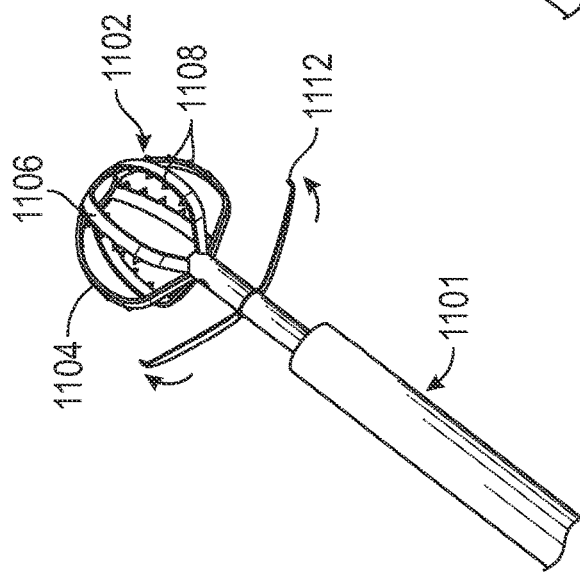
FIG. 47A
FIG. 47B
FIG. 47C
FIG. 47D
FIG. 47E
FIG. 47F

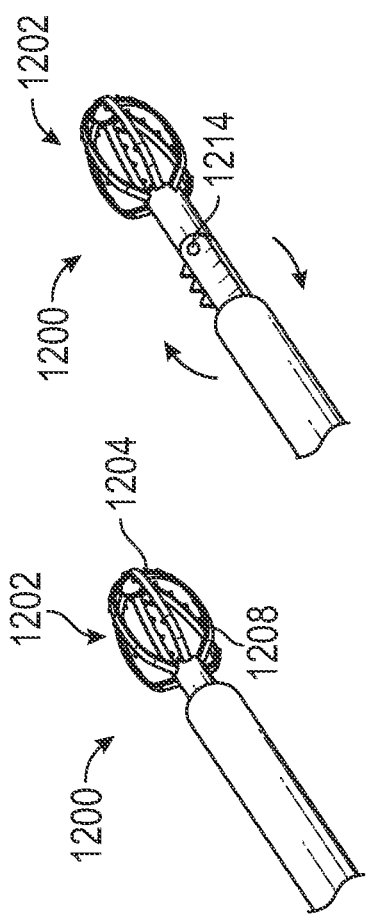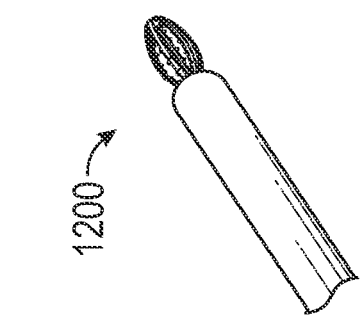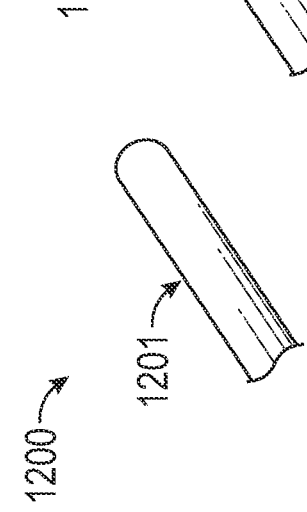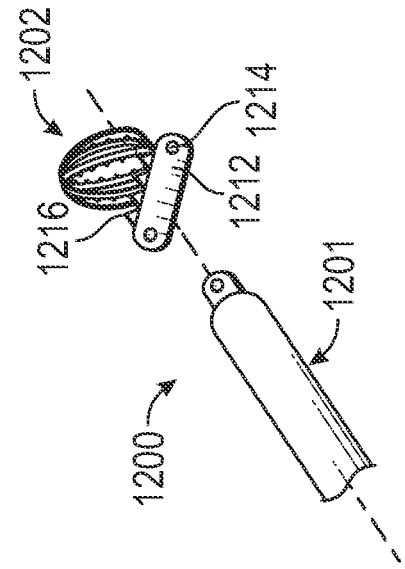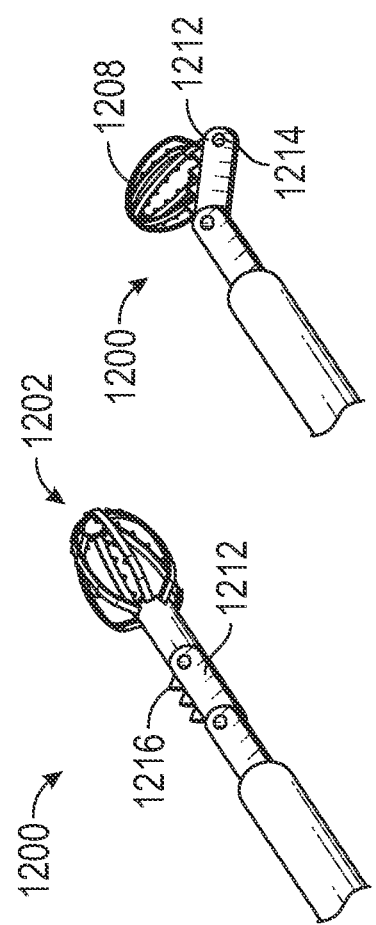
FIG. 49A  FIG. 49B  FIG. 49C  FIG. 49D
FIG. 49E  FIG. 49F  FIG. 49G

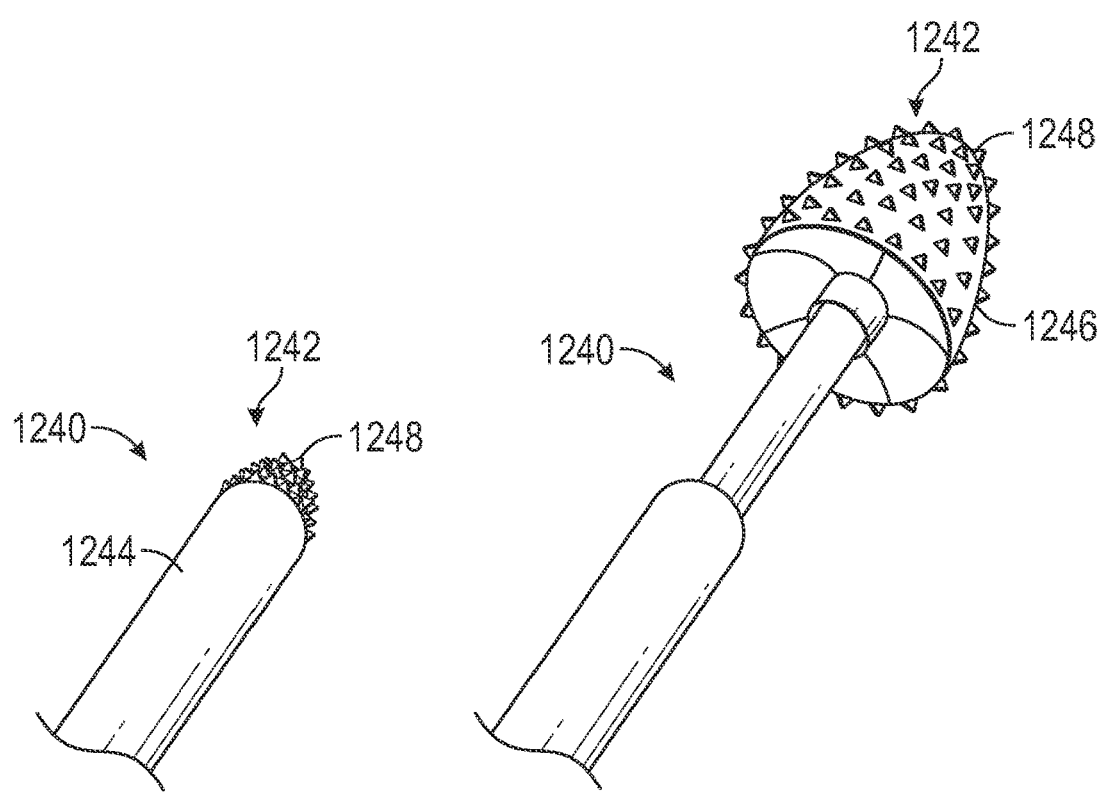
FIG. 56A
FIG. 56B
FIG. 57A
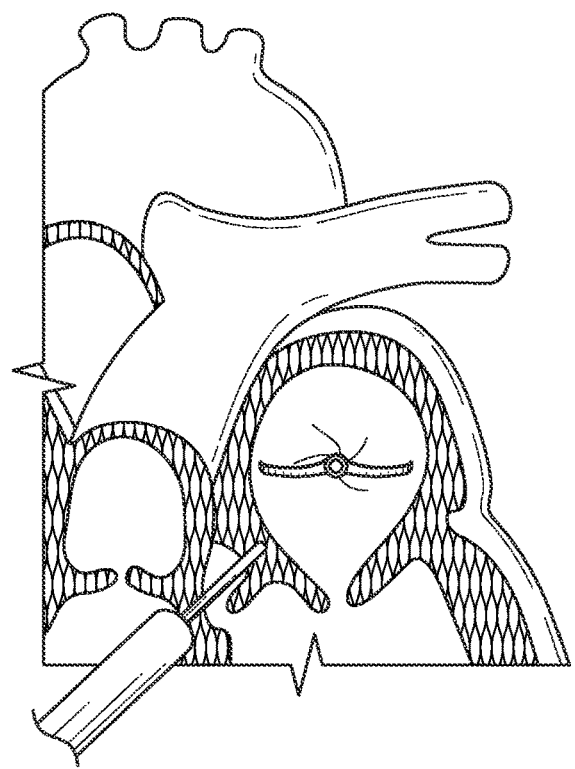
FIG. 57B

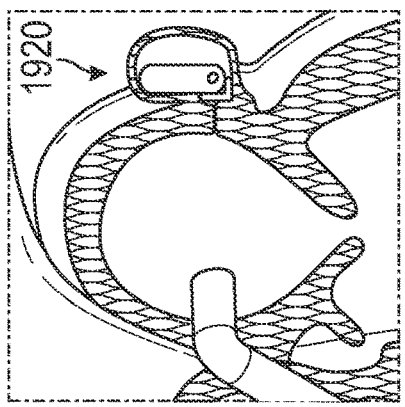
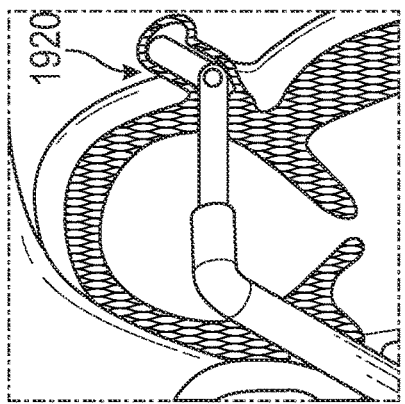
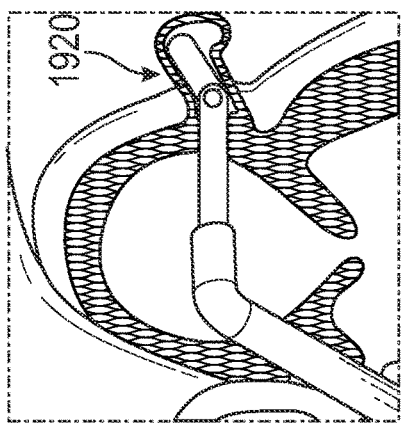
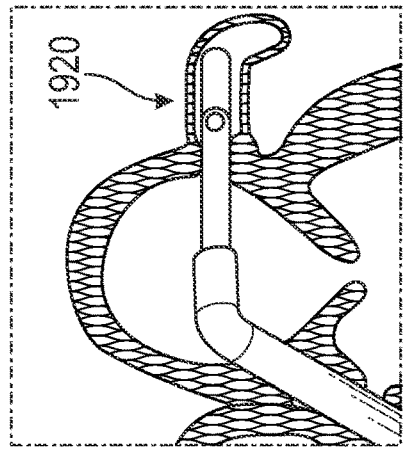
FIG. 64D
FIG. 64C
FIG. 64B
FIG. 64A

US 12,303,116 B2

DEVICES, SYSTEMS, AND METHODS FOR OCCLUDING CAVITIES WITHIN THE BODY

PRIORITY CLAIM AND INCORPORATION BY REFERENCE

The present application claims priority from U.S. Patent Application No. 62/994,240, filed on Mar. 24, 2020, titled DEVICES, SYSTEMS AND METHODS FOR OCCLUDING CAVITIES WITHIN THE BODY, the contents of which is hereby incorporated by reference herein in its entirety as if fully set forth herein. The benefit of priority is claimed under the appropriate legal basis including, without limitation, under 35 U.S.C. § 119(e).

FIELD OF THE DISCLOSURE

Embodiments of the present disclosure relate to devices, apparatuses, and methods for closing or occluding cavities within the body.

BACKGROUND

Current methods and devices for the treatment of wounds in remote and emergency situations are limited and have drawbacks. For example, wounds on the battlefield may be difficult and time-consuming to contain. A need exists for more rapid and effective wound closure devices and methods for use in emergency situations, remote areas where medical help is difficult to obtain, and even in battlefield situations.

Mitral regurgitation is increasingly prevalent. In many cases, mitral regurgitation is due to flail leaflet, ruptured chordae, or annular dilatation, often termed as Type I or Type II mitral valve disease. Mitral valve repair can be performed to treat diseases of the mitral valve, including mitral regurgitation. In some cases, mitral valve repair surgery can include implantation of an annuloplasty ring, chordal repair or plication and possible removal of excess valve tissue so that the leaflets can close coapt and close completely without regurgitant flow. Existing devices and methods for the mitral valve repair require highly talented cardiac surgeons. Many cardiac surgeons do not have this advanced training and experience for such devices or techniques, making mitral valve repair too difficult to perform for many surgeons.

Weight loss surgeries are used to slow down digestion, reduce weight, lower the risk of diabetes, and lower the risk of mortality in obese patients. Restrictive surgery is one form of weight loss surgery that reduces the size of the stomach. One example is the LapBand device produced by ReShape Lifesciences.

SUMMARY OF SOME EXEMPLIFYING EMBODIMENTS

The systems, methods and devices of this disclosure each have several innovative aspects, implementations, or aspects, no single one of which is solely responsible for the desirable attributes disclosed herein.

Some embodiments of the devices for reshaping, closing, or occluding a cavity within the body disclosed herein can include an implant configured to move between a first state and a second state and a catheter configured to advance the implant into, near or adjacent the cavity when the implant is in the first state, wherein the implant can be configured to move from the first state to the second state so that at least a portion of the implant engages a wall portion of the cavity after the implant has been advanced into, near or adjacent the cavity, and wherein the implant can be configured to twist at least a portion of the cavity or tissue near or adjacent the cavity when the implant is rotated from a first rotational position to a second rotational position when the implant is in the second state. In any embodiments disclosed herein, the twisting movement or step can be accomplished by a torque catheter.

Some embodiments of the devices for reshaping, closing or occluding a wound disclosed herein can include an implant including a contact member configured to move between a first state and a second state and a securing element. Any embodiments of the devices disclosed herein for reshaping, closing or occluding a wound can, in additional embodiments, include one or more of the following features or details, in any combination: wherein the contact member is configured to move from the first state to the second state so that at least a portion of the contact member engages a wall portion of a cavity of the wound after the contact member has been advanced into the cavity; wherein the contact member is configured to rotate at least in a first direction from a first rotational position (also referred to as a first position) to a second rotational position (also referred to as a second position); wherein the contact member is configured to twist at least a portion of the wall portion of the cavity of the wound in the first direction when the contact member is rotated from the first rotational position to the second rotational position to draw at least a first portion of the wall portion of the cavity toward a second portion of the wall portion of the cavity; wherein the securing element is configured to prevent a rotation of the wall portion of the cavity of the wound in a second direction when the securing element is in an operable state, wherein the second direction is opposite to the first direction; wherein the contact member is self-expandable such that at least a portion of the contact member automatically expands from the first state to the second state when a restraint is removed from the contact member; wherein the contact member is biased to remain in the second state after deployment into the cavity of the wound; wherein the contact member is configured to be removable from the cavity after the securing element is implanted over the cavity; wherein the contact member is configured to be rotated in a clockwise or a counter-clockwise direction; wherein the device is configured to cause a tissue of the cavity of the wound to constrict around an outer surface of a body portion of the device when the contact member is rotated to the second rotational position, and the securing element configured to engage with the tissue of the cavity that has constricted around the outer surface of the body portion of the device or a tissue adjacent to the cavity to prevent rotation of the implant and/or the tissue in the second direction; wherein the securing element has a plurality of tissue anchors configured to engage with a portion of a tissue of the cavity that has constricted around the outer surface of the body portion of the device or a tissue adjacent to the cavity to prevent rotation of the implant and/or the tissue in the second direction; and/or wherein the securing element has a helical shape and is configured to rotate about a body portion of the implant during the implantation procedures.

Any embodiments of the devices disclosed herein for reshaping, closing or occluding a wound can, in additional embodiments, include one or more of the following features or details, in any combination: wherein the implant is configured to rotate in a first direction from the first rotational position to the second rotational position, and the implant is configured to prevent rotation of the implant in a second direction after the implant has been fully deployed, wherein the second direction is opposite to the first direction; wherein the contact member has a plurality of tissue anchors on an outside surface thereof; wherein the plurality of tissue anchors on the outside surface of the contact member are configured to engage an inner wall surface of the cavity after the contact member has been moved to the second state; wherein the second rotational position is from approximately one-quarter of a complete rotation to one or more complete rotations relative to the first rotational position; further including a retaining member configured to bias the securing element toward the contact member; including a retaining member configured to couple the securing element with the contact member; including a retaining member configured to couple the securing element with the contact member, wherein the retaining member has a threaded shaft; wherein the contact member is configured to rotate at least in a first direction from a first rotational position to a second rotational position when a torque is applied to the contact member; wherein the device is configured such that the contact member can be removed from the cavity after the securing element has been deployed to the operable state of the securing element, and wherein the securing element is configured to prevent a rotation of the implant in the second direction when the securing element is in an operable state after the contact member has been removed; wherein only a portion of the securing element extends out of the cavity after deployment of the device, and all other portions of the device are internal to the cavity after deployment of the device; and/or wherein only approximately 10% or less of an overall length of the deployed device extends out of the cavity after deployment of the device.

Some embodiments of the devices for reshaping, closing or occluding a cavity disclosed herein can include an implant having a contact member configured to move between a first state and a second state, and a catheter configured to advance the contact member into the cavity when the contact member is in the first state and to cause the contact member to move from the first state to the second state so that an outside surface of the contact member expands against an inner wall surface of the cavity after the contact member has been advanced into the cavity. Any embodiments of the devices disclosed herein for reshaping, closing or occluding a cavity can, in additional embodiments, include one or more of the following features or details, in any combination: wherein the catheter is configured to exert a torque on the contact member when at least a portion of the catheter is rotated until a predetermine torque level is reached to rotate the contact member from a first rotational position to a second rotational position so that the contact member can twist at least a portion of the cavity; wherein the contact member is configured to move from the first state to the second state so that at least a portion of the contact member engages a wall portion of the cavity after the contact member has been advanced into the cavity; wherein the contact member is configured to rotate at least in a first direction from a first rotational position to a second rotational position; wherein the contact member is configured to twist at least a portion of the wall portion of the cavity in the first direction when the contact member is rotated from the first rotational position to the second rotational position to draw at least a first portion of the wall portion of the cavity toward a second portion of the wall portion of the cavity; wherein the securing element is configured to prevent a rotation of the wall portion of the cavity in a second direction when the securing element is in an operable state, wherein the second direction is opposite to the first direction; wherein the contact member is self-expandable such that at least a portion of the contact member automatically expands from the first state to the second state when a restraint is removed from the contact member; wherein the contact member is biased to remain in the second state after deployment into the cavity; wherein the contact member is configured to be removable from the cavity after the securing element is implanted over the cavity; wherein the contact member is configured to be rotated in a clockwise or a counter-clockwise direction; wherein the device is configured to cause a tissue of the cavity to constrict around an outer surface of a body portion of the device when the contact member is rotated to the second rotational position, and the securing element configured to engage with the tissue of the cavity that has constricted around the outer surface of the body portion of the device or a tissue adjacent to the cavity to prevent rotation of the implant and/or the tissue in the second direction; wherein the securing element has a plurality of tissue anchors configured to engage with a portion of a tissue of the cavity that has constricted around the outer surface of the body portion of the device or a tissue adjacent to the cavity to prevent rotation of the implant and/or the tissue in the second direction; and/or wherein the securing element has a helical shape and is configured to rotate about a body portion of the implant during the implantation procedures.

Any embodiments of the devices disclosed herein for reshaping, closing or occluding a cavity can, in additional embodiments, include one or more of the following features or details, in any combination: wherein the implant is configured to rotate in a first direction from the first rotational position to the second rotational position, and the implant is configured to prevent rotation of the implant in a second direction after the implant has been fully deployed, wherein the second direction is opposite to the first direction; wherein the contact member has a plurality of tissue anchors on an outside surface thereof; wherein the plurality of tissue anchors on the outside surface of the contact member are configured to engage an inner wall surface of the cavity after the contact member has been moved to the second state; wherein the second rotational position is from approximately one-quarter of a complete rotation to one or more complete rotations relative to the first rotational position; further including a retaining member configured to bias the securing element toward the contact member; including a retaining member configured to couple the securing element with the contact member; including a retaining member configured to couple the securing element with the contact member, wherein the retaining member has a threaded shaft; wherein the contact member is configured to rotate at least in a first direction from a first rotational position to a second rotational position when a torque is applied to the contact member; wherein the device is configured such that the contact member can be removed from the cavity after the securing element has been deployed to the operable state of the securing element, and wherein the securing element is configured to prevent a rotation of the implant in the second direction when the securing element is in an operable state after the contact member has been removed; wherein only a portion of the securing element extends out of the cavity after deployment of the device, and all other portions of the device are internal to the cavity after deployment of the device; and/or wherein only approximately 10% or less of an overall length of the deployed device extends out of the cavity after deployment of the device.

Some embodiments of the methods for reshaping, closing or occluding a cavity disclosed herein can include advancing a deployment device having an implant into the cavity, wherein the implant is configured to be moved from a first state to a second state, and wherein at least a portion of the implant is enlarged in a radial direction when the implant is in the second state as compared to the first state, moving the implant from the first state to the second state within the cavity so as to move at least a portion of an outside surface of the implant or one or more tissue anchors extending away from an outer surface of the implant against an inner wall surface of the cavity, rotating the implant from a first rotational position to a second rotational position to twist the cavity, and preventing the implant from rotating back to the first rotational position.

Any embodiments of the methods disclosed herein for reshaping, closing or occluding a cavity can, in additional embodiments, include one or more of the following steps, features, or details, in any combination: wherein the implant is self-expanding and wherein moving the implant from the first state to the second state includes advancing the implant out of a distal end of the deployment device; wherein engaging a wall portion on an inside of the cavity includes engaging a wall portion on an inside of the cavity with one or more tissue anchors positioned on an outside surface of the implant; wherein preventing the implant from rotating back to the first rotational position includes engaging a tissue wall with an anchor element to prevent relative movement between the implant and the tissue wall; wherein preventing the implant from rotating back to the first rotational position includes engaging a tissue wall with an anchor element, and wherein the anchor element is configured to be secured to the implant to prevent a rotation between the implant and the anchor element; wherein preventing the implant from rotating back to the first rotational position includes engaging a tissue surface adjacent to the cavity with an anchor element, wherein the anchor element is rotationally fixed relative to the implant and configured to prevent the implant from rotating back to the first rotational position; wherein preventing the implant from rotating back to the first rotational position includes engaging a tissue surface adjacent to the cavity outside of the closed portion of the cavity with an anchor element, wherein the anchor element is rotationally fixed relative to the implant and configured to prevent the implant from rotating back to the first rotational position; wherein the anchor element has a plurality of tissue anchors on at least one surface thereof configured to engage with the tissue outside of the cavity; wherein rotating the implant from the first rotational position to the second rotational position to twist the cavity includes rotating the implant until an opening of the cavity is substantially or completely closed; and/or wherein the cavity is a cavity of the stomach and the method further includes advancing the contact member into contact with a wall of the stomach to create a depression in the wall of the stomach, twisting and/or further advancing the contact member to create a secondary cavity in the wall of the stomach, and occluding the secondary cavity by twisting the contact member until an opening of the secondary cavity collapses about a portion of the implant.

Any embodiments of the methods disclosed herein for reshaping, closing or occluding a cavity can, in additional embodiments, include one or more of the following steps, features, or details, in any combination: wherein the cavity is a space in a commissure of a mitral valve, and the method includes occluding the space in the commissure of the mitral valve; wherein rotating the implant from the first rotational position to the second rotational position to twist the cavity includes rotating the implant at least approximately 180 degrees in either direction from the first rotational position; wherein rotating the implant from the first rotational position to the second rotational position to twist the cavity includes rotating the implant from approximately 90 degrees to approximately 360 degrees in either direction from the first rotational position; wherein rotating the implant from the first rotational position to the second rotational position to twist the cavity includes exerting a torque on the implant to rotate the implant in either direction from the first rotational position until a threshold predetermined torque level is reached, holding the implant in the second rotational position, and securing the implant in approximately the second rotational position relative to a tissue surface surrounding the cavity; wherein a maximum predetermined torque level is from approximately 025 in-oz of torque to approximately 50 in-oz of torque; and/or wherein a maximum predetermined torque level is from approximately 5 in-oz of torque to approximately 25 in-oz of torque.

Some embodiments of the implant for deployment within a cavity or vessel disclosed herein can include an expandable body, a plurality of tissue anchors on an outside surface of the expandable body configured to engage with an inner wall surface of the cavity or vessel, and a securing element coupled with the expandable body configured to engage with a tissue surface adjacent to the inner wall surface of the cavity or vessel.

Some embodiments of the devices for reshaping, closing or occluding a cavity disclosed herein can include an expandable implant having a plurality of tissue anchors on an outside surface of a portion thereof, the expandable implant being configured to move between a first state in which the implant is substantially collapsed and a second state in which at least a portion of the implant is expanded, a catheter configured to advance the implant into the cavity when the implant is in the first state and to selectively cause the implant to move from the first state to the second state so that at least some of the plurality of tissue anchors engage an inner wall surface of the cavity after the implant has been advanced into the cavity, wherein the catheter is configured to rotate the implant in a first direction from a first rotational position to a second rotational position so that the implant can twist the cavity.

Some embodiments of the devices for reshaping, closing or occluding a cavity disclosed herein can include an implant configured to move between a first state and a second state, a catheter configured to advance the implant into the cavity when the implant is in the first state and to cause the implant to move from the first state to the second state so that an outside surface of the implant moves against an inner wall surface of the cavity after the implant has been advanced into the cavity, wherein the catheter is configured to rotate the implant in a first direction from a first rotational position to a second rotational position so that the implant can twist at least a portion of the cavity when the implant is in the second state.

Some embodiments of the methods for reshaping, closing or occluding a cavity disclosed herein can include advancing a deployment device having an implant into the cavity, wherein the implant is configured to be moved from a first state to a second state, and wherein at least a portion of the implant is larger in size in a radial direction when the implant is in the second state as compared to the first state, moving the implant from the first state to the second state within the cavity so as to move at least a portion of the implant against a portion of an inner wall surface of the cavity, rotating the implant from a first rotational position to a second rotational position to twist the cavity and to draw tissue of the cavity together, holding the tissue that has been drawn together with a securing element to hold the tissue together, and rotating the implant or allowing the implant to rotate back toward the first rotational position while continuing to hold the tissue that has been drawn together with the securing element. In any embodiments, moving the implant from the first state to the second state within the cavity so as to move at least a portion of the implant against a portion of an inner wall surface of the cavity can include moving at least a portion of an outside wall of the implant and/or one or more tissue anchors extending away from an outer surface of the implant against the inner wall surface of the cavity.

Some embodiments of the devices for drawing a first tissue surface toward a second tissue surface disclosed herein can include a contact member configured to expand from a first state to a second state and a securing element configured to move from a first state to a second state, wherein the contact member is configured to expand from the first state to the second state so that at least a portion of the contact member engages at least a distal portion of the first tissue surface and at least a distal portion of the second tissue surface, wherein the contact member is configured to rotate at least in a first direction from a first rotational position to a second rotational position, wherein the rotation of the contact member in the first direction causes at least a proximal portion of the first tissue surface to twist and to move toward a proximal portion of the second tissue surface, and wherein the securing element is configured to prevent a rotation of the implant in a second direction when the securing element is in an operable state and engaged with a tissue portion adjacent to and/or including the proximal portions of the first and second tissue surfaces, wherein the second direction is opposite to the first direction. Any embodiments of the devices disclosed herein for drawing a first tissue surface toward a second tissue surface disclosed herein can, in additional embodiments, include one or more of the following features or details, in any combination: wherein the device is configured to occlude or close a cavity in a body having the first and second tissue surfaces; wherein the first and second tissue surfaces are tissue surfaces within a cavity within the body; and/or wherein the rotation of the contact member further causes the proximal portion of the second tissue surface to twist and to move toward the proximal portion of the first tissue surface.

Disclosed herein are embodiments of devices and systems for treating a cavity within the body that can include an implant comprising a contact member configured to move between a first state and a second state, and a securing element, wherein the contact member is configured to move from the first state to the second state so that at least a portion of the contact member engages a wall portion of the cavity after the contact member has been advanced into the cavity, the contact member is configured to rotate at least in a first direction from a first rotational position to a second rotational position, the contact member is configured to twist at least a portion of the cavity when the contact member is rotated from the first rotational position to the second rotational position, and the securing element is configured to prevent a rotation of the implant in a second direction when the securing element is in an operable state, wherein the second direction is opposite to the first direction.

Also disclosed herein are embodiments of devices and systems for treating a cavity within the body that can include an implant configured to move between a first state and a second state, a catheter configured to advance the implant into the cavity when the implant is in the first state and to cause the implant to move from the first state to the second state so that an outside surface of the implant moves against an inner wall surface of the cavity after the implant has been advanced into the cavity, wherein the catheter is configured to rotate the implant in a first direction from a first rotational position to a second rotational position so that the implant can twist at least a portion of the cavity when the implant is in the second state.

Also disclosed herein are embodiments of devices and systems for drawing a first tissue surface toward a second tissue surface, including a contact member configured to expand from a first state to a second state and a securing element configured to move from a first state to a second state, wherein the contact member can be configured to expand from the first state to the second state so that at least a portion of the contact member engages at least a distal portion of the first tissue surface and at least a distal portion of the second tissue surface, the contact member can be configured to rotate at least in a first direction from a first rotational position to a second rotational position, wherein the rotation of the contact member in the first direction causes at least a proximal portion of the first tissue surface to twist and to move toward a proximal portion of the second tissue surface, and wherein the securing element is configured to prevent a rotation of the implant in a second direction when the securing element is in an operable state and engaged with a tissue portion adjacent to and/or comprising the proximal portions of the first and second tissue surfaces, wherein the second direction is opposite to the first direction. Further, in any device and/or system embodiments disclosed herein, the device can be configured to occlude or close a cavity in a body having the first and second tissue surfaces, the first and second tissue surfaces can be tissue surfaces within any cavity within the body, and/or wherein the rotation of the contact member further causes the proximal portion of the second tissue surface to twist and to move toward the proximal portion of the first tissue surface.

Any embodiments of the devices and systems disclosed herein can include, in additional embodiments, one or more of the following features, components, and/or details, in any combination with any of the other features, components, and/or details of any other embodiments disclosed herein: wherein the implant is self-expandable such that the implant automatically expands from the first state to the second state when a restraint is removed from the implant; wherein the contact member is self-expandable such that at least a portion of the contact member automatically expands from the first state to the second state when a restraint is removed from the contact member; wherein the implant is substantially collapsed when the implant is in the first state and is expanded when the implant is in the second state such that a size of the implant is bigger when the implant is in the second state than when the implant is in the first state; wherein the contact member is biased to remain in the second state after deployment into the cavity; wherein the contact member is configured to be rotated in a clockwise or a counter-clockwise direction; wherein the device is configured to cause a tissue of the cavity to constrict around an outer surface of a body portion of the implant when the contact member is rotated to the second rotational position, and the securing element is configured to engage with the tissue that has constricted around the outer surface of the body portion of the implant to prevent rotation of the implant in the second direction; wherein the securing element has a plurality of tissue anchors configured to engage with an internal wall of the space outside of or adjacent to the cavity; wherein the securing element has a helical shape and is configured to rotate about a body portion of the implant during the implantation procedures; wherein the implant is configured to rotate in a first direction from the first rotational position to the second rotational position; wherein the implant is configured to prevent rotation of the implant in a second direction after the implant has been fully deployed, wherein the second direction is opposite to the first direction; wherein the contact member has a plurality of tissue anchors on an outside surface thereof; wherein the plurality of tissue anchors on the outside surface of the contact member are configured to engage an inner wall surface of the cavity after the contact member has been moved to the second state; wherein the implant comprises a securing element configured to engage with a tissue portion of the space outside of or adjacent to the cavity; wherein the second rotational position is at least one-quarter of a complete rotation relative to the first rotational position; wherein the second rotational position is at least one-half of a complete rotation relative to the first rotational position; and/or wherein the second rotational position is from approximately one-quarter of a complete rotation to one or more complete rotations relative to the first rotational position.

Further, any embodiments of the devices and systems disclosed herein can include, in additional embodiments, one or more of the following features, components, and/or details, in any combination with any of the other features, components, and/or details of any other embodiments disclosed herein: further comprising a catheter selectively coupled with the contact member and configured to exert a torque on the contact member to rotate the contact member from the first rotational position until a threshold predetermined torque level is reached; wherein a threshold predetermined torque level is from approximately 0.25 in-oz of torque to approximately 10 in-oz of torque; wherein a threshold predetermined torque level is from approximately 0.5 in-oz of torque to approximately 5 in-oz of torque; further comprising a retention member configured to bias the securing element toward a tissue wall of the cavity; further comprising a retention member configured to bias the securing element toward the contact member; further comprising a retention member configured to couple the securing element with the contact member; wherein the retention member comprises a threaded shaft; wherein the device is configured such that a rotation of the retention member in a first direction causes the securing element to move toward the contact member; wherein the contact member is configured to rotate at least in a first direction from a first rotational position to a second rotational position when a torque is applied to the contact member; wherein the device is configured such that the contact member can be removed from the cavity after the securing element has been deployed to the operable state of the securing element; wherein the device is configured such that the contact member can be removed from the cavity after the securing element has been deployed to the operable state of the securing element, and wherein the securing element is configured to prevent a rotation of the tissue of the cavity that has been constricted as a result of the rotation of the contact member from the first rotational position to the second rotational position; wherein only a portion of the securing element extends out of the cavity after deployment of the device, and all other portions of the device are internal to the cavity after deployment of the device; wherein only approximately 10% or less of an overall length of the deployed device extends out of the cavity after deployment of the device; wherein the device is configured for use by a surgical robot device or system; a surgical robotic device, comprising one or more robotic arms and wherein the device of any embodiments disclosed herein is configured for use by the surgical robotic device; wherein the contact member and the securing element are integrally formed and/or monolithically formed; wherein the device is configured to cause a tissue of the cavity to constrict around an outer surface of a body portion of the implant when the contact member is rotated to the second rotational position, and the securing element is configured to compress the tissue that has constricted around the outer surface of the body portion of the implant between a distal surface of the securing element and the contact member to prevent rotation of the implant in the second direction.

Some embodiments of devices and systems for closing or occluding a cavity disclosed herein can include an implant configured to move between a first state and a second state and a catheter configured to advance the implant into the cavity when the implant is in the first state, wherein the implant can be configured to move from the first state to the second state so that at least a portion of the implant engages a wall portion of the cavity after the implant has been advanced into the cavity, and wherein the implant can be configured to twist at least a portion of the cavity when the implant is rotated from a first rotational position to a second rotational position when the implant is in the second state. In any embodiments disclosed herein, the twisting movement or step can be accomplished by a torque catheter.

Any embodiments of the devices and systems disclosed herein can, in additional embodiments, include one or more of the following features or details, in any combination: wherein the implant is configured to automatically rotate from the first rotational position to the second rotational position after the implant is in the second state; wherein the implant can be configured to be triggered or activated to thereafter automatically rotate from the first rotational position to the second rotational position; wherein the device has a spring that is coupled with the implant, the spring being configured to automatically rotate the implant when the spring is released or activated; wherein the implant can be self-expandable such that the implant automatically expands from the first state to the second state when a restraint is removed from the implant; wherein the implant can be self-expandable such that at least a portion of the implant automatically expands from the first state to the second state when the implant is advanced past a distal end of an outer sleeve of the catheter; wherein the implant is substantially collapsed when the implant is in the first state and can be expanded when the implant is in the second state such that a size of the implant can be bigger when the implant is in the second state than when the implant is in the first state; wherein the implant can be biased to remain in the second state after deployment into the cavity; wherein the implant can be configured to be rotated in a clockwise or a counterclockwise direction; wherein the implant can include a securing element configured to engage with an internal wall of the space outside of or adjacent to the cavity; wherein the implant can include a securing element configured to engage with an internal wall of the space outside of or adjacent to the cavity, wherein the securing element has a helical shape and is configured to rotate about a body portion of the implant during the implantation procedures; wherein the implant can include a corkscrew shaped securing element configured to engage with an internal wall of the space outside of or adjacent to the cavity; wherein the implant can include a securing element having a corkscrew tissue anchor to engage the internal wall of the cavity and/or an internal wall of the space outside of or adjacent to the cavity; wherein the implant can include a securing element having a plurality of tissue anchors configured to engage with an internal wall of the space adjacent to the cavity and/or of the cavity; wherein the implant can be configured to prevent the implant from rotating back to the first rotational position after the implant has been fully deployed; wherein the implant can be configured to rotate in a first direction from the first rotational position to the second rotational position, and the implant can be configured to prevent rotation of the implant in a second direction after the implant has been fully deployed, the second direction being opposite to the first direction.

Any embodiments of the devices and systems disclosed herein can, in additional embodiments, include one or more of the following features or details, in any combination: wherein the implant has a plurality of tissue anchors on an outside surface thereof; wherein the plurality of tissue anchors on the outside surface of the implant configured to engage an inner wall surface of the cavity after the implant has been moved to the second state; wherein the implant can include a securing element configured to engage with a tissue portion of the space outside of or adjacent to the cavity; wherein the second rotational position can be at least one-quarter or approximately one-quarter of a complete rotation (i.e., 90 degrees or approximately 90 degrees) relative to the first rotational position; wherein the second rotational position can be at least one-half or approximately one-half of a complete rotation (i.e., 180 degrees or approximately 180 degrees) relative to the first rotational position; wherein the second rotational position can be from one-quarter or approximately one-quarter of a complete rotation (i.e., 90 degrees or approximately 90 degrees) to one or more or approximately one or more complete rotations (i.e., 360 degrees or approximately 360 degrees or more) relative to the first rotational position; wherein the catheter can be configured to exert a torque on the implant to rotate the implant from the first rotational position until a threshold predetermined torque level is reached; wherein a threshold predetermined torque level can be from 0.25 or approximately 0.25 in-oz of torque to 10 or approximately 10 in-oz of torque; and/or wherein a threshold predetermined torque level can be from 0.5 or approximately 0.5 in-oz of torque to 5 or approximately 5 in-oz of torque.

Any embodiments of the devices and systems disclosed herein can include an implant having a contact member configured to move between a first state and a second state and a catheter configured to advance the contact member into the cavity when the contact member is in the first state and to cause the contact member to move from the first state to the second state so that an outside surface of the contact member expands against an inner wall surface of the cavity after the contact member has been advanced into the cavity, wherein the catheter is configured to exert a torque on the contact member when at least a portion of the catheter is rotated until a predetermine torque level is reached to rotate the contact member from a first rotational position to a second rotational position so that the contact member can twist at least a portion of the cavity.

Any embodiments of the devices and systems disclosed herein can include an expandable implant configured to move between a first state and a second state, a catheter configured to advance the implant into the cavity when the implant is in the first state and to cause the implant to move from the first state to the second state so that an outside surface of the implant expands against at least a portion of an inner wall surface of the cavity after the implant has been advanced into the cavity. In any embodiments of the device for closing or occluding an cavity disclosed herein, the catheter can be configured to exert a torque on the implant to rotate the implant from a first rotational position to a second rotational position so that the implant can twist at least a portion of the cavity until a predetermine torque level is reached, or in some embodiments, until the user decides to stop, whichever comes first.

Also disclosed herein are devices and systems for treating the cavity, which include a device configured to be inserted into the cavity and to engage the cavity tissue while the device is rotated to a rotated position to close the blood communication between the cavity and the adjacent space. In any embodiments of the apparatus, the device can be configured to be selectively lockable in the rotated position to at least substantially maintain the device in the rotated position after implantation, the device can include a securing element configured to engage a tissue surface adjacent to the cavity to maintain the device in the rotated position after implantation, the device can be round, spherical, or disc shaped when the device is in a deployed state in the cavity, the device can be expandable from a first collapsed state to a second expanded state, and/or the device can be self-expanding from a first collapsed state to a second expanded state.

Also disclosed herein are embodiments of methods for treating the cavity, including engaging a tissue of the cavity, and rotating the tissue of the cavity to close or occlude a blood communication between the cavity and a space adjacent to or outside of the cavity. In any embodiments of the methods disclosed herein, rotating the tissue of the cavity to close or occlude the blood communication between the cavity and the space adjacent to or outside of the cavity can include rotating the tissue of the cavity to close or occlude the opening (also referred to herein as an ostium) of the cavity. Further, any embodiments of the methods disclosed herein can further include securing the cavity in a rotated position to hold the cavity in a closed or occluded state.

Any embodiments of a method of closing or occluding a cavity disclosed herein can include advancing a deployment device having an implant into the cavity, wherein the implant can be configured to be moved from a first state to a second state. In some embodiments, at least a portion of the implant can be enlarged in a radial direction when the implant is in the second state as compared to the first state. The method can further include moving the implant from the first state to the second state within the cavity so as to move at least a portion of an outside wall of the implant or one or more tissue anchors extending away from an outer surface of the implant against at least a portion of an inner wall surface of the cavity, rotating the implant from a first rotational position to a second rotational position to twist the cavity, and preventing the implant from rotating back to the first rotational position.

Any embodiments of methods of closing or occluding an cavity disclosed herein can, in some additional embodiments, include one or more of the following steps, in any combination and in any combination with any of the other steps, features, or other details of any other embodiments: wherein the implant is self-expanding and wherein moving the implant from the first state to the second state comprises advancing the implant out of a distal end of the deployment device; wherein engaging a wall portion on an inside of the cavity comprises engaging a wall portion on an inside of the cavity with one or more tissue anchors positioned on an outside surface of the implant; wherein preventing the implant from rotating back to the first rotational position comprises engaging a tissue wall with an anchor element to prevent relative movement between the implant and the tissue wall; wherein preventing the implant from rotating back to the first rotational position comprises engaging a tissue wall with an anchor element, and wherein the anchor element is configured to be secured to the implant to prevent a rotation between the implant and the anchor element; wherein preventing the implant from rotating back to the first rotational position comprises engaging a tissue wall of the cavity and/or the space outside of or adjacent to the cavity with an anchor element, wherein the anchor element is rotationally fixed relative to the implant and configured to prevent the implant from rotating back to the first rotational position; wherein preventing the implant from rotating back to the first rotational position comprises engaging a tissue outside of the closed portion of the cavity with an anchor element, wherein the anchor element is rotationally fixed relative to the implant and configured to prevent the implant from rotating back to the first rotational position; wherein the anchor element comprises a plurality of tissue anchors on at least one surface thereof configured to engage with the internal wall of the space outside of or adjacent to the cavity and/or the tissue of the cavity; wherein rotating the implant from the first rotational position to the second rotational position to twist the cavity comprises rotating the implant until an opening of the cavity is substantially or completely closed; wherein rotating the implant from the first rotational position to the second rotational position to twist the cavity comprises rotating the implant at least approximately 90 degrees in either direction from the first rotational position; wherein rotating the implant from the first rotational position to the second rotational position to twist the cavity comprises rotating the implant at least approximately 180 degrees in either direction from the first rotational position; wherein rotating the implant from the first rotational position to the second rotational position to twist the cavity comprises rotating the implant from approximately 90 degrees to approximately 360 degrees in either direction from the first rotational position; wherein rotating the implant from the first rotational position to the second rotational position to twist the cavity comprises rotating the implant from approximately 90 degrees to approximately 180 degrees in either direction from the first rotational position; wherein rotating the implant from the first rotational position to the second rotational position to twist the cavity comprises exerting a torque on the implant to rotate the implant in either direction from the first rotational position until a threshold predetermined torque level is reached, holding the implant in the second rotational position, and securing the implant in approximately the second rotational position relative to a tissue surface surrounding the cavity; wherein a maximum predetermined torque level is from approximately 0.25 in-oz of torque to approximately 10 in-oz of torque; and/or wherein a maximum predetermined torque level is from approximately 0.5 in-oz of torque to approximately 5 in-oz of torque.

Any embodiments of the methods of closing or occluding an cavity disclosed herein can, in some additional embodiments, include one or more of the following steps, in any combination and in any combination with any of the other steps, features, or other details of any other embodiments: wherein the implant is self-expanding and wherein moving the implant from the first state to the second state can include advancing the implant out of a distal end of the deployment device; wherein engaging a wall portion on an inside of the cavity can include engaging at least a portion of a wall portion on an inside of the cavity or surrounding the cavity with one or more tissue anchors positioned on an outside surface of the implant; wherein preventing the implant from rotating back to the first rotational position can include engaging a tissue wall outside of the cavity with an anchor element; wherein the anchor element can be rotationally fixed to the implant to prevent relative movement between the anchor element and the implant; wherein preventing the implant from rotating back to the first rotational position can include engaging a tissue wall of the cavity and/or the space outside of or adjacent to the cavity with an anchor element; wherein the anchor element can be rotationally fixed relative to the implant and configured to prevent the implant from rotating back to the first rotational position; wherein preventing the implant from rotating back to the first rotational position can include engaging an internal wall of the space outside of the cavity with an anchor element; wherein the anchor element can be rotationally fixed relative to the implant and configured to prevent the implant from rotating back to the first rotational position; wherein the anchor element can include a plurality of tissue anchors on at least one surface thereof configured to engage with the internal wall of the space outside of the cavity; and/or wherein rotating the implant from the first rotational position to the second rotational position to twist the cavity can include rotating the implant until an opening of the cavity can be substantially or completely closed or occluded, or collapsed about an outer surface of the implant.

Any embodiments of the methods of closing or occluding an cavity disclosed herein can, in any additional embodiments, include one or more of the following steps, in any combination and in any combination with any of the other steps, features, or other details of any other embodiments: wherein rotating the implant from the first rotational position to the second rotational position to twist the cavity can include rotating the implant at least one-quarter or approximately one-quarter of a complete rotation (i.e., 90 degrees or approximately 90 degrees) relative to the first rotational position; wherein rotating the implant from the first rotational position to the second rotational position to twist the cavity can include rotating the implant at least one-half or approximately one-half of a complete rotation (i.e., 180 degrees or approximately 180 degrees) in either direction from the first rotational position; wherein rotating the implant from the first rotational position to the second rotational position to twist the cavity can include rotating the implant from one-quarter or approximately one-quarter of a complete rotation (i.e., 90 degrees or approximately 90 degrees) to one full turn or approximately one full turn (i.e., 360 degrees or approximately 360 degrees), or to more than one full turn (i.e., more than 360 degrees) in either direction from the first rotational position; wherein rotating the implant from the first rotational position to the second rotational position to twist the cavity can include rotating the implant from one-quarter or approximately one-quarter of a complete rotation (i.e., 90 degrees or approximately 90 degrees) to one-half of a full turn or approximately one-half of a full turn (i.e., 180 degrees or approximately 180 degrees), or to more than one full turn (i.e., more than 360 degrees) in either direction from the first rotational position; wherein rotating the implant from the first rotational position to the second rotational position to twist the cavity can include exerting a torque on the implant to rotate the implant in either direction from the first rotational position until a threshold predetermined torque level is reached; wherein rotating the implant from the first rotational position to the second rotational position to twist the cavity can include holding the implant in the second rotational position; wherein rotating the implant from the first rotational position to the second rotational position to twist the cavity can include securing the implant in approximately the second rotational position relative to a tissue surface surrounding the cavity; wherein a maximum predetermined torque level can be from approximately 0.25 in-oz of torque to approximately 10 in-oz of torque; and/or wherein a maximum predetermined torque level can be from approximately 0.5 in-oz of torque to approximately 5 in-oz of torque.

Some embodiments of an implant for deployment within a cavity or vessel disclosed herein include an expandable body, a plurality of tissue anchors on an outside surface of the expandable body configured to engage with an inner wall surface of the cavity or vessel, and an anchor element coupled with the expandable body configured to engage with a tissue surface adjacent to the inner wall surface of the cavity or vessel.

Any embodiments of the devices and systems disclosed herein can include an expandable implant having a plurality of tissue anchors on an outside surface thereof, the expandable implant being configured to move between a first state in which the implant is substantially collapsed and a second state in which at least a portion of the implant is expanded, and a catheter configured to advance the implant into the cavity when the implant is in the first state and to cause the implant to move from the first state to the second state so that at least some of the plurality of tissue anchors engage an inner wall surface of the cavity after the implant has been advanced into the cavity. In some embodiments, the catheter can be configured to rotate the implant in a first direction from a first rotational position to a second rotational position so that the implant can twist the wall of the cavity.

Some embodiments of the devices and systems for closing or occluding an cavity disclosed herein can include an implant configured to move between a first state and a second state, and a catheter configured to advance the implant into the cavity when the implant is in the first state and to cause the implant to move from the first state to the second state so that an outside surface of the implant moves against an inner wall surface of the cavity after the implant has been advanced into the cavity. In some embodiments, the catheter can be configured to rotate the implant in a first direction from a first rotational position to a second rotational position so that the implant can twist at least a portion of the cavity when the implant is in the second state.

Any embodiments of the methods of treating the cavity disclosed herein can include engaging a tissue of the cavity and rotating the tissue of the cavity to close or significantly close, or inhibit or substantially inhibit, a blood communication between the cavity and a space adjacent to or outside of the cavity. Any embodiments of the method(s) disclosed herein can include, in additional embodiments, one or more of the following features, components, steps, and/or details, in any combination with any of the other features, components, steps, and/or details of any other treatment method embodiments disclosed herein: further including rotating the tissue of the cavity to close the blood communication between the cavity and the space adjacent to or outside of the cavity can include rotating the tissue of the cavity to close the opening of the cavity, and/or further including securing the cavity in a rotated position to hold the cavity in a closed state.

Some embodiments of apparatuses for treating the cavity disclosed herein can include a device configured to be inserted into the cavity and to engage the cavity tissue while the device is rotated to a rotated position to close the blood communication between the cavity and the space adjacent to or outside of the cavity. In some embodiments, the device can be configured to be locked in the rotated position to maintain the device in the rotated position after implantation, wherein the device can include a securing element configured to engage a tissue surface adjacent to the cavity to maintain the device in the rotated position after implantation, wherein the device can be round, spherical, or disc shaped when the device is in a deployed state in the cavity, wherein the device can be expandable from a first collapsed state to a second expanded state, and/or wherein the device can be self-expanding from a first collapsed state to a second expanded state.

Disclosed herein are embodiments of devices for treating a cavity that include an implant having a contact member and a catheter configured to advance the contact member into the cavity and to cause the contact member to move against an inner wall surface of the cavity, wherein the catheter is configured to exert a torque on the contact member when at least a portion of the catheter is rotated until a predetermine torque level is reached to rotate the contact member from a first rotational position to a second rotational position so that the contact member can twist at least a portion of the cavity. In any embodiments disclosed herein, the contact member can be configured to be moved against the inner wall surface of the cavity without changing a state or shape of the contact member, and/or the contact member can be configured to be movable or expandable from a first state to a second state.

Disclosed herein are embodiments of devices for reducing an opening of the cavity that include a contact member and a securing element, wherein the contact member is configured to engage a tissue surface of the cavity, the contact member is configured to rotate at least a portion of the cavity in a first direction from a first rotational position to a second rotational position and to cause the opening of the cavity to reduce in size from a first size to a second size, and/or the securing element is configured to engage with at least a portion of tissue adjacent to the opening of the cavity and to prevent the opening of the cavity from expanding to the first size. In any embodiments disclosed herein, the contact member can be configured to engage a tissue surface on an outside surface of the cavity. Further, in any embodiments disclosed herein, the contact member can be configured to engage the tissue surface of the cavity without changing a state or shape of the contact member.

Also disclosed herein are additional embodiments of closure or occlusion devices for a cavity. In any embodiments disclosed herein, the device can include a delivery catheter and an implant that is advanceable through the delivery catheter when the implant is in a first state, wherein the implant has a first expandable portion and a second expandable portion, wherein the first and the second expandable portions of the implant are each independently expandable to a second state, and wherein the implant can be configured to block an opening of the cavity when the first and second expandable portions of the implant are in the second state.

Any embodiments of the devices and systems disclosed herein can include, in additional embodiments, one or more of the following features, components, and/or details, in any combination with any of the other features, components, and/or details of any other embodiments disclosed herein:

wherein the first expandable portion is a distal portion of the implant and the second expandable portion is a proximal portion of the implant; further including a removable restraint surrounding only a proximal portion of the implant when the implant is in a pre-deployed state; wherein at least one of the first expandable portion and the second expandable portion is self-expanding; wherein the implant can be configured such that the first expandable portion is expanded before the second expandable portion is expanded; and/or any features, components, and/or details of any implant embodiments disclosed herein.

Disclosed herein are additional embodiments of closure or occlusion devices for an cavity, including an implant that is selectively expandable from a first state to a second state and a cover coupled with the implant, wherein the implant can be configured to be expanded against a wall of an opening of the cavity when the implant is in the second state, wherein a size of the implant is greater in the second state than in the first state, wherein at least a portion of the cover is positioned adjacent to an outside surface of the implant and is selectively movable between at least a first state and a second state, wherein the cover can be configured to have a plurality of folds or wrinkles in a portion of the cover adjacent to the outside surface of the implant when the cover is in the second state, and wherein the implant can be configured to block an opening of the cavity when the implant is in the second state.

Any embodiments of the devices disclosed herein can include, in additional embodiments, one or more of the following features, components, and/or details, in any combination with any of the other features, components, and/or details of any other embodiments disclosed herein: wherein the cover can be configured such that at least one or more of the plurality of folds or wrinkles is positioned between the outside surface of at least a portion of the implant and at least a portion of the wall of the opening of the cavity when the implant and the cover are in the second state; further including a pull wire coupled with the cover and configured to move the cover from the first state to the second state upon withdrawal of the pull wire; and/or wherein the implant is also selectively contractible from the second state to the first state.

Any embodiments of the devices disclosed herein can include, in additional embodiments, one or more of the following features, components, and/or details, in any combination with any of the other features, components, and/or details of any other embodiments disclosed herein: wherein the device further includes a delivery catheter; wherein the device further includes an implant of any of the implant embodiments disclosed herein that is advanceable through the delivery catheter when the implant is in a first state; wherein the implant includes a first stage portion and a second stage portion that are each independently deployable to at least a second operable or deployed state; wherein the first stage portion is configured to be at least partially deployed before a second stage portion is deployed; wherein the first stage portion is configured to be positioned near a distal end portion of the cavity; wherein the second stage portion is configured to constrict an opening of the cavity when the second stage portion is in the second state; wherein second stage portion is configured to close the opening of the cavity when the second stage portion is in the second state; wherein second stage portion is configured to fold one or more tissue portions surrounding or adjacent to the opening of the cavity when the second stage portion is in the second state; wherein the second stage portion is configured to twist one or more portions of tissue surrounding the opening of the cavity to constrict or close the opening of the cavity when the second stage portion is in a second state; wherein the second stage portion comprises a means for constricting or closing the opening of the cavity; wherein the second stage portion comprises a hinge mechanism for constricting or closing the opening of the cavity; further including at least one of a passive activation mechanism and an active activation mechanism to activate the hinge mechanism; and/or wherein at least one of the first stage portion and the second stage portion is self-expanding.

Disclosed herein are embodiments of methods of constricting, occluding, closing, or otherwise treating a cavity (hereinafter collectively referred to treatment methods). Any embodiments of such methods can be used to deploy or implant any embodiments of the implants or devices disclosed herein. Any embodiments of the methods disclosed herein can include advancing a delivery catheter having an implant coupled therewith into the space outside of or adjacent to the cavity, advancing a distal tip of the delivery catheter near an opening of the cavity, and/or elongating the cavity in a first direction by at least expanding the implant in the first direction so that a ratio of a size of the opening of the cavity in the first direction relative to a size of the opening of the cavity in a second direction that is perpendicular to the first direction is at least 2 to 1. The method can also include withdrawing the delivery catheter with the implant positioned in the cavity.

Any embodiments of the methods disclosed herein can include, in additional embodiments, one or more of the following features, components, steps, and/or details, in any combination with any of the other features, components, steps, and/or details of any other embodiments disclosed herein: wherein activating a portion of the implant to reduce the size of the opening of the cavity adjacent to the opening of the cavity comprises folding a tissue surrounding the opening of the cavity so as to reduce a size of the opening of the cavity; wherein activating a portion of the implant to reduce the size of the opening of the cavity comprises folding a tissue surrounding the opening of the cavity to close the opening of the cavity; wherein activating a portion of the implant to reduce the size of the opening of the cavity comprises linearizing the opening of the cavity; wherein activating a portion of the implant to reduce the size of the opening of the cavity comprises stretching the opening of the cavity; twisting one or more portions of tissue surrounding the opening of the cavity to constrict or close the opening of the cavity when the second stage portion is in a second state; activating at least a portion of the implant to close the opening of the cavity after positioning the implant to achieve apposition in a first direction and/or a second direction; activating a means for folding a portion of tissue to fold a tissue surrounding the opening of the cavity to reduce a size of the opening of the cavity; activating a tissue folding mechanism of the implant to fold a tissue surrounding the opening of the cavity to close the opening of the cavity; reversing the tissue folding mechanism after evaluating the opening of the cavity and reactivating the tissue folding mechanism of the implant to fold a tissue surrounding the opening of the cavity to close the opening of the cavity; evaluating a position and/or an orientation of the implant, constricting at least a portion of the implant and repositioning at least a portion of the implant relative to the cavity; constricting the first stage portion of the implant after evaluating the position and/or the orientation of the implant, repositioning at least a portion of the implant relative to the cavity, and expanding the first stage portion of the implant to at least the partially expanded state; recapturing all or a portion of the implant and repositioning the implant; wherein expanding the distal portion of the implant to at least a partially expanded state comprises advancing the distal portion of the implant past the distal tip of the deployment catheter; and/or wherein at least the distal portion of the implant is self-expanding.

Disclosed herein are additional embodiments of treatment methods that include advancing a deployment device having an implant into the cavity, moving at least a portion of an outside surface of the implant or one or more tissue anchors extending away from an outer surface of the implant against an inner wall surface of the cavity, rotating the implant from a first rotational position to a second rotational position to twist the cavity, and preventing the implant from rotating back to the first rotational position. In any embodiments, the method can include moving at least a portion of an outside surface of the implant or one or more tissue anchors extending away from an outer surface of the implant against an inner wall surface of the cavity without changing a shape or size of the implant, and/or moving the implant from a first state to a second state, and wherein at least a portion of the implant is enlarged in a radial direction when the implant is in the second state as compared to the first state.

Additionally, any implant and/or device or system embodiments disclosed herein can be adapted and/or used for treatment of any tissue condition in a body that is desired to be occluded, restricted, or closed. For example and without limitation, some embodiments of the devices and systems for treating a tissue condition disclosed herein can include an implant comprising a contact member that can be (but is not required to be) configured to move between a first state and a second state and a securing element, wherein the contact member can be configured to move from the first state to the second state so that at least a portion of the contact member engages a wall portion of the tissue condition after the contact member has been advanced into the tissue condition, the contact member can be configured to rotate at least in a first direction from a first rotational position to a second rotational position, the contact member can be configured to twist at least a portion of the tissue of the tissue condition in the first direction when the contact member is rotated from the first rotational position to the second rotational position, and/or the securing element can be configured to prevent a rotation of at least a portion of the tissue of the tissue condition in a second direction when the securing element is in an operable state, wherein the second direction is opposite to the first direction. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include an implant having a contact member that can be (but is not required to be) configured to move between a first state and a second state, a catheter configured to advance the contact member into the tissue condition when the contact member is in the first state and to cause the contact member to move from the first state to the second state so that an outside surface of the contact member engages at least one wall surface of the tissue condition after the contact member has been advanced into or adjacent to the tissue condition, wherein the catheter is configured to exert a torque on the contact member when at least a portion of the catheter is rotated until a predetermine torque level is reached to rotate the contact member from a first rotational position to a second rotational position so that the contact member can twist at least a portion of the tissue condition. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include a method of treating a tissue condition, comprising advancing a deployment device having an implant into or adjacent to the tissue condition, wherein the implant can be (but is not required to be) configured to be moved from a first state to a second state, and wherein at least a portion of the implant can be enlarged in a radial direction when the implant is in the second state as compared to the first state, moving the implant from the first state to the second state within the tissue condition so as to move at least a portion of an outside surface of the implant or one or more tissue anchors extending away from an outer surface of the implant against at least one wall surface of the tissue condition, rotating the implant from a first rotational position to a second rotational position to twist the tissue condition, and/or preventing the implant from rotating back to the first rotational position.

Additionally, any implant and/or device or system embodiments disclosed herein can be adapted and/or used for treatment of any tissue condition in a body that is desired to be occluded, reshaped, restricted, or closed. For example and without limitation, some embodiments of the devices and systems for treating a tissue condition disclosed herein can include an implant comprising a contact member that is configured to engage a wall portion of the tissue condition after the contact member has been advanced into the tissue condition, the contact member can be configured to rotate at least in a first direction from a first rotational position to a second rotational position, the contact member can be configured to twist at least a portion of the tissue of the tissue condition in the first direction when the contact member is rotated from the first rotational position to the second rotational position, and/or the securing element can be configured to prevent a rotation of at least a portion of the tissue of the tissue condition in a second direction when the securing element is in an operable state, wherein the second direction is opposite to the first direction. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include an implant having a contact member, a catheter configured to advance the contact member into the tissue condition so that the contact member engages at least one wall surface of the tissue condition after the contact member has been advanced into or adjacent to the tissue condition, wherein the catheter is configured to exert a torque on the contact member when at least a portion of the catheter is rotated until a predetermine torque level is reached to rotate the contact member from a first rotational position to a second rotational position so that the contact member can twist at least a portion of the tissue condition. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include a method of treating a tissue condition, comprising advancing a deployment device having an implant into or adjacent to the tissue condition, and wherein at least a portion of the implant engages a wall surface of the tissue condition, rotating the implant from a first rotational position to a second rotational position to twist the tissue condition, and/or preventing the implant from rotating back to the first rotational position.

Disclosed herein are embodiments of methods for reshaping, closing or occluding a cavity or tissue defect in a body, that can include rotating the cavity or tissue defect in a body, and securing the cavity or tissue defect in a body in a rotated position. Any embodiments of the methods and/or devices disclosed herein for reshaping, closing or occluding a cavity or tissue defect in the body disclosed herein can, in additional embodiments, include one or more of the following steps, features, or details, in any combination: wherein rotating the cavity or tissue defect in the body can include rotating the cavity or tissue defect in the body to deform or occlude the cavity or tissue defect in the body; wherein securing the cavity or tissue defect in the body in a rotated position can include securing the cavity or tissue defect in a rotated position in which the cavity or tissue defect is reduced in volume; wherein securing the cavity or tissue defect in a rotated position can include securing the cavity or tissue defect in a rotated position in which the cavity or tissue defect is deformed or occluded; wherein securing the cavity or tissue defect in a position in which the cavity or tissue defect is deformed or occluded can include eliminating or substantially eliminating a blood volume of the cavity or tissue defect; wherein rotating the cavity or tissue defect can include bending or contorting the cavity or tissue defect; wherein securing the cavity or tissue defect in a rotated position can include securing the cavity or tissue defect in a position in which a blood communication between the cavity or tissue defect and a left atrium is inhibited; wherein securing the cavity or tissue defect in a rotated position can include eliminating or substantially eliminating a communication of blood or other matter between the cavity or tissue defect and the left atrium; wherein rotating the cavity or tissue defect can include engaging a wall portion on an inside of the cavity or tissue defect and/or an opening of the cavity or tissue defect with a contact member and rotating the contact member; wherein the contact member is a balloon; wherein the contact member is positioned on an implant coupled to the delivery system; wherein the implant is self-expanding, balloon expandable and/or mechanically expanded; wherein rotating the cavity or tissue defect can include engaging a wall portion on an inside of the cavity or tissue defect with one or more tissue holding features; wherein the one or more tissue holding features can include one or more tissue anchors or one or more tissue grippers; wherein rotating the cavity or tissue defect can include advancing a device into the cavity or tissue defect; further including rotating a component of the device to rotate the cavity or tissue defect; wherein rotating the device can include rotating the device at least approximately 90 degrees in either direction from an initial position; wherein rotating the device can include rotating the device at least approximately 180 degrees in either direction from an initial position; and/or wherein rotating the device can include rotating the device from approximately 90 degrees to approximately 360 degrees in either direction from an initial position.

Any embodiments of the methods and/or devices disclosed herein for reshaping, closing or occluding a cavity or tissue defect in the body disclosed herein can, in additional embodiments, include one or more of the following steps, features, or details, in any combination: wherein rotating the device rotates the component of the device to twist the cavity or tissue defect;

wherein rotating the cavity or tissue defect can include rotating a portion of the cavity or tissue defect about an axis to twist the cavity or tissue defect; wherein rotating a portion of the cavity or tissue defect about one or more axes from an initial position can include rotating the portion of the cavity or tissue defect at least approximately 90 degrees in either direction from the initial position;

wherein rotating a portion of the cavity or tissue defect about one or more axes from an initial position can include rotating the portion of the cavity or tissue defect at least approximately 180 degrees in either direction from the initial position; wherein rotating a portion of the cavity or tissue defect about one or more axes from an initial position can include rotating the portion of the cavity or tissue defect from approximately 90 degrees to approximately 360 degrees in either direction from the initial position; wherein rotating a portion of the cavity or tissue defect can include rotating the cavity or tissue defect until an opening of the cavity or tissue defect is substantially or completely closed; wherein rotating a portion of the cavity or tissue defect can include rotating the cavity or tissue defect until a blood communication between the cavity or tissue defect and a left atrium is inhibited; wherein rotating a portion of the cavity or tissue defect can include rotating the cavity or tissue defect until a communication of blood or other matter between the cavity or tissue defect and the left atrium is eliminated or substantially eliminated;

wherein securing the cavity or tissue defect in a rotated position can include engaging tissue of the body that has been twisted; wherein engaging tissue of the body that has been twisted can include engaging tissue wall with an anchor element or gripping element; wherein the anchor element can include a suture or a staple; wherein securing the cavity or tissue defect in a rotated position can include securing a tissue of the body outside of an occluded portion of the cavity or tissue defect with an anchor element; wherein securing the cavity or tissue defect in a rotated position can include securing a tissue of an occluded portion of the cavity or tissue defect with an anchor element; wherein the anchor element can include a plurality of tissue grippers on at least one surface thereof configured to engage with the internal wall of the body outside of the cavity or tissue defect; and/or wherein the cavity is a mitral valve or commissure of the mitral valve.

Also disclosed herein are embodiments of a method of reducing an opening of a cavity or tissue defect in a body, including: twisting tissue of the body to constrict the opening of the cavity or tissue defect in a body, and securing tissue that has deformed or constricted as a result of twisting tissue of the body. Any embodiments of the methods and/or devices disclosed herein for reshaping, closing or occluding a cavity or tissue defect in the body disclosed herein can, in additional embodiments, include one or more of the following steps, features, or details, in any combination: wherein securing the tissue that has deformed or constricted can include advancing a securing element into the tissue that has deformed or constricted as a result of twisting tissue of the body; wherein the securing element can include a tissue anchor or tissue gripper; wherein securing the tissue that has deformed or constricted as a result of twisting tissue of the body can include advancing a securing element into the tissue that has deformed or constricted to compress the tissue that has deformed or constricted; and/or wherein securing tissue that has deformed or constricted as a result of twisting tissue of the body can include advancing one or more sutures or one or more staples into the tissue that has deformed or constricted as a result of twisting tissue of the body.

Also disclosed herein are embodiments of a method of treating a cavity or tissue defect in a body, that can include twisting the cavity or tissue defect in a body such that the cavity or tissue defect in a body becomes reduced in volume, and securing the cavity or tissue defect in a body in a reduced volume configuration. Any embodiments of the methods and/or devices disclosed herein for reshaping, closing or occluding a cavity or tissue defect in the body disclosed herein can, in additional embodiments, include one or more of the following steps, features, or details, in any combination: wherein securing the cavity or tissue defect in the body in a reduced volume configuration can include occluding the cavity or tissue defect in the body with an implant that is smaller in size than a size of the inside of the cavity or tissue defect in the body; and/or further including unsecuring and untwisting the cavity or tissue defect in a body.

BRIEF DESCRIPTION OF THE DRAWINGS

FIG. 22A shows a side view of another embodiment of a treatment system wherein the contact member is in a second, expanded state and the retention member is in a first, retracted state.

FIG. 22B shows a side view of the treatment system of FIG. 22A wherein the contact member is in the second state and the retention member is in a second, deployed state.

FIGS. 24-35 illustrate an embodiment of a deployment method for the embodiment of the treatment system illustrated in FIG. 22A.

FIGS. 47A-47F show another embodiment of a treatment system for closing or occluding a cavity.

FIGS. 49A-49G show another embodiment of a treatment system for closing or occluding a cavity.

FIGS. 56A-56B show another embodiment of a contact member that can be used with any treatment system embodiments disclosed herein.

FIGS. 57A-57B show another embodiment of a securing element that can be used with any treatment system embodiments disclosed herein.

FIGS. 64A-64D show another embodiment of a device and an embodiment of a method for using such device for treating the cavity.

DETAILED DESCRIPTION OF SOME EXEMPLIFYING EMBODIMENTS

Figure 1A:
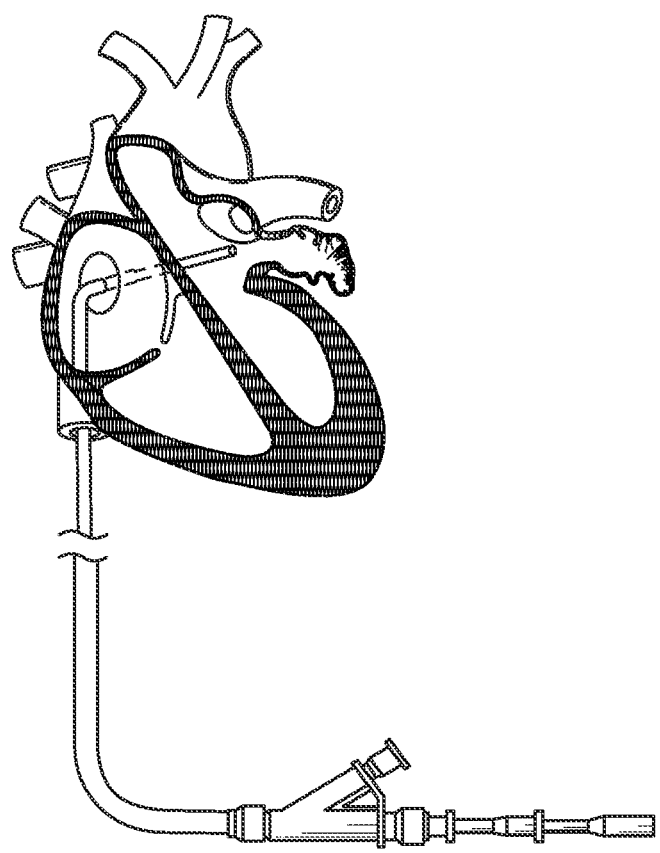
FIG. 1A illustrates a path through the venous system via femoral vein and a transseptal puncture into a space outside of a target cavity within the heart, e.g., a left atrium, that can be used to access a cavity in the heart.

Described herein are novel devices, systems, and methods for closing or occluding a cavity in the body. The term cavity, as used herein, refers to an opening, hole, cut, slit, wound, wound cavity, vessel, passageway, chamber, heart chamber, tissue void, or other space within the body. Additionally, any references herein or incorporated by reference herein to a left atrial appendage or LAA are meant to also refer to any cavity in the body such that any description of a device used for the left atrial appendage or LAA or a method of treating a left atrial appendage or LAA is meant to include a device for treating any cavity in the body or a method of treating any cavity in the body. Some embodiments comprise a method that includes advancing a delivery system to the cavity, advancing and deploying an expandable element (which can be, in some embodiments, covered with barbs, texture, or other tissue engaging features or, alternatively, can be smooth) and which can have a generally spherical or orb shaped shape into the cavity, allowing the expandable element to engage distally and/or radially with inner wall surfaces of the cavity, applying a rotation to the inner catheter member connected to the expandable element to twist the cavity to close and/or occlude the cavity at or near the opening of the cavity. By occluding the cavity, some embodiments disclosed herein can effectively eliminate or significantly or nearly completely eliminate a communication of blood or other matter between the cavity and the space adjacent to or outside of the cavity. Any methods of deployment disclosed herein can also include deployment of a securing element (which is also referred to herein as a locking element or anchoring element) that is configured to inhibit or prevent the unwinding of the expandable element relative to the cavity and the tissue adjacent to the cavity and/or in the space adjacent to the cavity, thereby inhibiting or preventing the untwisting of the cavity.

The devices, systems, and methods disclosed herein can be used, or can be adapted, for other applications within the body or on the surface of the body of any human, animal, reptile, or other living being. Other applications include, without limitation, closing openings in other tissues aside from the cavity, occluding or closing openings, passageways, and/or chambers within the heart or other organs, occluding or closing holes or other slits or openings in vessels and passageways, and/or treating other conditions.

The clinical benefit of some embodiments is a resultant implant which is not in direct blood contact with the blood or flow outside of or adjacent to the cavity except a possible portion of the securing feature. The securing element of any embodiments can be configured to limit the exposure of the securing element to the blood within the space adjacent to or outside of the cavity (i.e., to limit the amount of the securing element that projects into the space adjacent to or outside of the cavity). In some embodiments, the entire implant can be surrounded by tissue of the cavity tissue so that no portion, or only a minimal portion (for example, less than 10% of the surface area, or less than 40% of the surface area) of the implant is exposed to blood flow within the space adjacent to or outside of the cavity. This can have clinical benefits to the patient as there should be post drug regiment required. Any of the devices used in any of the methods described here may be advanced under any of a variety of visualization techniques, e.g., fluoroscopic visualization, ultrasound, etc.

The implant of any embodiments disclosed herein can have an expandable atraumatic shape with tissue gripping features located on the outer edges of the shape, coupled to a securing and or ratcheting feature which can hold the initial or final closed position of the implant. The implant of any embodiments disclosed herein can be configured to grip the internal tissue of the cavity with radial force as well. In some embodiments a vacuum or suction can be provided by the catheter or any component thereof to draw a tissue portion of the cavity or atrium toward the implant. The implant of any embodiments disclosed herein can have an atraumatic shape that can be spherical, dome shaped, or comprise a coil of wire in the shape of a disk, can have expanded cut pattern in the shape of a stent, or anything else which can have rounded edges. In some embodiments, the barbs (which can be tissue anchors) on the outer edges or surface of the implant can comprise metal hooks, plastic cleats, rough texture of some material or surface features, a coating or activated adhesive which grips the inside surface of the cavity. Additionally, in any embodiments disclosed herein, the tissue anchors can be positioned on or adjacent to an end portion of the implant to engage with an end portion of the cavity. In any embodiments, the barbs can be directional allowing for tissue engagement in one rotational direction and a disengagement in the opposite rotational direction for a possible repositioning, resizing, or removal from the cavity.

The rotation used to twist closed or occluded (completely or substantially) the cavity for any embodiments disclosed herein may be as little as a quarter of a turn (i.e., revolution), a half turn, a complete turn, up to as much as multiple turns for deeper or longer cavities. The securing feature or element (also referred to herein as an anchoring element) in any embodiments disclosed herein can have a single arm or multiple arms which can be connected to the implant body that is positioned and rotated within the closed or substantially closed cavity. The securing feature or element can also be configured to engage tissue adjacent to the opening of the cavity. In any embodiments, the securing element can have multiple arms or members, can have an annular ring, can have a disk, or any other suitable shaped surface anchor configured to couple non-twisted tissue to the twisted implant. In some embodiments, the securing element can also have a small diameter ring which can be configured to clamp to or engage with the tissue which connects to the center hub of the implant (adjacent to the ostium of the cavity) or it can also have a clip which folds and clips the implant to the side of the wall of the space adjacent to or outside of the cavity.

In some embodiments disclosed herein, the device can be configured to restrict an opening of the cavity by reducing a cross-sectional area of the opening of the cavity by at least 95%, or by at least 90%, or by from at least approximately 80% to approximately 100% as compared to a cross-sectional area of the opening of the cavity before the device was implanted (including a blockage effect from the device). Further, in some embodiments, the method can include rotating the implant from the first rotational position to the second rotational position to twist the cavity until an opening of the cavity is at least 95% blocked and/or restricted, or at least 90% blocked and/or restricted, or at least 80% blocked and/or restricted, or from approximately 70% blocked and/or restricted to approximately 100% blocked and/or restricted. Additionally, any embodiments disclosed herein can include implanting two or more implants of any of the implant embodiments disclosed herein in the cavity. For example and without limitation, any of the implant embodiments disclosed herein can be configured to be deployed or implanted in the cavity to improve the occlusion of implants already implanted in the cavity, including any implants that fit within any of the foregoing ranges of less than complete occlusion. In some embodiments, one or more additional implants or devices can be implanted adjacent to, over, around, or otherwise with an existing implant to improve a level of occlusion of the cavity.

Alternatively, in any embodiments disclosed herein, the securing element can be configured to merely compress the tissue of the space outside of or adjacent to the cavity, of the opening of the cavity, and/or the cavity that has constricted around an outer surface of a body portion of the implant between a distal surface of the securing element and the contact member to prevent rotation of the implant in the second direction, i.e., after the contact member has been rotated to the second rotational position, without penetrating into such tissue. For example and without limitation, in any embodiments disclosed herein, the securing element can have a body portion that is smooth an nonobtrusive or nonpenetrating, e.g., so that the securing element does not have any tissue penetrating features on it that extend toward the tissue surfaces. In other embodiments, the arms (or, at least, the portions of the arms that extend in the axial direction when the securing element is in the second state) or other tissue penetrating portions of the securing element can be short, such as from approximately 1 mm to approximately 5 mm in length, or from approximately 1 mm to approximately 3 mm in length, or from approximately 1 mm to approximately 2 mm in length, or of any values or ranges of values between any of the foregoing ranges.

Figure 1B:
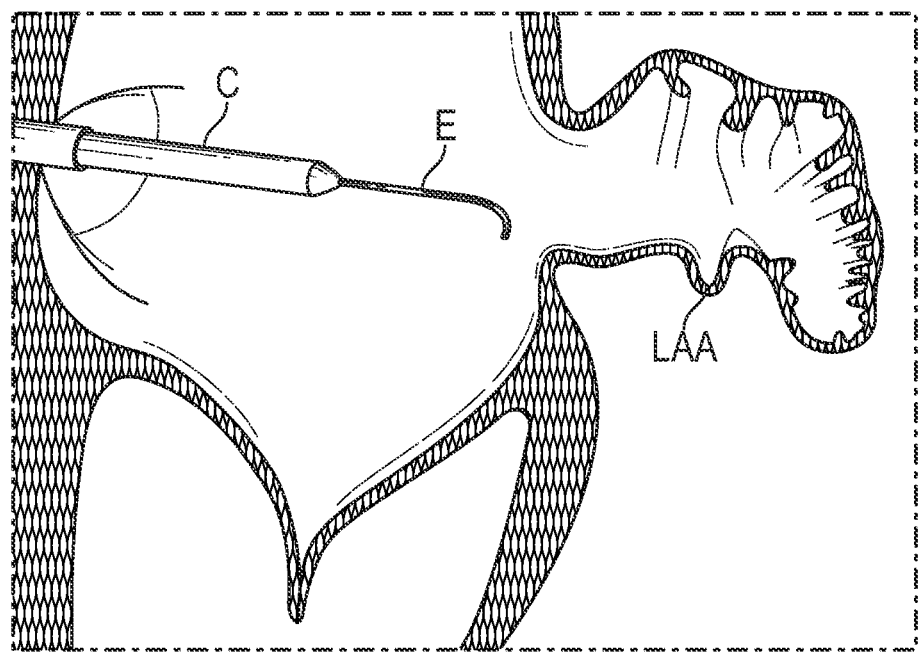
FIG. 1B shows a section view of a space outside of a target cavity within the heart, e.g., a left atrium, showing a guidewire advancing toward the cavity.
Figure 2A:
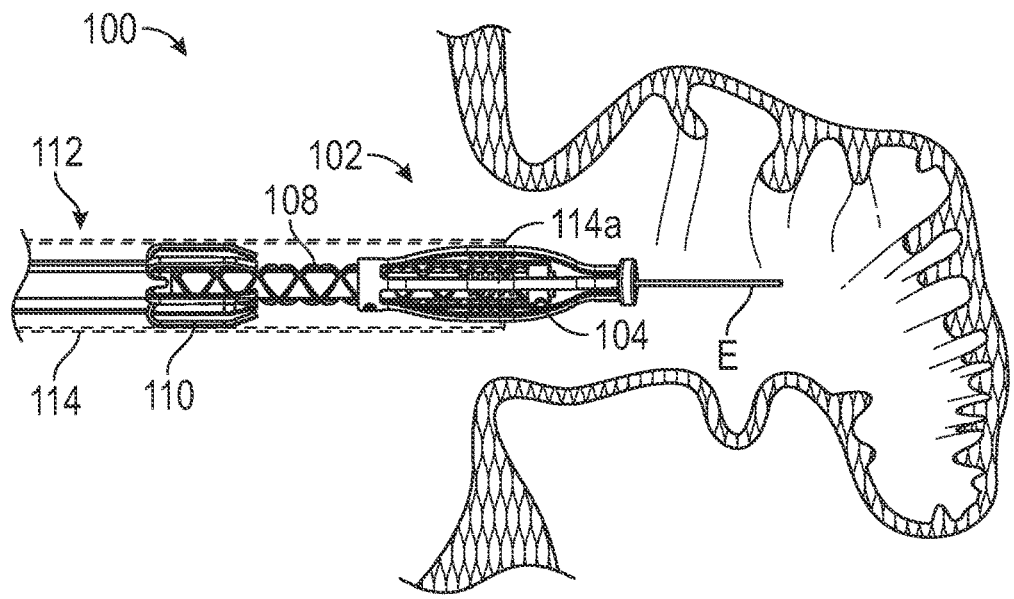
FIG. 2A shows an embodiment of treatment system having an implant device being advanced through a catheter into the cavity, the implant device being in a collapsed state and restrained within an outer tube of the catheter.

FIGS. 1A and 1B show a section view of a space outside of or adjacent to a cavity, showing a guidewire G advancing from a catheter C toward the cavity. FIG. 2A shows an embodiment of an occlusion system 100 for occluding or closing the opening of the cavity. In any embodiments disclosed herein, the occlusion system (including the embodiment of the occlusion system 100) can be configured to rotate and twist the cavity so as to cause a neck or a portion of the cavity adjacent to the opening of the cavity to constrict and substantially or fully close about an outside surface of a portion of the implant device, thereby causing the opening of the cavity to be occluded. In any embodiments of the occlusion system, including the embodiment of the occlusion system 100, the system can have an implant device 102 having a contact member 104 (also referred to herein as a contact element or an expandable implant member), a securing element or securing element 110 (also referred to as a securing member), and a retention member 108. The implant device 102 can be configured to be advanced through a catheter 112 into the cavity. The embodiment of the implant device 102 shown in FIG. 2A is shown in a collapsed state and restrained within an outer sleeve 114 of the catheter 112. As shown, the implant device 102 can be advanced distally out of the catheter 112 past a distal end 114a of the outer sleeve 114 by advancing a portion of or member of the catheter, such as without limitation a core member 113 of the catheter 112, so that the contact member 104 of the implant device 102 can be advanced into the cavity and/or deployed within the cavity.

Figure 2B:
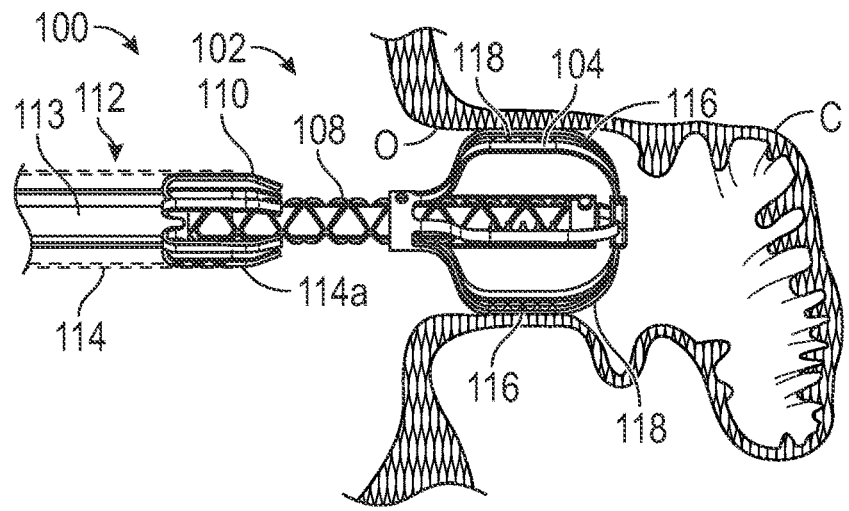
FIG. 2B shows the embodiment of the treatment system of FIG. 2A, showing the contact member being expanded within the cavity.

Alternatively, the catheter 112 having the implant device 102 therein can be advanced into a desired position within the cavity and, while holding the implant device 102 in a stationary axial position by maintaining the core member 113 of the catheter 112 in a stationary axial position, the outer sleeve 114 of the catheter 112 can be retracted or withdrawn so as to expose and/or unrestrain the contact member 104 of the implant device 102. In any embodiments disclosed herein, the contact member 104 can be self-expanding in a radial direction so that, when a restraint is removed from the contact member 104, the contact member 104 can expand against an inner surface or wall of the cavity automatically. In other embodiments, the contact member 104 can be mechanically expandable, such as by a balloon expander, so as to expand against inside surface or wall of the cavity. FIG. 2B illustrates the contact number 104 after it has been expanded against an inside wall of the cavity distal to an opening O of the cavity.

Alternatively, in any embodiments disclosed herein, the contact member can be configured to remain in a first state within the catheter, during the entire treatment procedure, and/or thereafter. For example and without limitation, in any embodiments disclosed herein, the contact member can be configured such that the contact member is deployed from the catheter and advanced into contact with a tissue surface of an inside wall of the cavity, engage the tissue surface of the inside wall of the cavity, and cause the cavity to twist when a torque and/or rotation is applied to the contact member, all without changing the state of the contact member. Alternatively, in any embodiments disclosed herein, the contact member can be configured to be advanced into the cavity, to engage an inside surface of the cavity, and to and cause the cavity to twist when a torque and/or rotation is applied to the contact member. In any embodiments disclosed herein, the contact member and/or any other component of the device can be configured to be removed from the cavity (which can, as stated above, include the wound cavity), before the procedure is completed so that no portion of the device remains in the cavity after the procedure is finalized.

In any embodiments disclosed herein, including the embodiment illustrated in FIG. 2B, the contact member 104 can have a plurality of arms or struts 116 that are each configured to self-expand in a radial direction when a restraint has been removed from an outside surface of the contact member 104. For example without limitation, any embodiments of the contact member disclosed herein can have six struts 116, or between six and ten struts, or from less than six to more than ten struts.

Further, in any embodiments, the contact member 104 can have a plurality of teeth, cleats, barbs, nubs, texture, studs, anchors or other tissue engaging features 118 or other similar features configured to penetrate or engage the tissue of the cavity that are configured to penetrate into a tissue within the cavity when the contact member 104 is expanded against the tissue of the cavity and/or when the contact member 104 is rotated or twisted within the cavity. Note that teeth, cleats, barbs, nubs, texture, studs, anchors and other tissue engaging features or features configured to grip or engage the tissue when torque is applied to the expanded contact member will be collectively referred to herein as tissue anchors, which use of this term is meant to describe and include any of the foregoing features individually and/or any combination of these features.

The tissue anchors 118 can be integrally formed with the struts, on the struts, added to the struts, or otherwise coupled with or supported by the struts. The tissue anchors 118 can be circumferentially facing (as shown, can be radially facing so as to penetrate or engage the tissue at an orthogonal angle relative to the tissue surface of the cavity, at an angle relative to the line that is tangential to the outer surface of the contact member 104, or otherwise. In some embodiments, each strut 116 can support a plurality of tapered tissue anchors facing in a circumferential direction, as illustrated in FIG. 2B. All of the tissue anchors can face in a similar orientation relative to each of the struts, such as in the circumferential direction relative to each strut. In the illustrated embodiment, each strut 104 has five tissue anchors 118. In this embodiment, when the contact member 104 is rotated in a first direction (indicated by arrow A1 in FIG. 2C, which can be in the clockwise or the counterclockwise direction), one or more or all of the struts 116 and one or more or all of the tissue anchors 118 can engage the tissue of the cavity and cause the cavity to twist or rotate in the first direction A1. The twisting or rotation of the cavity in the first direction from a first rotational position to a second rotational position results in the opening O of the cavity constricting in a radial direction (represented or identified by arrows A2 in FIG. 2C) so that the opening O of the cavity is caused to move or constrict around an outside surface of a proximal portion 104a of the contact member 104. An operator can twist or rotate the contact member 104 by twisting or rotating the core member 113 of the catheter 112. The tightening or constriction of the opening O of the cavity around an outside surface of the proximal portion 104a of the contact member 104 or other portion of the implant device can result in the occlusion, or substantial occlusion, or substantial closing off of the interior portion of the cavity from the space outside of the cavity, thereby substantially reducing the health risks associated with an open cavity.

In some embodiments, as in the illustrated embodiment, the securing element 110 can be maintained in a collapsed or first state such as by being restrained by the outer sleeve 114 of the catheter 112 while the contact member 104 is being deployed and rotated to prevent the securing element 110 from contacting tissue within the space outside of the cavity or within the cavity and potentially lacerating or otherwise damaging such tissue. An intermediary sleeve or tube 115 can be coupled with the securing element 110 and can be used to manipulate and control a position and/or an orientation of the securing element 110, including holding a proximal end portion 110a of the securing element in a fixed axial position while a distally directed force is exerted on the contact member 104 to maintain the retention member in the first, extended state. In any implant device embodiments disclosed herein, the securing element (including, for example and without limitation, securing element 110) can be keyed, indexed, or otherwise rotationally fixed to the contact member (including, for example and without limitation, contact member 104) so that the securing element cannot rotate relative to the contact member and the contact member cannot rotate relative to the securing element. In this configuration, the securing element can prevent or substantially prevent or inhibit the contact member and the cavity from rotating back toward the first rotational position.

Figure 2C:
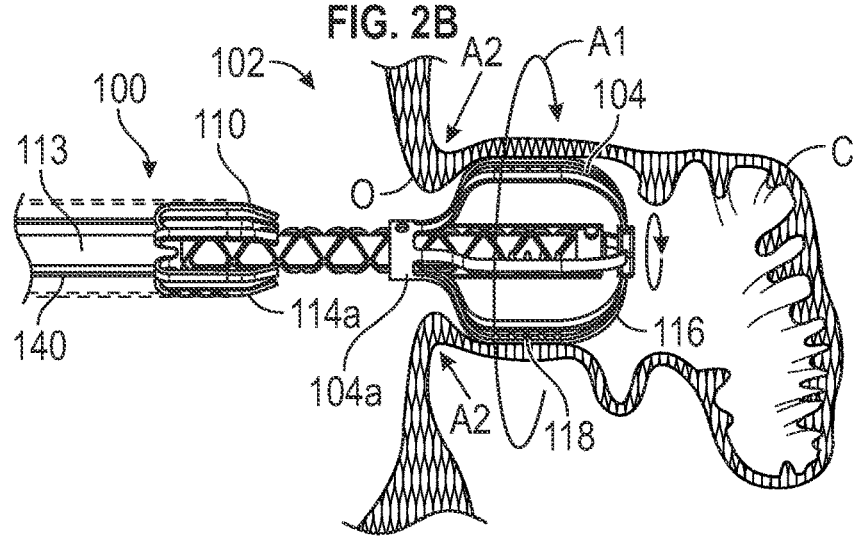
FIG. 2C shows the embodiment of the treatment system of FIG. 2A, showing the contact member being rotated to twist the cavity and cause a neck or opening of the cavity to constrict around a portion of the implant device.
Figure 2D:
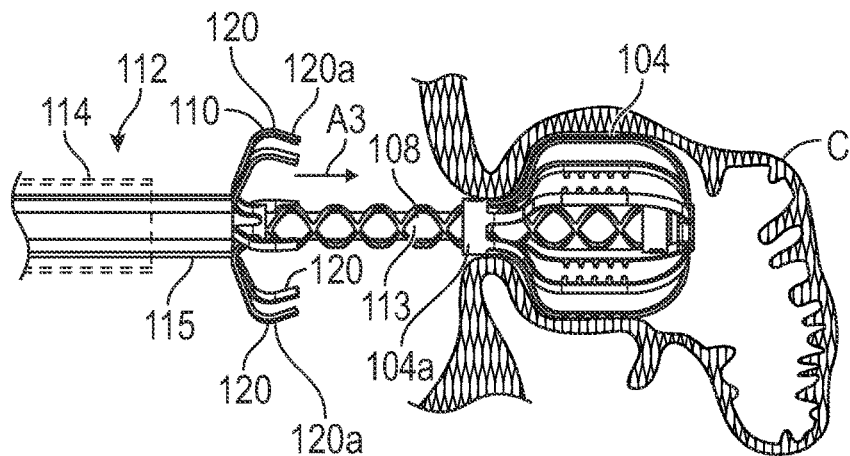
FIG. 2D shows the embodiment of the treatment system of FIG. 2A, showing the securing element of the embodiment of the implant device being advanced toward the contact member of the implant device.
Figure 2E:
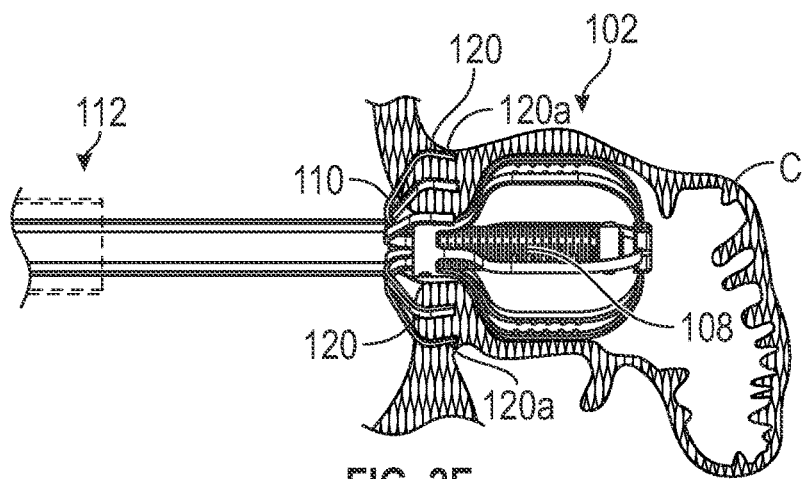
FIG. 2E shows the securing element of the treatment system of FIG. 2A engaged with the patient's tissue surrounding the proximal portion of the contact member of the implant device.
Figure 2F:
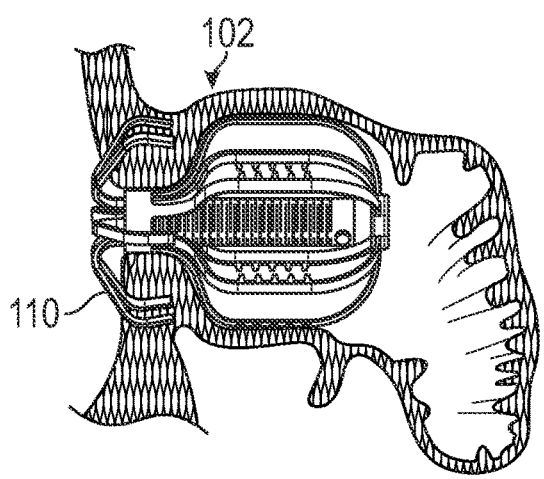
FIG. 2F shows the implant device of FIG. 2A disengaged and removed from the catheter.

With reference to FIG. 2D, with the contact member 104 having been rotated to the second rotational position and maintained in the second rotational position such that the opening O of the cavity remains constricted around a proximal portion 104a of the contact member 104 or other portion of the implant device and the cavity is generally occluded from the space outside of or adjacent to the cavity, the catheter tube member 115 can then be advanced in a distal direction (represented by arrow A3 as shown in FIG. 2D) or the outer sleeve 114 can be withdrawn in a proximal direction so that the securing element of 110 can be exposed so that it can self-expand from a first, collapsed state (as shown in FIG. 2C) to a second, expanded or open state (as shown in FIG. 2D). In the second state, a plurality of struts or members 120 of the securing element 110 can expand in a generally radial direction so as to open up to a larger overall diameter or profile. Additionally, because each of the one or more members 120 of the securing element 110 can have end portions 120a that extend in a generally distal axial direction (but can be slightly angled inwardly), as the securing element 110 is advanced in the axial direction, the distal portions 120a of each of the one or more members 120 can penetrate into and/or engage with a tissue portion of the space outside of or adjacent to the cavity, which can be within the heart or within any other organ or portion of the body, as shown in FIG. 2E. The tissue portion that the one or more members 120 can penetrate into or engage with can include portions of the tissue comprising the space outside of or adjacent to the cavity, the tissue of the opening of the cavity, and/or portions of the tissue comprising the cavity. As mentioned above, the contact member 104 can be held in generally a stationary axial position using the core member 113 while the securing element 110 is advanced distally toward the contact member 104. The retention member 108 can thereafter be unrestrained so that it can maintain the securing element 110 in the second position wherein the securing element 110 is engaged with the tissue of the space outside of or adjacent to the cavity, as shown in FIG. 2E. In some embodiments, the securing element can be biased toward a smaller size in the axial direction, such as with a spring member or similar. For example, the retention member 108 can be formed by laser cutting openings within a cylindrical tube, such as a hypo tube made of an elastic material, such as Nitinol. Thereafter, with reference to FIG. 2F, the implant device 102 can be disengaged from the catheter 112 and the catheter 112 can be retracted and removed from the patient's body. With the securing element 110 engaged with the patient's tissue, as illustrated in FIG. 2F, the cavity is prevented from rotating to the first rotational position, which is the untwisted or relaxed position. In this configuration, the implant device 102 can secure and maintain the cavity in a substantially or completely occluded or substantially or completely closed state.

The retention member 108 can thereafter be unrestrained (for example, released) so that it can retract, to maintain the securing element 110 in the second position wherein the securing element 110 is engaged with the tissue of the space outside of or adjacent to the cavity, as shown in FIG. 2E. In some embodiments, the securing retention member 108 can be biased toward a smaller size length or size in the axial direction, such as with a spring member or similar. For example, the retention member 108 can be formed by laser cutting openings within a cylindrical tube, such as a hypo tube made of an elastic material, such as Nitinol.

Thereafter, with reference to FIG. 2F, the implant device 102 can be disengaged from the catheter 112 and the catheter 112 can be retracted and removed from the patient's body. With the securing element 110 engaged with the patient's tissue, as illustrated in FIG. 2F, the cavity is prevented or, at least, inhibited or biased from rotating to the first rotational position, which is the untwisted or relaxed position. In this configuration, the implant device 102 can secure and maintain the cavity in a substantially or completely occluded or substantially or completely closed state.

Any of the components of any of the implant embodiments disclosed herein can be made from Nitinol or any other elastic or super elastic material, including any other shape memory materials, or any mechanically expandable material such as stainless steel or otherwise. In any embodiments disclosed herein, the contact member (such as contact member 104) can have a spherical, cylindrical, or other shape, such as the shape of an elongated bullet, a stent, a mushroom, or other non-round or non-cylindrical shape or any of the shapes described or shown with respect to any of the embodiments disclosed herein. In any embodiments disclosed herein, the contact member may comprise a series of interconnected struts (that can, but are not required to, form a diamond shaped pattern across all or a portion of the surface of the contact member), or may be made from a series of ribs or paddles which form the expandable device.

Figure 3:
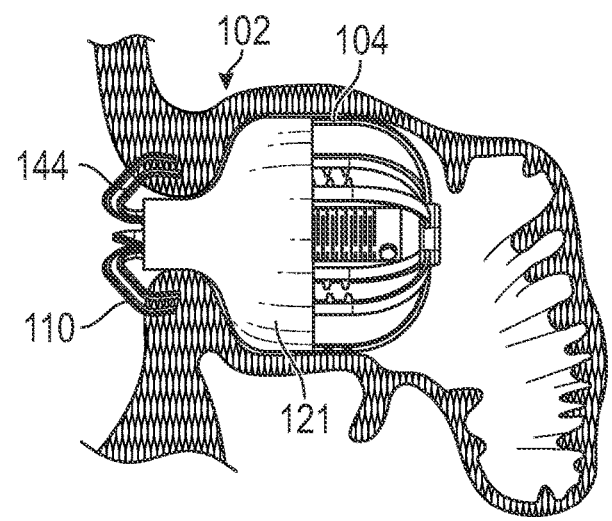
FIG. 3 shows an embodiment of an implant device having a cover member surrounding at least a portion of the implant device.

With reference to FIG. 3, the securing element of any device embodiments disclosed herein, including without limitation the securing element 110, can have an outer size (such as an outer diameter of the arms 144 of the securing element) that is significantly smaller than an outer size (such as an outer diameter) of the contact member 104. For example and without limitation, the securing element of any device embodiments disclosed herein can have an outer size that is approximately one-half of an outer size of the contact member 104, or from approximately 30% to approximately 80% of an outer size of the contact member 104, or from approximately 50% to approximately 60% of an outer size of the contact member 104. In any embodiments, the outer size of the securing element can be similar to or approximately the same as, or even larger than, the outer size of the contact member 104.

As also shown in FIG. 3, any embodiments of the implant device 102 disclosed herein can also have a cover member 121 that can provide an additional seal or barrier around an outside surface of the contact member 104 and/other portions of the implant device 102 to provide an additional barrier to the implant device 102. In some embodiments, the cover can be located or positioned on or against an inside surface or portion of the contact member of the implant. This can improve the seal or occlusion that the implant device 102 creates in the cavity. In some embodiments, the cover member 121 can cover substantially or completely all of the contact member 102 of the implant device.

Figure 4:
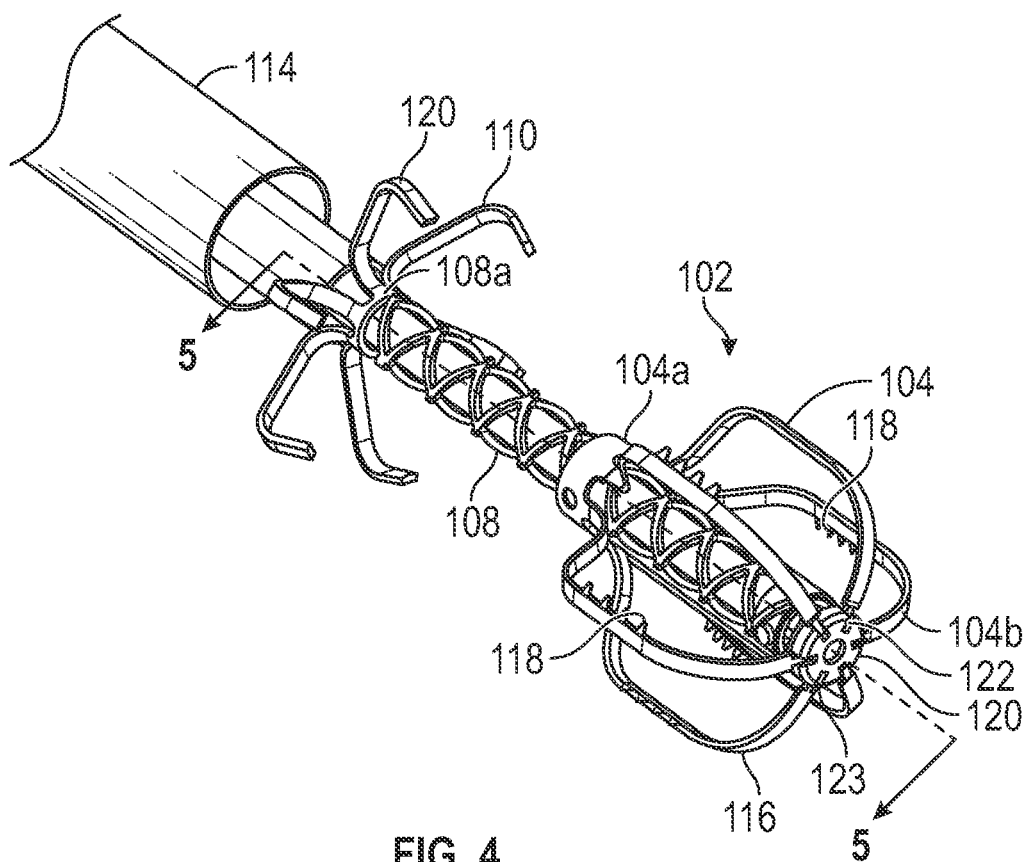
FIG. 4 shows the implant device of FIG. 2A wherein the contact member is in a second, expanded state, the retention member is in a first, extended state, and the securing element is in a second, open state.
Figure 5:
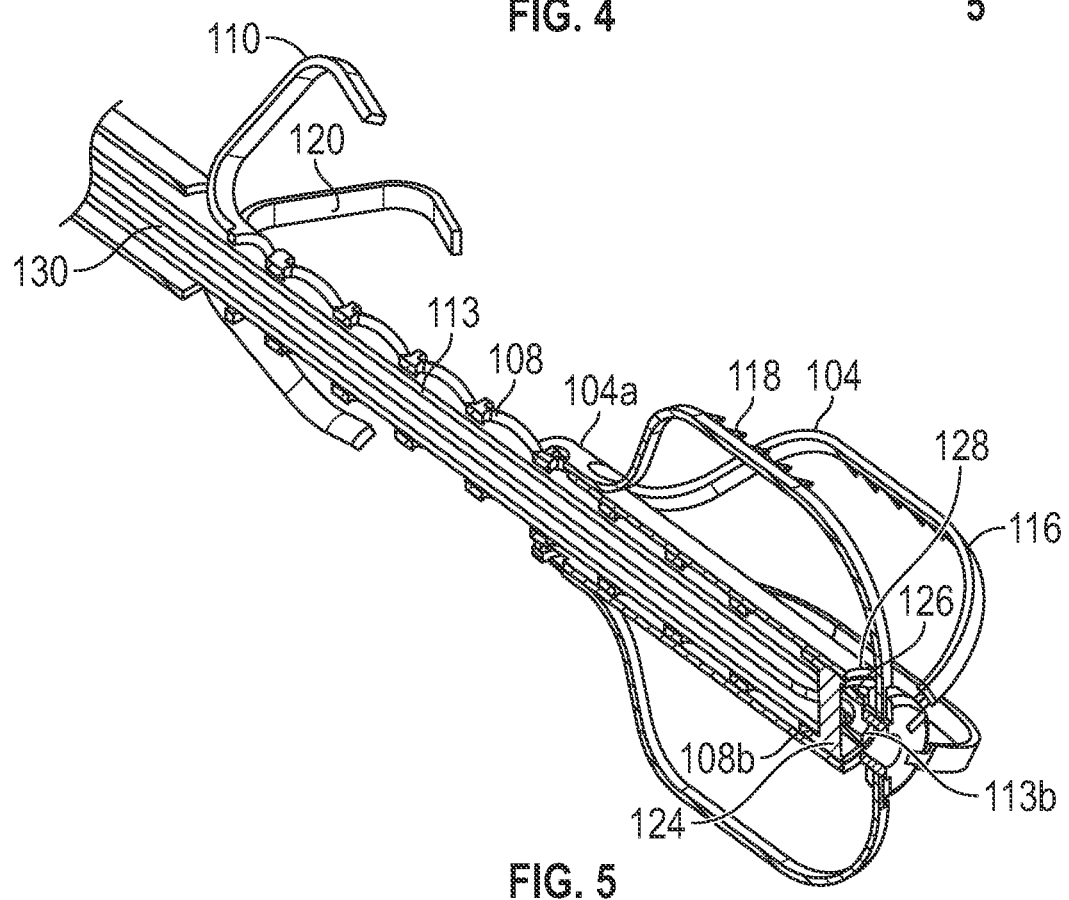
FIG. 5 is a section view of the implant device shown in FIG. 2A, taken through line 5-5 of FIG. 4.
Figure 6:
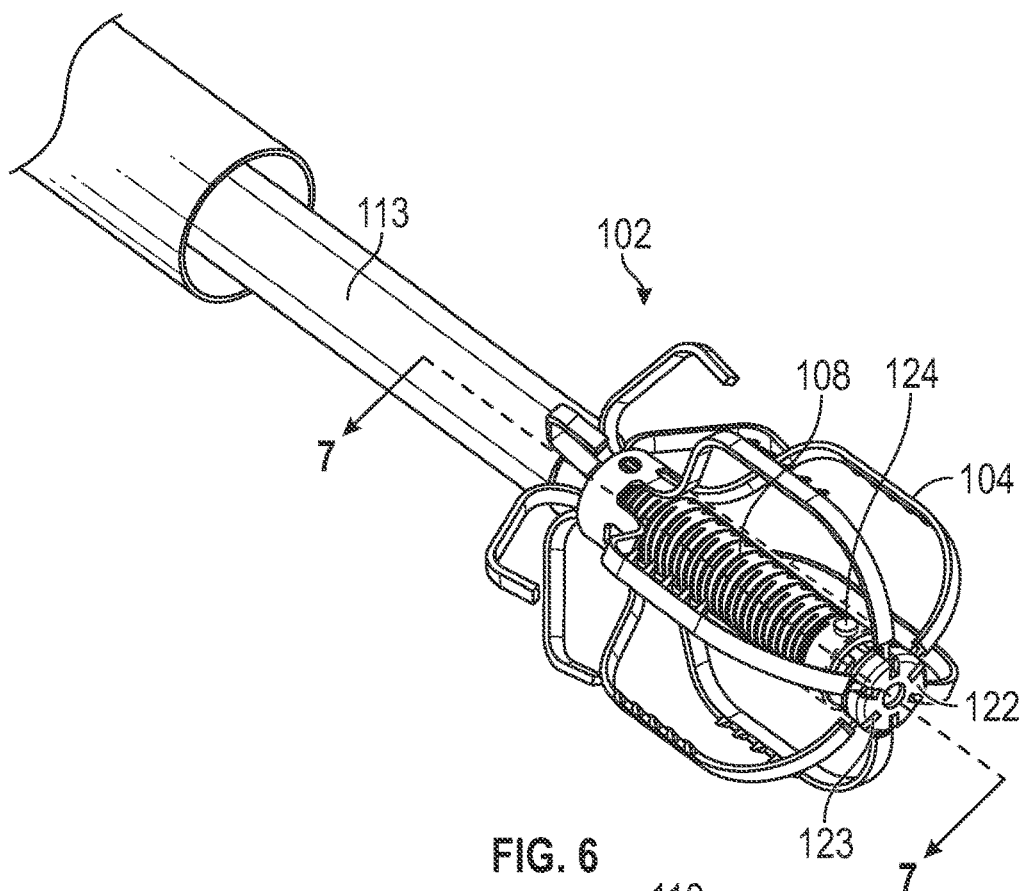
FIG. 6 shows the implant device of FIG. 2A wherein the contact member is in a second, open state, the retention member is in a second, contracted state, and the securing element is in a second, open state.

Further details regarding the implant system 100 will now be described, with reference to FIGS. 4-7. FIG. 4 shows the contact member 104 in the second, expanded state, the retention member 108 (also referred to herein as a biasing member) in the first, extended state, and the securing element 110 in the second, open state. In any embodiments disclosed herein, the retention member can be an axial spring-like member or other axially resilient member. In some embodiments, the contact member 104 can have a continuous and uninterrupted circumference at a proximal end 104a that each of the strut members 116 extend distally away from. Each of the strut members 116 can be preformed into a curved shape such that the strut members 116 are biased to expand to the second state when no external restraint or constraint is applied to the outside surface of the contact member 104 (for example, when in a relaxed state). At a distal end, each of the strut members 116 can, but are not required to, couple with a hub member 122. With reference to FIGS. 5-6, the hub member 122 can have a plurality of receptacles 123 configured to receive and constrain distal end portions 116b of each of the strut members 116. Additionally, each of the receptacles 123 can be configured to permit the distal end portions 116b of each of the strut members 116 to rotate relative to the hub member 122 so that the distal end portions 116b of the strut members 116 can extend generally radially away from the hub member 123 when the contact member 104 is in the second, expanded state. The hub member 123 can be configured to permit the distal end portions 116b of each of the strut members 116 to rotate relative to the hub member 122 without resistance or significant resistance. The distal ends of each of the strut members 116 can have a tab or other feature (such as a T shaped termination or other increased width) 119 that locks into, is secured by, or is otherwise engaged by each of the receptacles 123 so as to axially constrain the end portion of each of the strut members 116, while allow rotation about the end portion.

Figure 7:
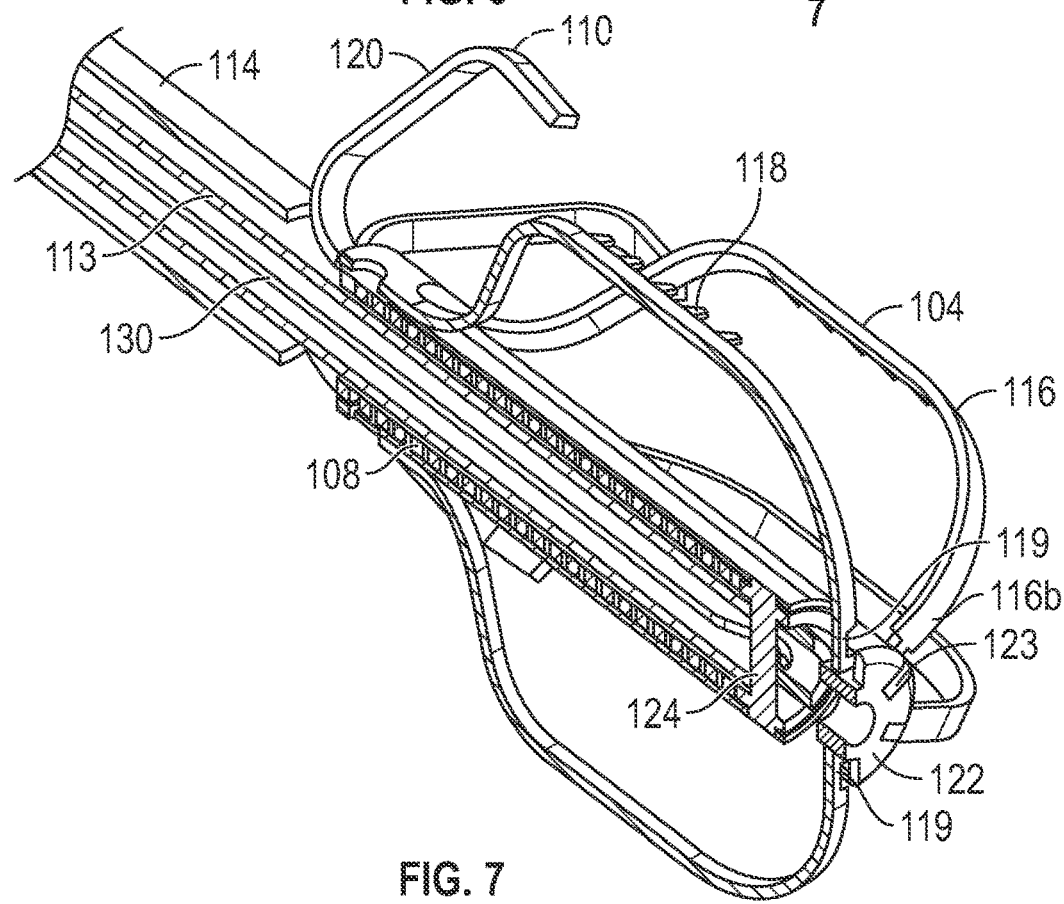
FIG. 7 is a section view of the implant device shown in FIG. 2A, taken through line 7-7 of FIG. 6.

In some embodiments, as in the embodiment illustrated in FIG. 4, the retention member 108 and the securing element 110 can be integrally formed. For example and without limitation, the retention member 108 and the securing element can be laser cut from a single length of tube material, for example, from an elastic or shape memory material, and thereafter formed into the desired shape using conventional or suitable processes. In other embodiments, the securing element 110 can be formed separately and coupled with a proximal end 108a of the retention member 108. In the relaxed state (i.e., the state where no external forces are acting thereon), some embodiments of the retention member 108 can be biased to move to the second or collapsed state, as shown in FIGS. 2E, 6, and 7, for example. Further, in the relaxed state, the retention member 110 can be in the second, or open position as also shown in FIG. 2E. Additionally, with reference to FIG. 5, which is an enlarged section view through line 5-5 of FIG. 4, a pin or cross member 124 can be coupled with a distal end 108b of the retention member 108 and can be configured to fit within a slot 126 formed within a distal end 113b of the core member 113. In this embodiment, the core member 113 can be advanced in a distal direction resulting in the advancement of the contact member 104 in a distal direction. Further, a core tube 128 can extend proximally from a distal end 113b of the core member 113 and couple with a proximal end 104a of the contact member 104. The pin 124 can extend through a pair of openings formed in the core tube 128 to secure the core tube 128 to the pin 124 and, hence, the distal end 108b of the retention member 108. The core tube 128 can, therefore, be used to couple the contact member 104 to the retention member 108. Pins, tabs, sutures, ties, protrusions, clips, depressions, detents, or other features can be used to couple a proximal end 104a of the contact member 104 with a proximal end of the core tube 128. Note that the core tube 128 has been omitted from some of the figures for clarity.

Additionally, in any embodiments, the system 100 can be configured so that the implant device 102 is biased or selectively secured in the proximal direction relative to the core member 113. For example and without limitation, as shown in FIG. 5, some embodiments of the implant device 102 can have a suture or thread 130 that extends through an inside of the core member 113 (such as through a lumen of the core member 113) and loops around the pin 124, thereby permitting a user to retract or withdraw the suture to pull the implant device 102 proximally relative to the core member 113. In this configuration, both ends of the suture 130 can extend from a proximal end of the device 100 such that a practitioner can grasp both ends of the suture 130 to exert the biasing force around the pin 124 to maintain the pin against a proximal end of the slot 126 formed within the distal end 113b of the core member 113. When the implant device 102 is ready to be released from the core member 113, the practitioner can simply release one end of the suture and withdraw the other end of the suture until the suture no longer forms a loop and/or no longer wraps around the pin 124. After removing the biasing force or retaining force from the suture 130 and/or removing the proximally directed force from the contact member, the core member 124 can be withdrawn relative to the implant device 102, while the contact member remains stationary within the cavity. This may be done after the contact member and the securing element have been fully deployed or implanted into the cavity and/or tissue adjacent to the cavity.

Further, in any embodiments disclosed herein, the pin or cross member 124 can be configured to permit a guidewire to pass through a distal end portion of the implant device 102 without obstruction. For example without limitation, an opening larger than an outside diameter of a guidewire can be formed in the pin 124 to permit a guidewire to pass therethrough, or the pin 124 can be formed in two parts, with a sufficiently large space therebetween.

Figure 8A:
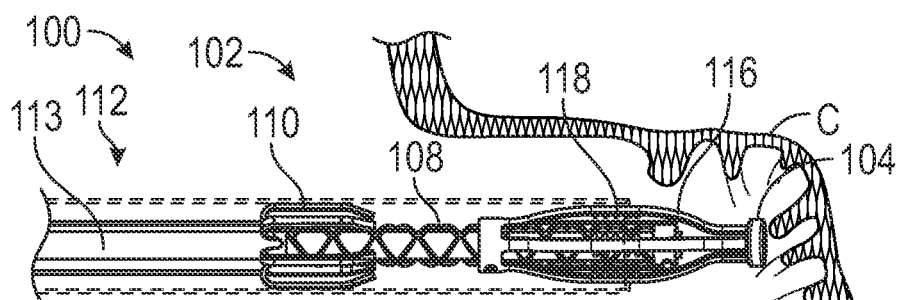
FIG. 8A shows the embodiment of the implant device of FIG. 2A, showing the contact member being advanced further distally into the cavity.
Figure 8B:
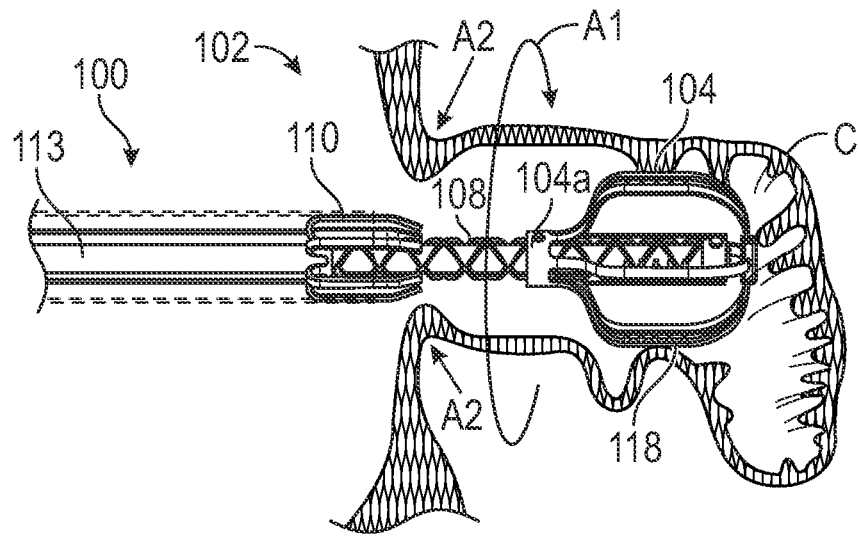
FIG. 8B shows the embodiment of the implant device of FIG. 2A, showing the contact member being rotated to twist the cavity and cause a neck or opening of the cavity to constrict around a portion of the implant device.
Figure 8C:
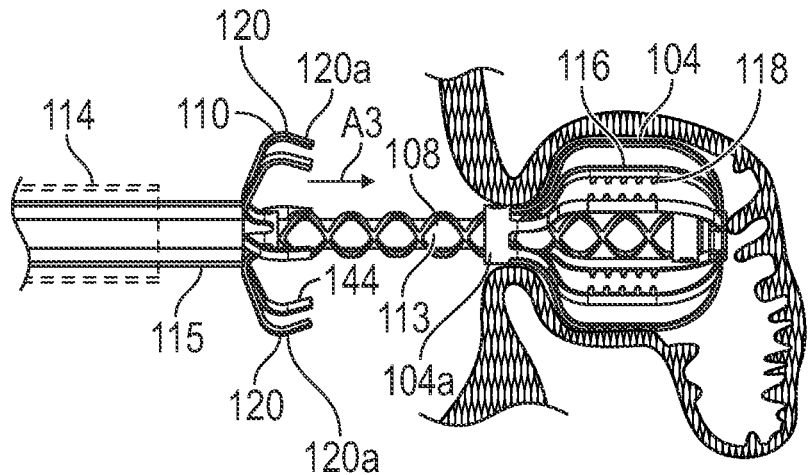
FIG. 8C shows the embodiment of the implant device of FIG. 2A, showing the securing element of the embodiment of the implant device being advanced toward the contact member of the implant device.

With reference to FIGS. 8A-8C, in any embodiments, the contact member 104 of the implant device 102 can be advanced as far into the cavity is desired by the surgeon, or as is appropriate. For example and without limitation, as shown in FIGS. 8A-8C, the contact member 104 can be advanced into contact with, adjacent to, or near to a distal end of the cavity before the contact member 104 is rotated. This will permit more of the implant to be positioned within the cavity and, in some embodiments, more of the tissue of the cavity to constrict around a body portion or other portion of the implant device 102. This can, in some embodiments, permit the user to rotate the contact member 104 of the implant device 102 to a greater extent, and can also result in less stress on the tissue of the cavity. Any implant device embodiments disclosed herein can be configured to be advanced to any extent within the cavity, including being advanced just past the opening of the cavity, in the middle portion of the cavity, advanced further into the cavity so as to be into contact with, adjacent to, or near to a distal end of the cavity, before the contact member 104 is rotated.

FIGS. 9A-9I show another embodiment of treatment system 140 for closing or occluding a cavity. In any embodiments disclosed herein, any components, features, or other details of the treatment system 140 or implant device 142 can have any of the components, features, or other details of any other treatment system embodiments or implant device embodiments disclosed herein, including without limitation any of the embodiments of the treatment system 100 or implant device 102 described above, in any combination with any of the components, features, or details of the treatment system 140 or implant device 142 disclosed below. Similarly, any components, features, or other details of any of the other treatment system embodiments or implant device embodiments disclosed herein can have any of the components, features, or other details of any embodiments of the treatment system 140 or implant device 142 disclosed herein in any combination with any of the components, features, or details of the treatment system and/or implant device.

Figure 9A:
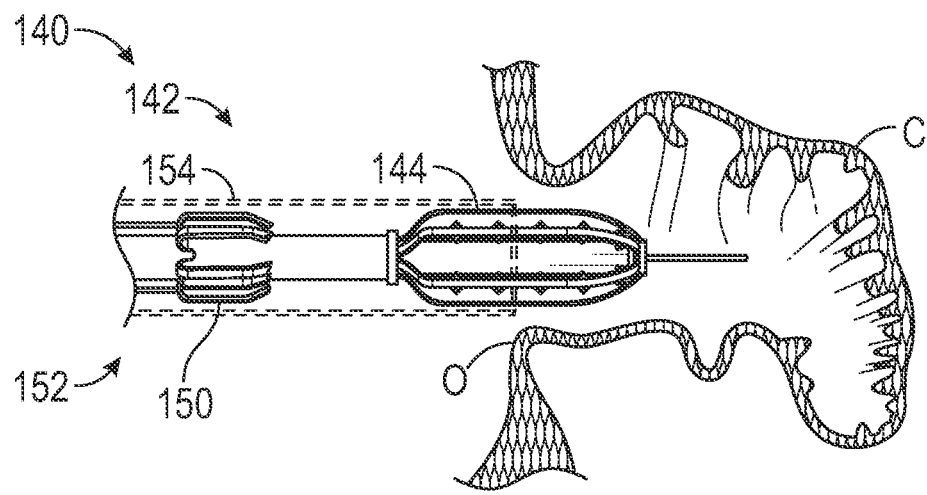
FIG. 9A shows another embodiment of treatment system having an implant device being advanced through a catheter into the cavity, the implant device being in a collapsed state and restrained within an outer tube of the catheter.
Figure 9B:
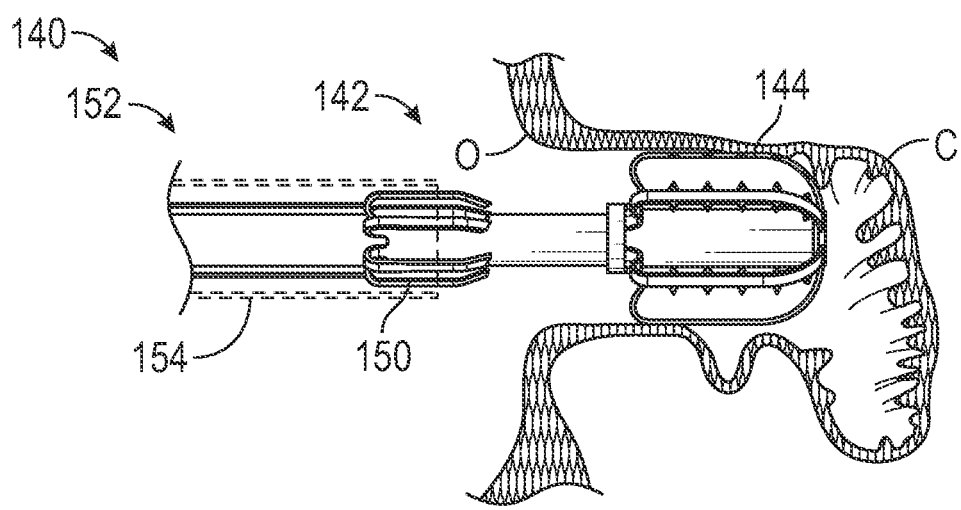
FIG. 9B shows the embodiment of the treatment system of FIG. 9A, showing the contact member being expanded within the cavity.
Figure 9C:
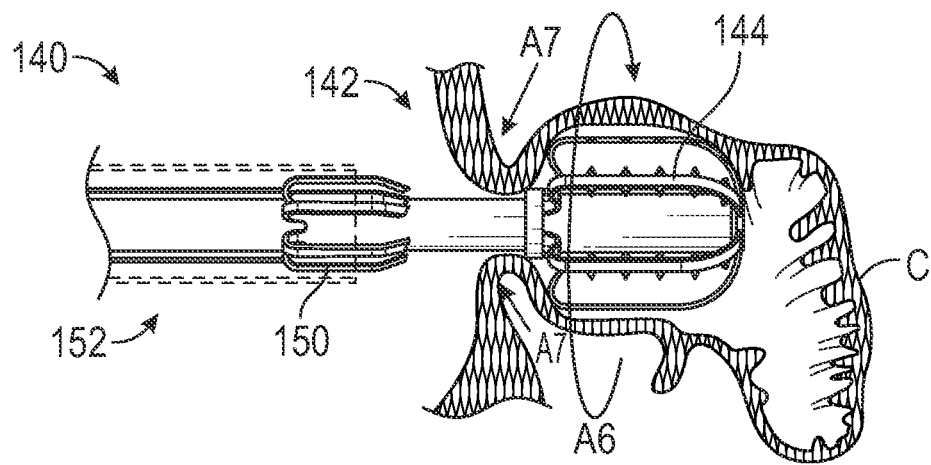
FIG. 9C shows the embodiment of the treatment system of FIG. 9A, showing the contact member being rotated to twist the cavity and cause a neck or opening of the cavity to constrict around a portion of the implant device.
Figure 9D:
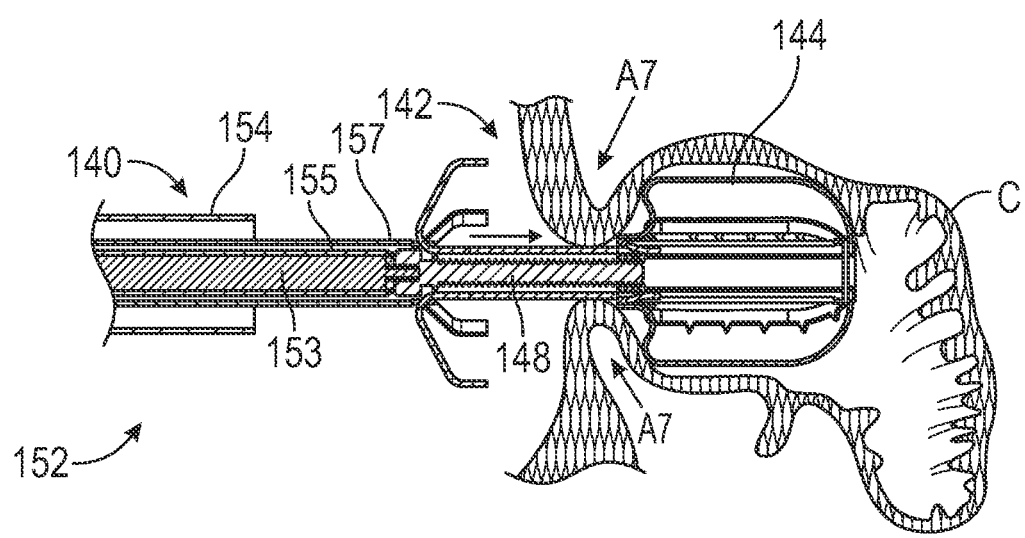
FIG. 9D shows the embodiment of the treatment system of FIG. 9A, showing the securing element of the embodiment of the implant device being advanced toward the contact member of the implant device.

In any embodiments of the occlusion system 140, including the embodiment of the occlusion system 140, the system can have an implant device 142 having a contact member 144 (also referred to herein as a contact element or an expandable implant member), a securing element or securing element 150 (also referred to as a securing member), and a retention member 148. FIG. 9A shows the contact member 144 and the securing element 150 both in a first, contracted or restrained state within an outer sleeve 154 of the catheter 152. The implant device 142 can be advanced distally out of the catheter 152 past a distal end 154a of the outer sleeve 154 by advancing a core member 153 of the catheter 152 so that the contact member 144 of the implant device 142 can be deployed within the cavity at any desired depth within the cavity, including near a distal end of the cavity, the middle portion of the cavity, or otherwise by, for example and without limitation, holding the implant device 142 in a stationary axial position by maintaining the core member 153 of the catheter 152 in a stationary axial position and retracting the outer sleeve 154 of the catheter 152. In any embodiments disclosed herein, the contact member 144 can be self-expanding in a radial direction so that, when a restraint is removed from the contact member 144, the contact member 144 can expand against an inner surface or wall of the cavity automatically. In other embodiments, the contact member 144 can be mechanically expandable, such as by a balloon expander, so as to expand against inside surface or wall of the cavity.

In any embodiments, the contact member 144 can have a plurality of arms or struts 156 that are each configured to self-expand in a radial direction when a restraint has been removed from an outside surface of the contact member 144. For example without limitation, any embodiments of the contact member disclosed herein can have six struts 156, or between six and ten struts, or from less than six to more than ten struts. Further, in any embodiments, the contact member 144 can have a plurality of tissue anchors 158 or other similar features configured to penetrate or engage the tissue of the cavity that are configured to penetrate into a tissue within the cavity when the contact member 144 is expanded against the tissue of the cavity and/or when the contact member 144 is rotated or twisted within the cavity.

In this configuration, when the contact member 144 is rotated in a first direction (indicated by arrow A6 in FIG. 9C, which can be in the clockwise or the counterclockwise direction), one or more or all of the struts 156 and one or more or all of the tissue anchors 158 can engage the tissue of the cavity and cause the cavity to twist or rotate in the first direction A6. The twisting or rotation of the cavity in the first direction from a first rotational position to a second rotational position results in the opening O of the cavity constricting in a radial direction (represented or identified by arrows A7 in FIG. 9C) so that the opening O of the cavity is caused to move or constrict around an outside surface of a proximal portion 144a of the contact member 144. An operator can twist or rotate the contact member 144 by twisting or rotating the core member 153 of the catheter 152. The tightening or constriction of the opening O of the cavity around an outside surface of the proximal portion 144a of the contact member 144 or other portion of the implant device can result in the occlusion, or substantial occlusion, or substantial closing off of the interior portion of the cavity from the space outside of or adjacent to the cavity, thereby substantially reducing the health risks associated with an open cavity. In any embodiments disclosed herein, the implant 142 can be configured to be removed after the securing element is applied to the tissue that has been constricted by the twisting of the contact member so that the only portion of the implant device 142 left in the cavity or the space outside of or adjacent to the cavity is the securing element 150.

Figure 9E:
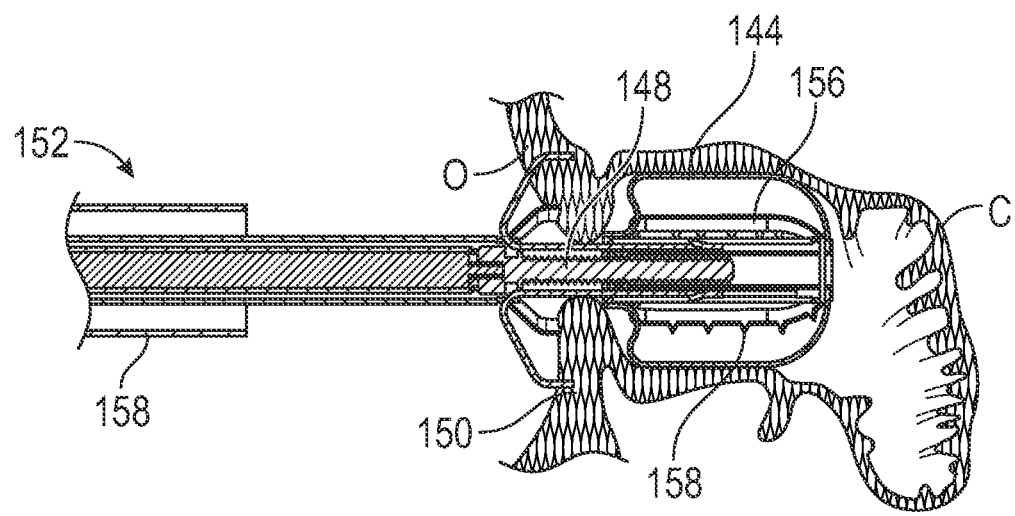
FIG. 9E shows the securing element of the treatment system of FIG. 9A engaged with the patient's tissue surrounding the proximal portion of the contact member of the implant device.
Figure 9F:
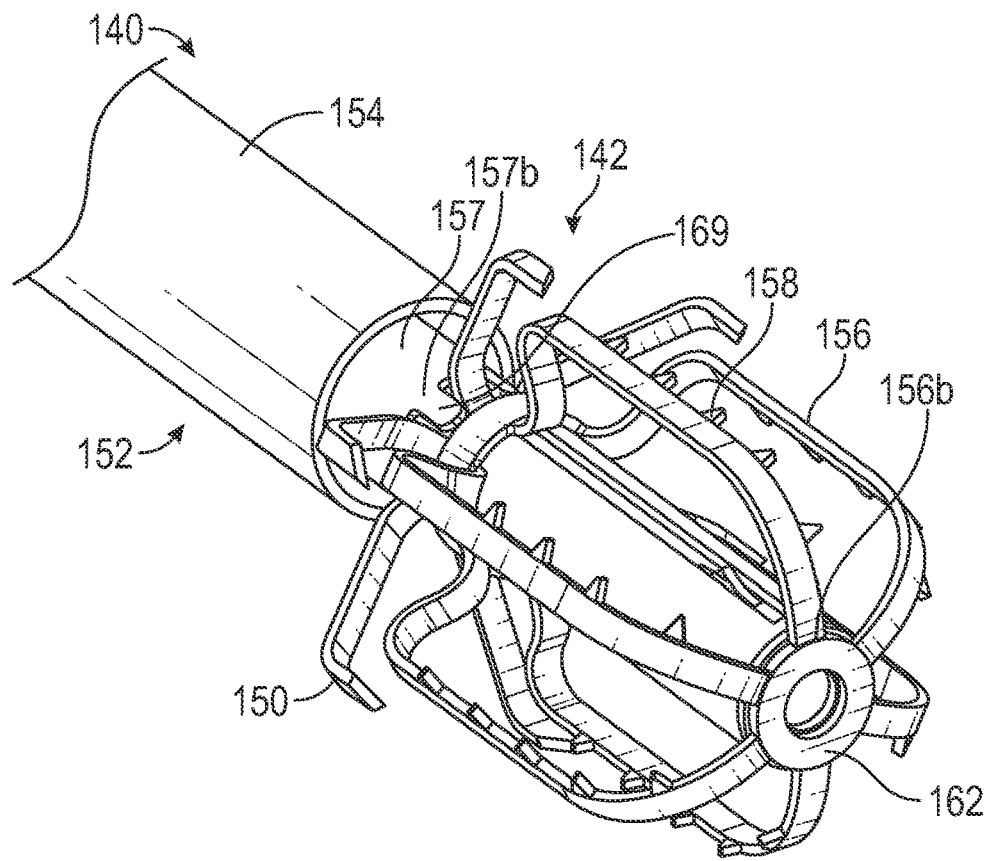
FIG. 9F shows the treatment system of FIG. 9A wherein the contact member is in a second, expanded state, the retention member is in a second, contracted state, and the securing element is in a second, open state.
Figure 9G:
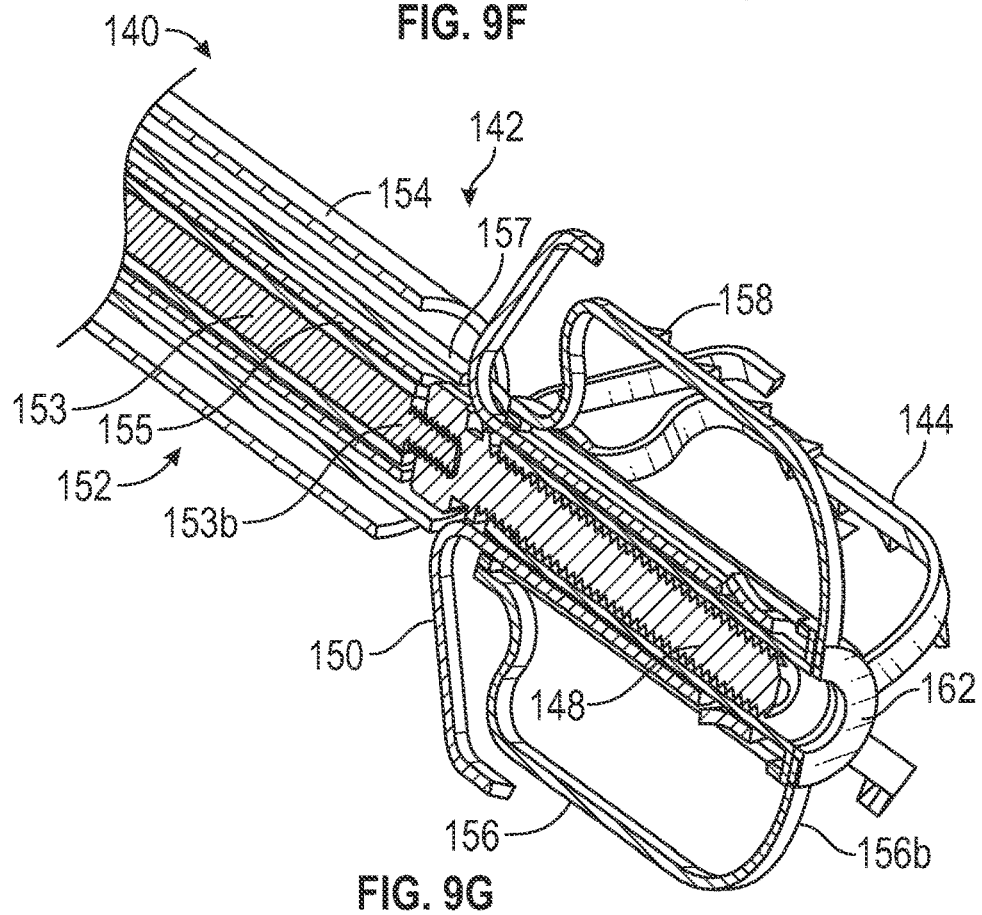
FIG. 9G is a section view of the treatment system shown in FIG. 9A.
Figure 9H:
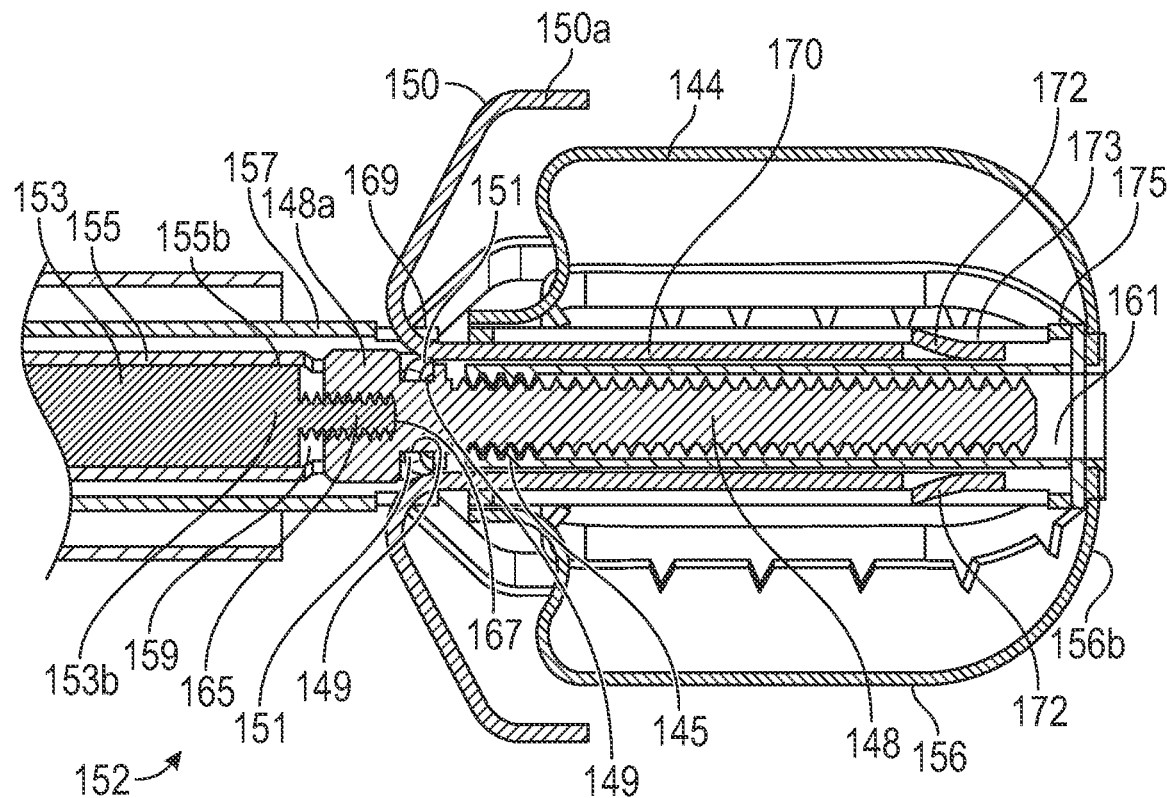
FIG. 9H shows an enlarged side view of the treatment system of FIG. 9A.

The retention member 148 can be used to couple the securing element 150 to the contact member 144 and to also allow a user (such as a surgeon) to move the securing element 150 toward and away from the contact member 144. In any embodiments, the retention member 148 can have helical threads on an outer surface thereof. In any embodiments, the retention member 148 can comprise a threaded shaft. In this configuration, the retention member 148 can be rotated in a first direction to advance the securing element 150 toward the contact member 144, and rotated in a second, opposite direction to move the securing element 150 away from the contact member 144. The retention member 148 can be configured to engage the securing element 150 such that, when the retention member 148 rotates, the securing element 150 moves in an axial direction corresponding to the rotation of the retention member 148. For example and without limitation, the retention member 148 can have an annular recess 149 near a proximal end 148a thereof that is configured to engage or couple with a tab or projection 151 of the securing element 150. In some embodiments, the projection 151 can extend into the annular recess 149 so as to axially lock or engage the securing element 150 with the retention member 148. The interaction of the projection 151 with the annular recess 149, wherein the walls of the annular recess contact and push the projection 151, causes the retention member 148 to move the securing element 150 when the retention member 148 is rotated. In some embodiments, as in the illustrated embodiment, the securing element 150 can have two tabs 151, both engaged with the annular recess 149. The contact member 144 can have a threaded neck portion 145 that threadedly engages the threads of the retention member 148 so that the retention member 148 threads into and out of the threaded neck portion 145. In this configuration, the retention member 148 threads into and out of the contact member 144 to cause the securing element 150 to move relative to the contact member. As shown in FIG. 9H, the retention member 148 is nearly completely threaded into the contact member 144 and into the cavity or space 161 within the contact member 144 such that the securing element 150 is moved toward the contact member 144 about as much as the securing element 150 can be. As the retention member 148 is rotated in the second direction, the retention member 148 will move out of the space 161 within the contact member 144 and move the securing element 150 away from the contact member 144.

With reference to FIG. 9H, an intermediate sleeve 155 can be advanced distally into contact with and engage a proximal end portion 148a of the retention member 148. The intermediate sleeve 155 can be configured such that, when the intermediate sleeve 155 is engaged with the proximal end portion 148a of the retention member 148, the retention member 148 can be rotated in the first or second direction by rotating the intermediate sleeve 155 in the first or second direction. In some embodiments, the intermediate sleeve 155 can be moved axially and rotated independently of the other tubes or sleeves of the catheter 152. For example and without limitation, as shown in FIG. 9H, projections or tabs 159 on a distal end portion 155b of the intermediate sleeve 155 can selectively couple with or be advanced into recesses or depressions 147 formed in the proximal end portion 148a of the retention member 148 that can selectively key or index the intermediate tube 155 with the retention member 148.

Further, in any embodiments, retention member 148 can be used to couple the implant 142 to the delivery catheter 152. For example and without limitation, the core member 153 of the delivery catheter 152 can be coupled with the retention member 148 via a threaded projection 165 at a distal end 153b of the core member 153 that threadedly engages a threaded recess 167 formed in a proximal end portion 148a of the retention member 148. The threaded projection 165 can be formed separately from and coupled with a distal end of the core member 153, or can be formed monolithically therewith. In this configuration, the implant 142 can be removed from the catheter by disengaging the threaded projection 165 from the retention member 148. This can be performed by preventing a rotation of the retention member 148 using the intermediate tube 155 while the core member 153 is being rotated in a second direction so as to withdraw the threaded projection 165 from the recess 167 of the retention member 148.

Further, a second intermediate tube or sleeve 157 can be advanced distally into contact with and engage a proximal end portion 150a of the securing element 150. The second intermediate sleeve 157 can be configured such that, when the second intermediate sleeve 157 is engaged with the proximal end portion 150a of the securing element 150, the securing element 150 can be rotated in the first or second direction by rotating the second intermediate sleeve 157 in the first or second direction. In some embodiments, the second intermediate sleeve 157 can be moved axially and rotated independently of the other tubes or sleeves of the catheter 152. For example and without limitation, as shown in FIG. 9H, projections or tabs 169 on a distal end portion 157b of the second intermediate sleeve 157 can selectively couple with the struts or arms of the securing element 150 so that the second intermediate sleeve 157 can be keyed or indexed to the securing element 150.

Further, in some embodiments, the securing element 150 can be keyed or indexed to the contact member 144 so that the securing element 150 and the contact member 144 rotate dependently and simultaneously. For example, in some embodiments, the securing element 150 can have a body portion 170 having one or more tabs or projections 172 that are configured to extend into a channel or recess 173 formed in a body portion 175 of the contact member 144. One or more channels 173 can be formed in an axial orientation such that the projection(s) 172 of the securing element 150 and the securing element 150 can freely move in an axial direction relative to the contact member 144. However, a narrow width of the channel(s) 173 relative to the projection(s) 172 can prevent the projection(s) 172 and, hence, the securing element 150 from rotating relative to the contact member 144.

In this configuration, the second intermediate sleeve 155 can be coupled with the securing element 150 and can be used to at least rotate the implant 142 in the first or second direction. For example and without limitation, the second intermediate sleeve 155 can be rotated to rotate the contact member 144 to twist the cavity to the desired level of rotation and/or torque. Thereafter, the second intermediate sleeve 155 can be used to maintain the desired rotational position of the contact member 144 by maintaining the second intermediate sleeve 155 in contact with the securing element 150 and in a fixed rotational position, hence holding the contact member 144 in a fixed rotational position while the retention member 148 is rotated in the first direction to advance the securing element 150 toward the contact member 144. Once the securing element 150 is in the desired axial position (for example, engaged with the tissue of the LA/cavity that has constricted as a result of the twisting of the contact member 144), the implant 142 can be removed from the catheter 152 by disengaging the threaded projection 165 from the retention member 148 as described above, and the catheter can be removed from the LA. With the securing element 150 engaged with the patient's tissue, as illustrated in FIG. 9E, the cavity is prevented from rotating to the first rotational position, which is the untwisted or relaxed position. In this configuration, the implant device 142 can secure and maintain the cavity in a substantially or completely occluded or substantially or completely closed state.

Figure 11:
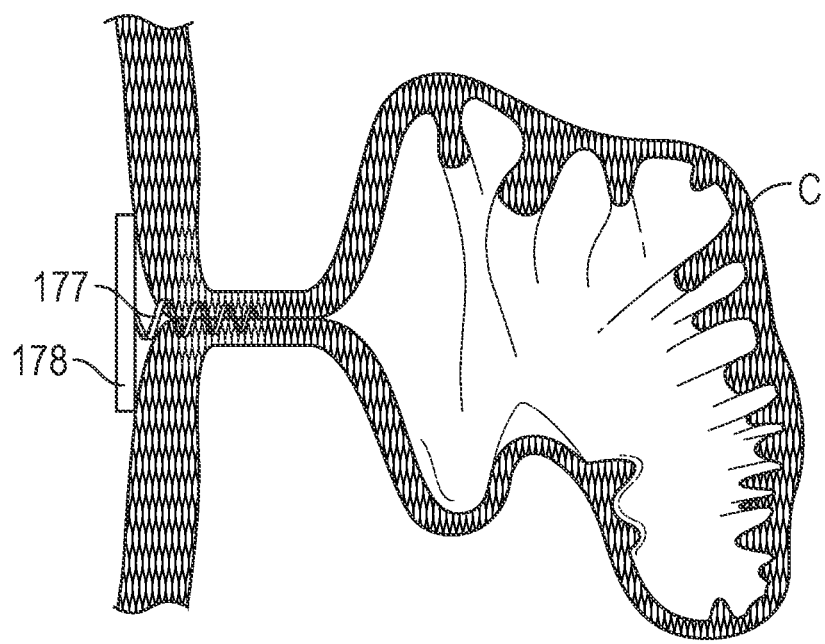
FIG. 11 shows an embodiment of a securing element implanted adjacent to an occluded opening of the cavity.
Figure 12:
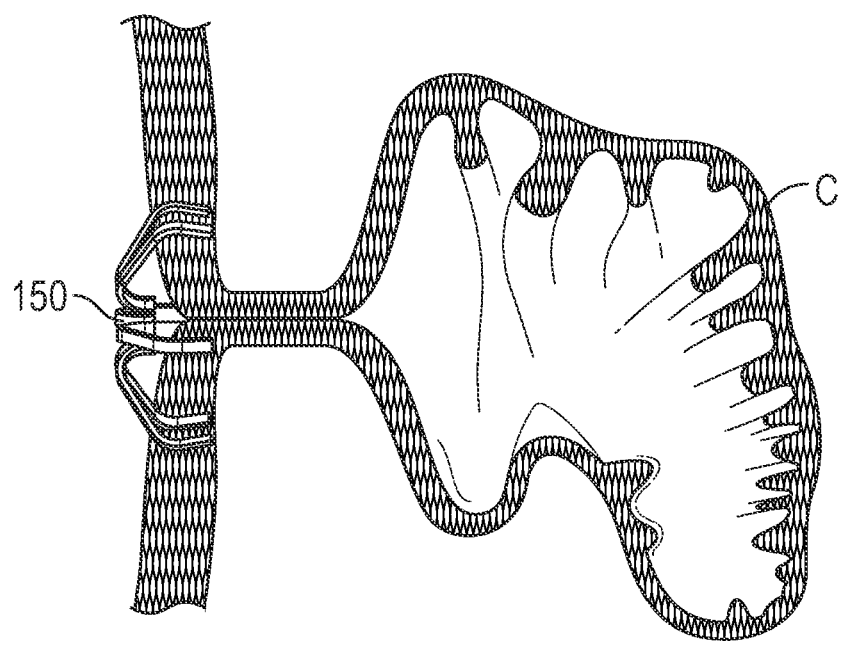
FIG. 12 shows another embodiment of a securing element implanted adjacent to an occluded opening of the cavity.

Further, in any embodiments, the device can be configured such that the contact member 144 can be removed from the patient's cavity after the securing element 150 is engaged with the tissue sufficiently to hold the tissue in a closed or occluded state, for example as shown in FIGS. 11-12, wherein the securing element 177 and the securing element 150 are the only components remaining within the body following the completely of the implant procedure. In this configuration, the implant can have a plug or cover (such as cover 178 coupled with the securing member 177) that can cover the opening in the implant that the contact member (such as contact member 180 or contact member 144) is withdrawn through, or be otherwise configured to plug or cover the opening in the implant that the contact member 144 is withdrawn through. For example and without limitation, a cover member such as cover member 121 can be coupled with the securing element 150 to substantially cover any openings in the implant, or can be coupled with the contact member 144 so as to cover the contact member 144 inside the cavity, in configurations where the contact member 144 remains in the cavity after the securing element 150 has been implanted.

Additionally, in some embodiments, the contact member 144 can have a continuous and uninterrupted circumference at a proximal end 144a that each of the strut members 156 extend distally away from. Each of the strut members 156 can be preformed into a curved shape such that the strut members 156 are biased to expand to the second state when no external restraint or constraint is applied to the outside surface of the contact member 144 (for example, when in a relaxed state). At a distal end, each of the strut members 156 can, but are not required to, couple with a hub member 162. Similar to the hub member 122 described above, the hub member 162 can have a plurality of receptacles (not shown) configured to receive and constrain distal end portions 156b of each of the strut members 156. Additionally, each of the receptacles 163 can be configured to permit the distal end portions 156b of each of the strut members 156 to rotate relative to the hub member 162 so that the distal end portions 156b of the strut members 156 can extend generally radially away from the hub member 163 when the contact member 144 is in the second, expanded state. The hub member 163 can be configured to permit the distal end portions 156b of each of the strut members 156 to rotate relative to the hub member 162 without resistance or significant resistance. In any embodiments, the distal ends of each of the strut members 156 can have a tab or other feature (such as a T shaped termination or other increased width) (not shown) that locks into, is secured by, or is otherwise engaged by each of the receptacles 163 so as to axially constrain the end portion of each of the strut members 156, while allow rotation about the end portion.

Figure 10:
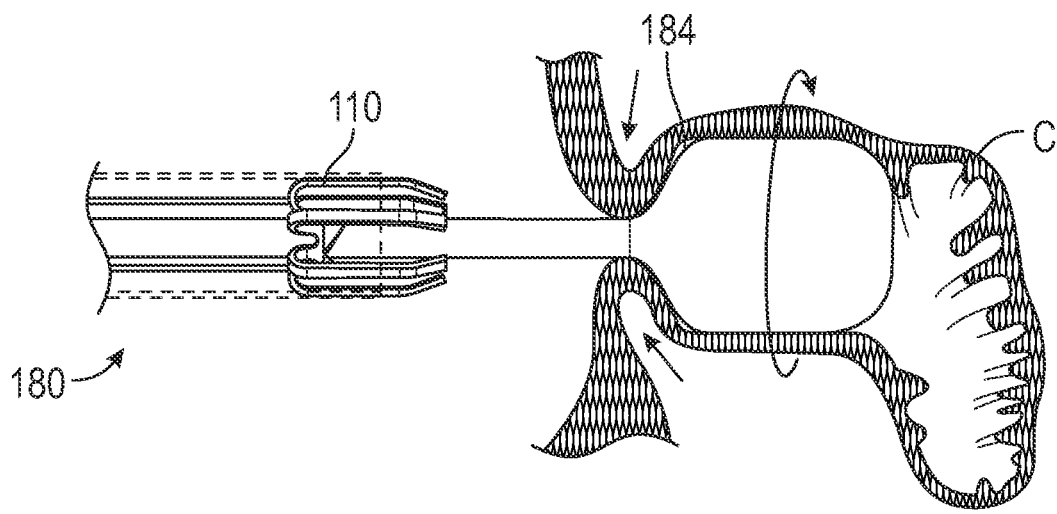
FIG. 10 shows another embodiment of a treatment system for treating the cavity, showing the contact member of the treatment system being expanded within the cavity.
Figure 9I:
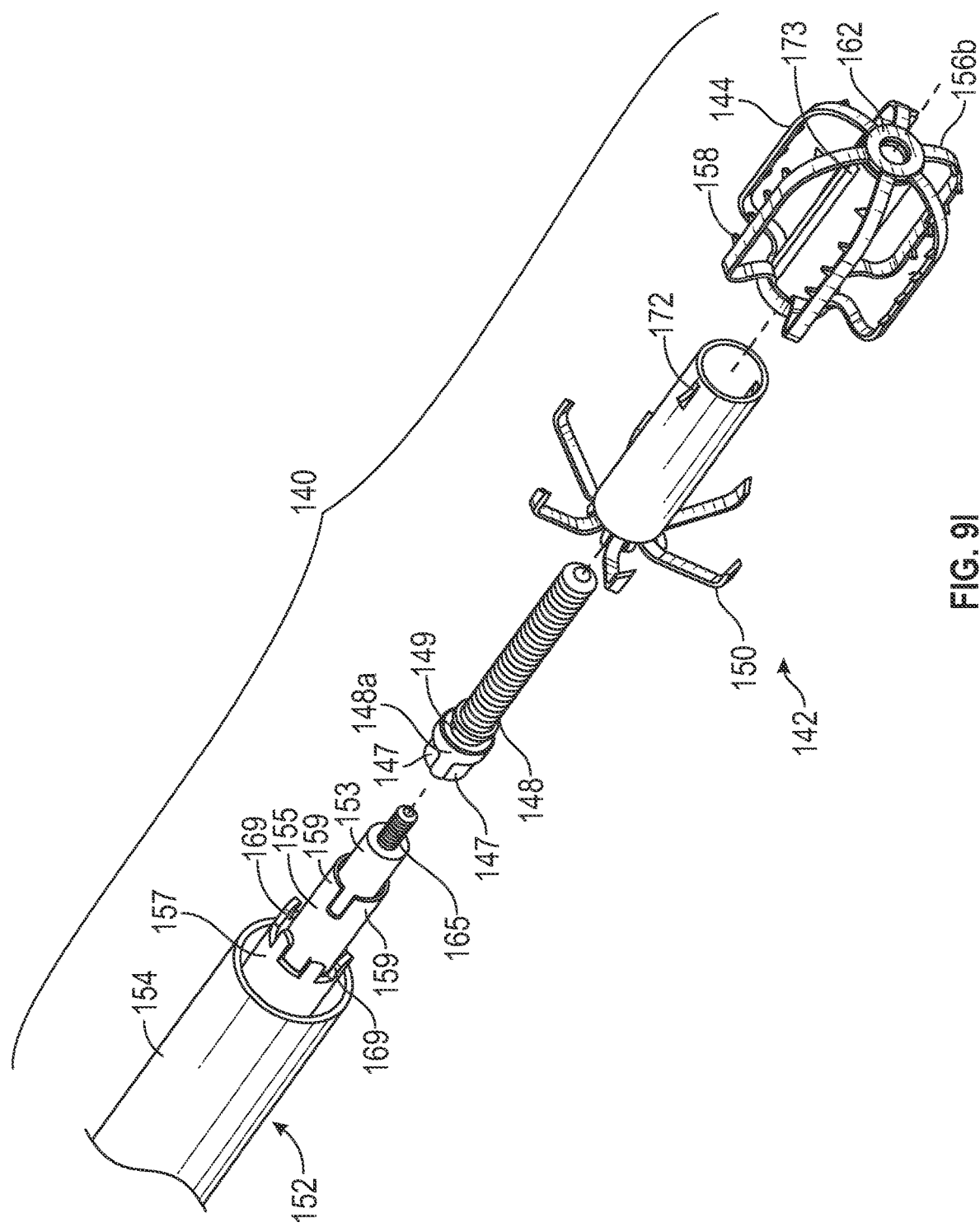
FIG. 9I shows an exploded view of the treatment system of FIG. 9A.

Additionally, as described above, in any embodiments disclosed herein, the implant device can be configured such that the contact member can be removed from the patient's cavity after the securing element engages the tissue to hold the opening of the cavity in a closed state. For example, with reference to FIG. 10, in any embodiments disclosed herein, the contact member can be an expansion balloon such as an expansion balloon 184 and/or any embodiments of the implant herein can comprise a balloon such as an expansion balloon. The balloon can have a smooth outside surface, or can have dimples, projections, rough texture, tissue anchors, or otherwise to engage the inside surface of the cavity. In some embodiments, the balloon can be a typical expansion balloon such as a balloon used in angioplasty procedures, and can be sized and configured for use in cavity. In these configurations, after the cavity has been rotated and/or torqued to the desired degree and the securing element implanted to hold the opening of the cavity sufficiently closed or constricted, the balloon can be deflated and removed from the cavity, leaving only the securing element to maintain the cavity in the occluded state, as shown in the nonlimiting examples of FIGS. 11-12.

Figure 13:
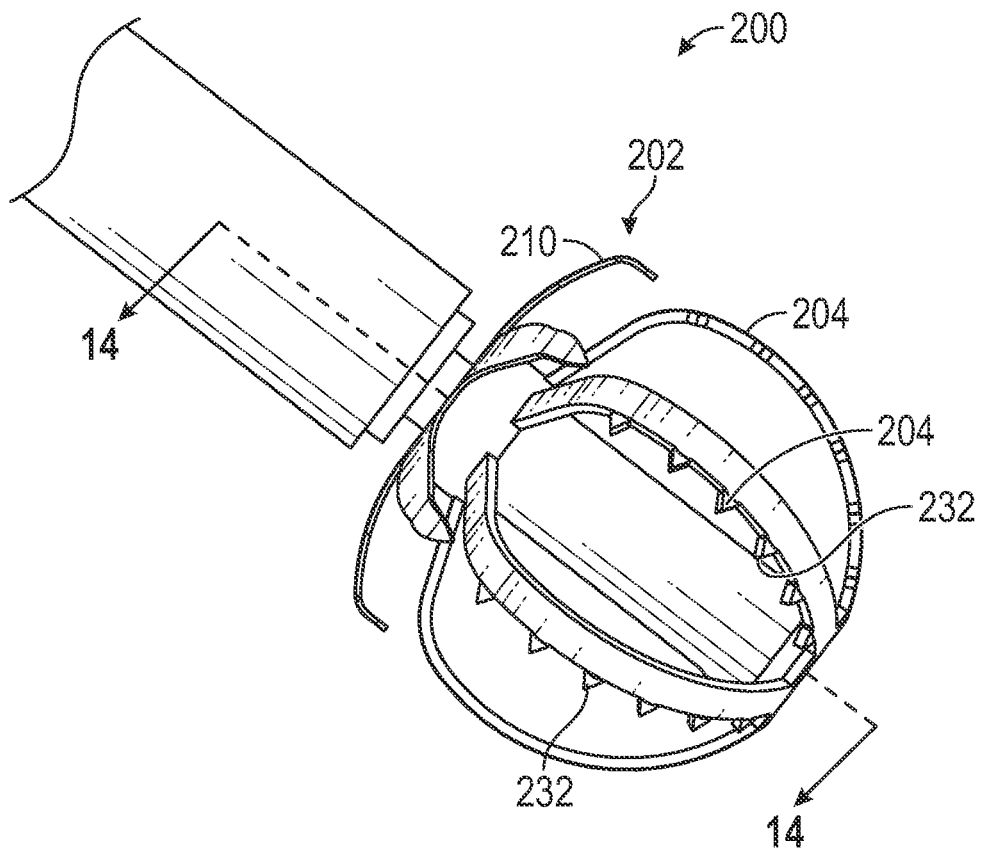
FIG. 13 shows another embodiment of treatment system having an implant device wherein the contact member is in a second, expanded state, the retention member is in a second, contracted state, and the securing element is in a second, open state.
Figure 14:
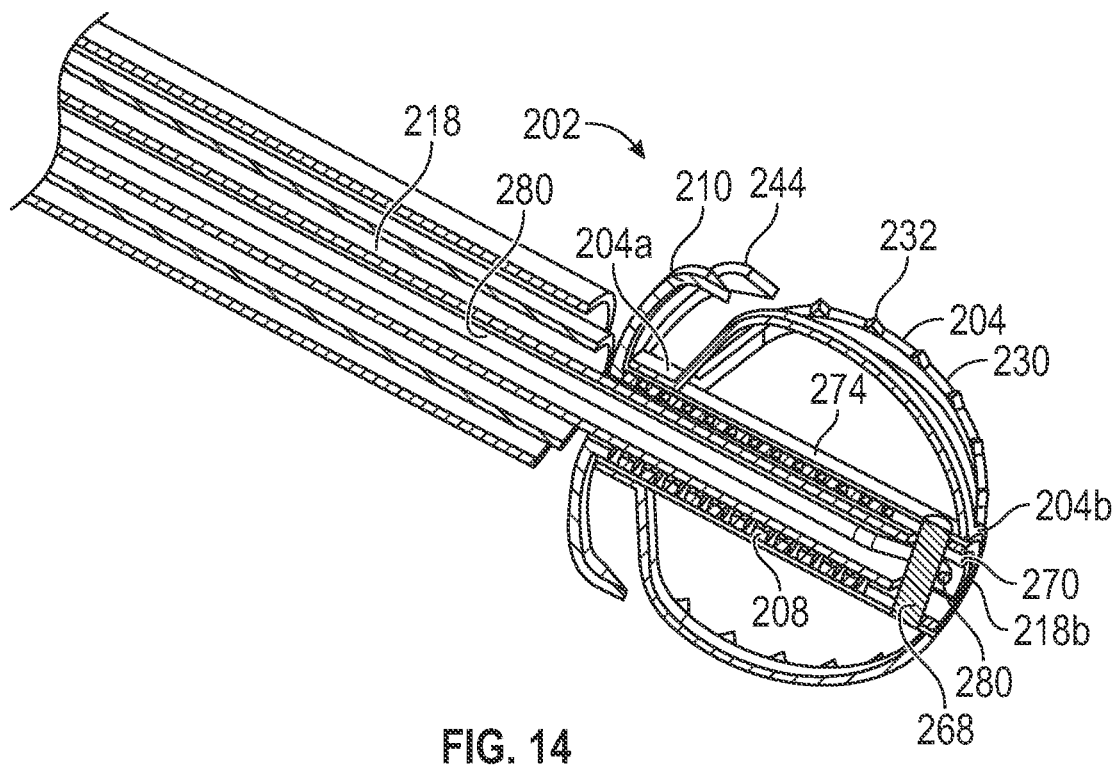
FIG. 14 is a section view of the treatment system shown in FIG. 13, taken through line 14-14 of FIG. 13.

FIG. 13 shows another embodiment of treatment system 200 having an implant device 202, wherein the contact member 204 of the implant device 202 is in a second, expanded state, the retention member 208 is in a second, contracted state, and the securing element 210 is in a second, open state. FIG. 14 is a section view of the embodiment of the treatment system 200 shown in FIG. 13, taken through line 14-14 of FIG. 13. In any embodiments disclosed herein, any components, features, or other details of the treatment system 200 or implant device 202 can have any of the components, features, or other details of any other treatment system embodiments or implant device embodiments disclosed herein, including without limitation any of the embodiments of the treatment system 100 or implant device 102 described above, in any combination with any of the components, features, or details of the treatment system 200 or implant device 202 disclosed below. Similarly, any components, features, or other details of any of the other treatment system embodiments or implant device embodiments disclosed herein can have any of the components, features, or other details of any embodiments of the treatment system 200 or implant device 202 disclosed herein in any combination with any of the components, features, or details of the treatment system and/or implant device.

With reference to FIGS. 13-14, in some embodiments, the contact member 204 can have an annular proximal end portion 204a wherein all of the arms or struts 230 (six being shown) of the contact member 204 extend distally away from the proximal end portion 204a. The struts 230 can have any form of tissue anchors 232 on the struts or attached to the struts, such as any of the tissue anchors 118 described above.

Additionally, in some embodiments, the contact member 204 can have an annular distal end portion 204b wherein all of the arms or struts 230 can be coupled with the annular distal end portion 204b. The contact member 204 can have a bulbous shape, cylindrical shape with a curved distal portion, an elongated spherical shape, or otherwise. In some embodiments, the contact member 204 can be laser cut from a hypotube, or can be formed from different components and welded, brazed, or otherwise coupled together. Each of the strut members 230 can be preformed into a curved shape (which can have a spherical or bulbous shape) and formed such that the strut members 230 are biased to expand to the second state when no external restraint or constraint is applied to the outside surface of the contact member 204.

In some embodiments, as in the illustrated embodiment, the retention member 208 and the securing element 210 can be integrally formed. For example and without limitation, the retention member 208 and the securing element can be laser cut from a single length of tube material, for example, from an elastic or shape memory material such as Nitinol, and thereafter formed into the desired shape. In other embodiments, the securing element 210 can be coupled with a proximal end 208a of the retention member 208. In the relaxed state (i.e., the state where no external forces are acting thereon), some embodiments of the retention member 208 can be biased to move to the second or collapsed state, for example, and the securing element 210 can be in the second, or open state.

Additionally, with reference to FIG. 14, a pin or cross member 268 can be coupled with a distal end 208b of the retention member 208 and can be configured to fit within a slot 270 formed within a distal end 218b of the core member 218. In this embodiment, the core member 218 can be advanced in a distal direction resulting in the advancement of the contact member 204 in a distal direction. Further, a core tube 274 can extend proximally from a distal end 218b of the core member 218 and couple with a proximal end 204a of the contact member 204. The pin 268 can extend through a pair of openings formed in the core tube 274 to secure the core tube 274 to the pin 268 and, hence, the distal end 208b of the retention member 208. The core tube 274 can be, therefore, be used to couple the contact member 204 with the retention member 208. Pins, tabs, sutures, ties, protrusions, clips, depressions, detents, or other features can be used to couple a proximal end 204a of the contact member 204 with a proximal end of the core tube 274.

Additionally, in any embodiments, the system 200 can be configured so that the implant device 202 is biased in the proximal direction relative to the core member 218. For example and without limitation, as shown in FIG. 14, some embodiments of the implant device 202 can have a suture or thread 280 that extends through an inside of the core member 218 (such as through a lumen of the core member 218) and loops around the pin 268, thereby permitting a user to retract or withdraw the suture to pull the implant device 202 proximally relative to the core member 218. In this configuration, both ends of the suture 280 can extend from a proximal end of the device 200 such that a practitioner can grasp both ends of the suture 280 to exert the biasing force around the pin 268 to maintain the pin against a proximal end of the slot 270. When the implant device 202 is ready to be released from the core member 218, the practitioner can simply release one end of the suture and withdraw the other end of the suture until the suture no longer forms a loop or wraps around the pin 268. After removing the biasing force from the suture 280, the core member 268 can be withdrawn relative to the implant device 202. This may be done after the contact member and its securing element have been fully deployed.

Figure 15:
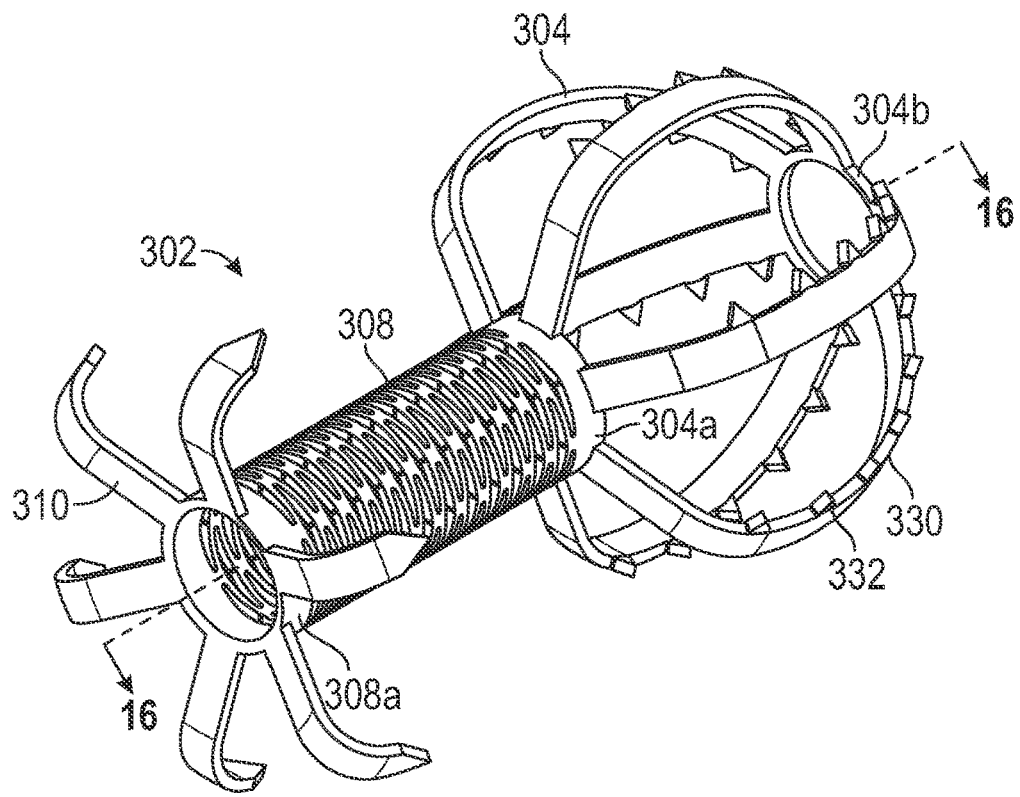
FIG. 15 shows another embodiment of an implant device wherein the contact member is in a second, expanded state, the retention member is in a second, contracted state, and the securing element is in a second, open state.
Figure 16:
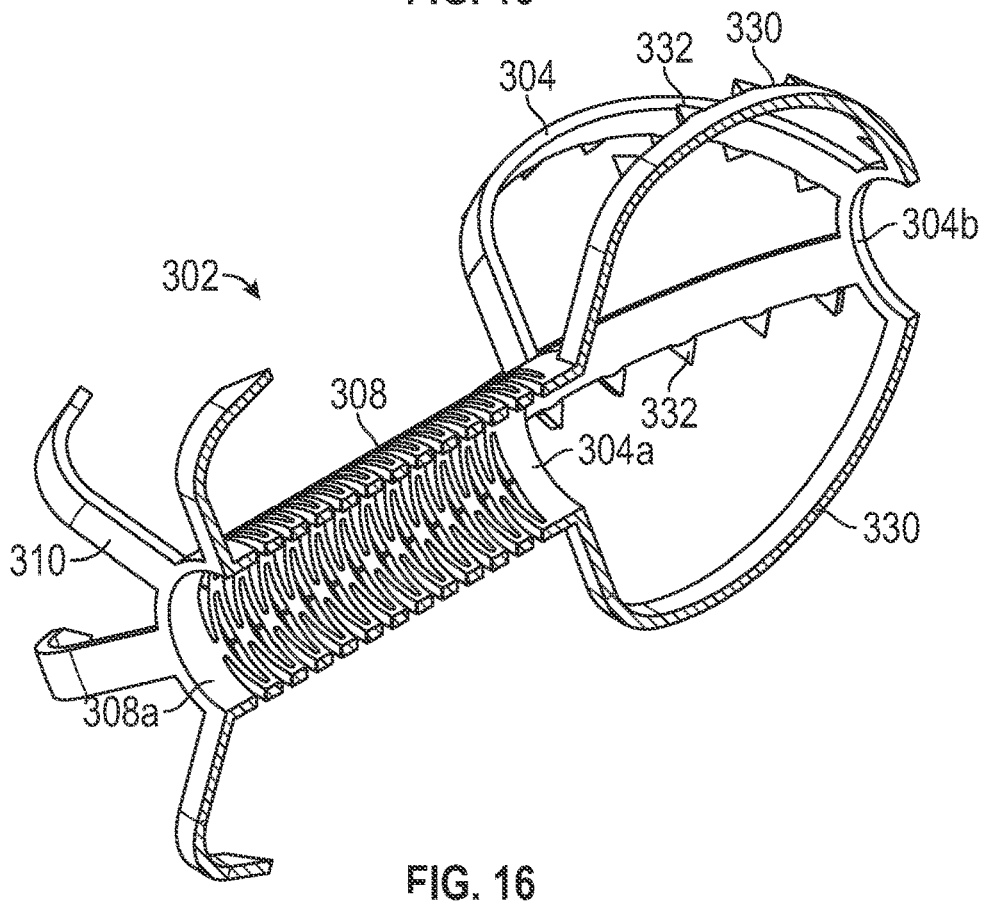
FIG. 16 is a section view of the treatment system shown in FIG. 15, taken through line 16-16 of FIG. 15.

FIG. 15 shows another embodiment of an implant device 302 wherein the contact member 304 is in a second, expanded state, the retention member 308 is in a second, contracted state, and the securing element 310 is in a second, open state. In any embodiments disclosed herein, any components, features, or other details of the treatment system 300 or implant device 302 can have any of the components, features, or other details of any other treatment system or implant device embodiments disclosed herein, including without limitation any of the embodiments of the treatment system 100, 200 or implant device 102, 202 described above, in any combination with any of the components, features, or details of the treatment system 300 or implant device 302 disclosed below. Similarly, any components, features, or other details of any of the other treatment system or implant device embodiments disclosed herein can have any of the components, features, or other details of any embodiments of the treatment system 300 or implant device 302 disclosed herein in any combination with any of the components, features, or details of the treatment system and/or implant device.

In any embodiments, a length of the retention member (including retention member 308) and/or a distance between the securing element and the contact member can be adjusted or varied beyond what is shown and described, for example to accommodate differing anatomy sizes and characteristics of the cavity and/or the space outside of or adjacent to the cavity, or to accommodate differing amounts or thicknesses of cavity tissue that has been gathered or twisted up. For example and without limitation, in some embodiments, the length of the retention member, or the distance between the securing element and the contact member, can be approximately the same as a length of the contact member when the retention member is in a relaxed or collapsed state (e.g., in the second state), or can be approximately one-half of the length of the contact member when the retention member is in the second state, or between one-quarter and one-half of the length of the contact member when the retention member is in the second state, or otherwise.

In some embodiments, the contact member 304 can have an annular proximal end portion 304a wherein all of the arms or struts 330 (six being shown) of the contact member 304 extend distally away from the proximal end portion 304a. Additionally, in some embodiments, the contact member 304 can have an annular distal end portion 304b wherein all of the arms or struts 330 can be coupled with the annular distal end portion 304b. In some embodiments, the contact member 304 can be laser cut from a hypotube, or can be formed from different components and welded, brazed, or otherwise coupled together. Each of the strut members 330 can be preformed into a curved shape (which can have a rounded or bulbous shape) and formed such that the strut members 330 are biased to expand to the second state when no external restraint or constraint is applied to the outside surface of the contact member 304. The struts 330 can have any form of tissue anchors 332 on the struts or attached to the struts, such as any of the tissue anchors 118 described above.

In some embodiments, the contact member 304, the retention member 308, and the securing element 310 can be integrally formed, such as being cut from a single length of hypotube, or otherwise. For example and without limitation, the retention member 308 and the securing element can be laser cut from a single length of tube material, for example, from an elastic or shape memory material, and thereafter formed into the desired shape. In other embodiments, the contact member 304, the retention member 308, and/or the securing element 310 can be separately formed and welded, brazed, or otherwise joined together to form a single, unitary component. Because, in some embodiments, a distance between the contact member 304 and the securing element 310 can be large, for example and without limitation, greater than a length of the contact member when the contact member is in the second, expanded state, the contact member 304 can be advanced further distally into the cavity and then rotated so as to twist the opening of the cavity to cause the opening of the cavity to constrict around an outside surface of the retention member. The greater length of the retention member 310 can also accommodate a greater degree of twisting or rotation, or a greater number of rotations or twists of the cavity before the securing element is engaged.

An intermediary sleeve or tube (not shown) can be coupled with the securing element 310 and can be used to manipulate and control a position and/or an orientation of the securing element 310, including holding a proximal end portion 310a of the securing element in a fixed axial position while a distally directed force is exerted on the contact member 304 to maintain the retention member 310 in the first, extended state. Additionally, a core member (not shown) can engage a distal end portion 304b of the contact member 304b to allow a distally directed force to be exerted on the contact member 304. Pins, tabs, sutures, ties, protrusions, clips, depressions, detents, or other features can be used to selectively (i.e., reversibly) couple the contact member 304 to the core member.

After the desired degree of twisting of the cavity has been performed, the securing element 310 can be moved to the second, expanded state by, for example, advancing the securing element 310 out of a distal end of a tube of the delivery catheter and allowed to expand to the second state of the securing element. Thereafter, while maintaining the contact member 304 in the desired axial and rotational position (for example, the second rotational position), the securing element 310 can be advanced into the tissue that has constricted around an outside surface of the implant so as to secure the tissue in the twisted and/or constricted state. In some embodiments, this can be achieved or performed simply by holding the contact member in the desired position and allowing the retention member 308 to retract to its retracted or relaxed state, thereby causing the securing element 310 to advance into the tissue. When the deployment is complete, a user may disengage the core member from the contact member 304 so that the core member may be withdrawn. As with the other embodiments, the implant device 304 can be selectively biased or secured in the proximal direction relative to a delivery catheter, such as with a suture or thread 380 that extends through an inside of the catheter and loops around a pin, tab, or other feature of the implant device and released by disengaging or removing the suture or other retaining device.

Figure 17:
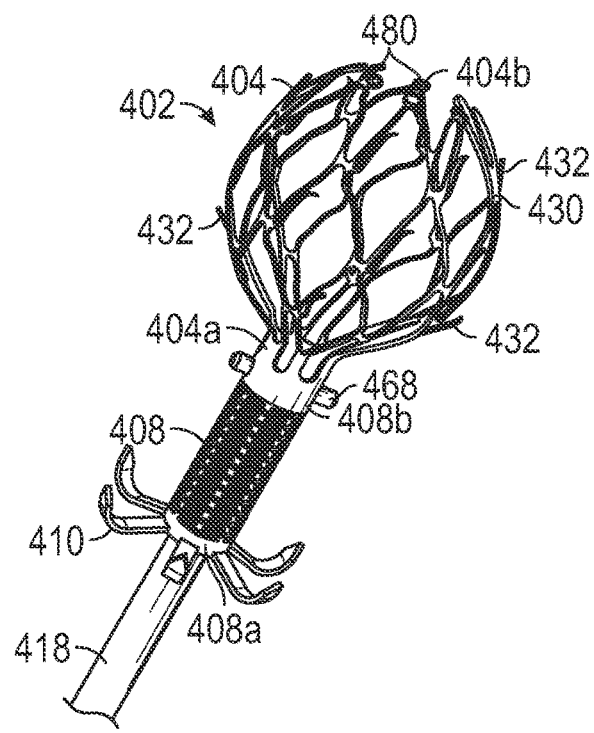
FIG. 17 shows another embodiment of a treatment system wherein the contact member is in a second, expanded state, the retention member is in a second, contracted state, and the securing element is in a second, open state.
Figure 18:
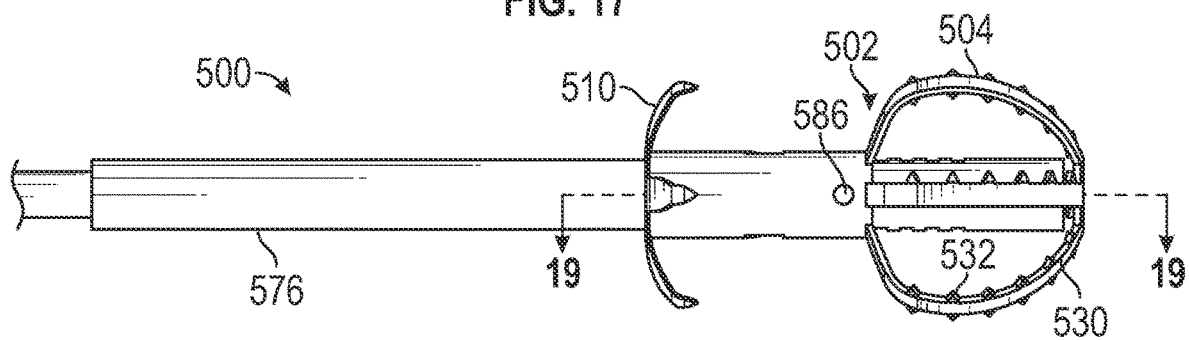
FIG. 18 shows a side view of another embodiment of a treatment system wherein the contact member is in a second, expanded state, the retention member is in a second, contracted state, and the securing element is in a second, open state.

FIG. 17 shows another embodiment of an implant device 402 wherein the contact member 404 is in a second, expanded state, the retention member 408 is in a second, contracted state (or in at least partially contracted or retracted state), and the securing element 410 is in a second, open state. Any embodiments of the treatment system 400 or implant device 402 can have any of the components, features, or other details of any other treatment system or implant device embodiments disclosed herein, including without limitation any of the embodiments of the treatment system 100, 200, 300 or implant device 102, 202, 302 described above, in any combination with any of the components, features, or details of the treatment system 400 or implant device 402 disclosed below. Similarly, any components, features, or other details of any of the other treatment system or implant device embodiments disclosed herein can have any of the components, features, or other details of any embodiments of the treatment system 400 or implant device 402 disclosed herein, in any combination, with any of the components, features, or details of the treatment system or implant device embodiments disclosed herein.

The contact member 404 can have an annular proximal end portion 404a and a distal portion 404b having a plurality of openings or rings 480. The struts or links 430 of the contact member 404 can form a web-like pattern so as to form a curved, bulbous, elongated bulbous, spherical or other shaped contact member. The struts 430 can have a plurality of tissue anchors or protrusions 432 coupled with the struts or links 430 at a plurality of locations about the contact member 404, such as any of the tissue anchors 118 described above. As in any of the embodiments disclosed herein, the tissue anchors 432 can be, but are not required to be, integrally formed with the struts 430. The struts or links 430 can form a generally diamond shaped pattern about the surface of the contact member. The contact member 404 can have a generally spherical or bulbous shape.

Additionally, with reference to FIG. 17, a pin or cross member 468 can be coupled with the implant device 402, for example and without limitation, at a distal end 408b of the retention member 408, or between the retention member 410 and the contact member 404. The pin 468 can be configured to engage an end portion of a core member 418 of the catheter, or a feature formed within a distal end portion of the core member of the catheter to selectively couple the implant device 402 with the core member of the catheter, just as with the other embodiments disclosed herein.

Additionally, similar to the other embodiments of the system disclosed above, some embodiments of the implant device 402 can have a suture or thread 480 that loops around or otherwise engages the pin 468, thereby permitting a user to retract or withdraw the suture to pull the implant device 402 proximally relative to the core member 418. After removing the biasing force from the suture 480, the core member 468 can be withdrawn relative to the implant device 402. This may be done after the implant and its securing element have been fully deployed.

In some embodiments, the contact member 404, the retention member 408, and/or the securing element 410 can be integrally formed, such as being laser cut from a single length of hypotube, or otherwise. For example and without limitation, the retention member 408 and the securing element can be laser cut from a single length of tube material, for example, from an elastic or shape memory material, and thereafter formed into the desired shape. In other embodiments, the contact member 404, the retention member 408, and/or the securing element 410 can be separately formed and welded, brazed, or otherwise joined together to form a single, unitary component. Because, in some embodiments, a distance between the contact member 404 and the securing element 410 can be large, the contact member 404 can be advanced further distally into the cavity and then rotated so as to twist the opening of the cavity to cause the opening of the cavity to constrict around an outside surface of the retention member. The greater length of the retention member 410 can also accommodate a greater number of rotations or twists of the cavity before the securing element is engaged.

An intermediary sleeve or tube (not shown) can be coupled with the securing element 410 and can be used to manipulate and control a position and/or an orientation of the securing element 410, including holding a proximal end portion 410a of the securing element in a fixed axial position while a distally directed force is exerted on the contact member 404 to maintain the retention member 410 in the first, extended state. Deployment of the device 402 can include any combination of the steps described with respect to any of the other embodiments disclosed herein.

FIGS. 18-21 show another embodiment of a treatment system 500 having an implant device 502 wherein the contact member 504 is in a second, expanded state, the retention member 508 is in a second, contracted state, and the securing element 510 is in a second, open state. Any embodiments of the treatment system 500 or implant device 502 can have any of the components, features, or other details of any other treatment system or implant device embodiments disclosed herein, including without limitation any of the embodiments of the treatment system 100, 200, 300, 400 or implant device 102, 202, 302, 402 described above, in any combination with any of the components, features, or details of the treatment system 500 or implant device 502 disclosed herein. Similarly, any components, features, or other details of any of the other treatment system or implant device embodiments disclosed herein can have any of the components, features, or other details of any embodiments of the treatment system 500 or implant device 502 disclosed herein, in any combination, with any of the components, features, or details of the treatment system or implant device embodiments disclosed herein.

The contact member 504 can have a plurality of struts or links 530 that can have a plurality of tissue anchors 532 thereon at a plurality of locations about the contact member 504, such as any of the tissue anchors 118 described above. As in any of the embodiments disclosed herein, the tissue anchors 532 can be, but are not required to be, integrally formed with the struts 530. The contact member 504 can have a generally spherical or bulbous shape, or the shape of any of the other embodiments disclosed herein.

Similar to other embodiments described above, any embodiments of the treatment system 500 can have a suture or thread 580 that extends through an inside of the core member 518 (such as through a lumen of the core member 518) and loops around a pin 568 or other retention member that is coupled with the contact member 504, thereby permitting a user to retract or withdraw the suture 580 to pull the contact member 504 proximally relative to the securing element 510 and to keep the implant 502 engaged with the delivery catheter. In this configuration, both ends of the suture 580 can extend from a proximal end of the device 500 such that a practitioner can grasp both ends of the suture 580 to exert a proximally directed force around the pin 568 to pull the contact member 504 toward the securing element 510 and to keep the pin 568 positioned within a slot 570 of the core member 518. Additionally, a slot 574 formed in the cylindrical body portion 572 of the securing element 510 can be sized so that the cylindrical body portion 572 of the securing element 510 can be moved axially in a proximal and distal direction relative to the pin 568, between a proximal end 574a of the slot 574 and a distal end 574b of the slot 574. Thus, the pin 568 and suture 580 can be used to bias or force the implant 502 to remain in contact with the catheter (for example, in contact with the core member 518 or the slot 570 formed in the core member) and to permit the user to move the securing element 510 from the first position to the second, engaged position (as shown in FIGS. 18-21).

Figure 19:
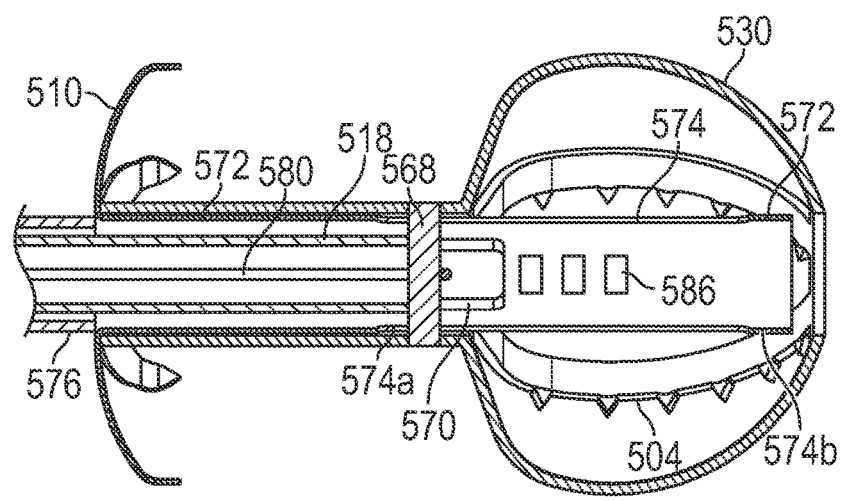
FIG. 19 is a section view of the treatment system shown in FIG. 18, taken through line 19-19 of FIG. 18.
Figure 20:
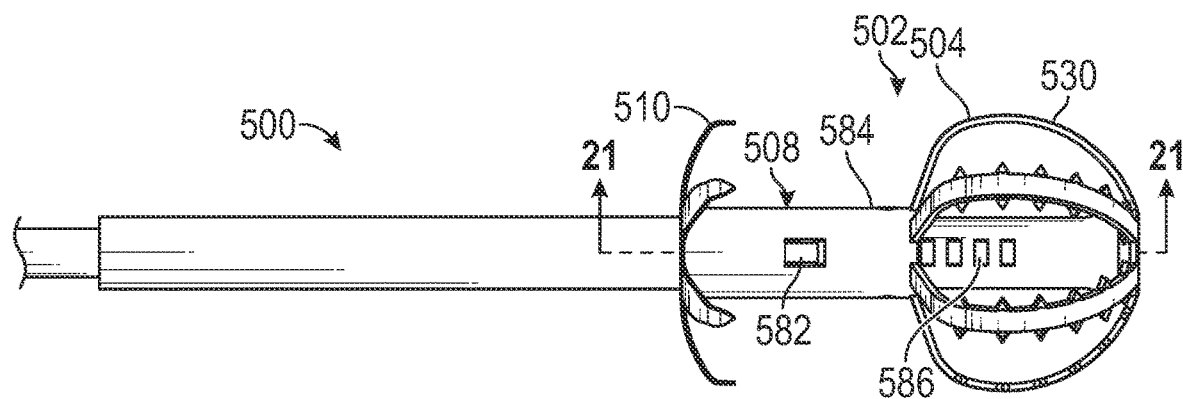
FIG. 20 is another side view of the treatment system shown in FIG. 18.
Figure 21:
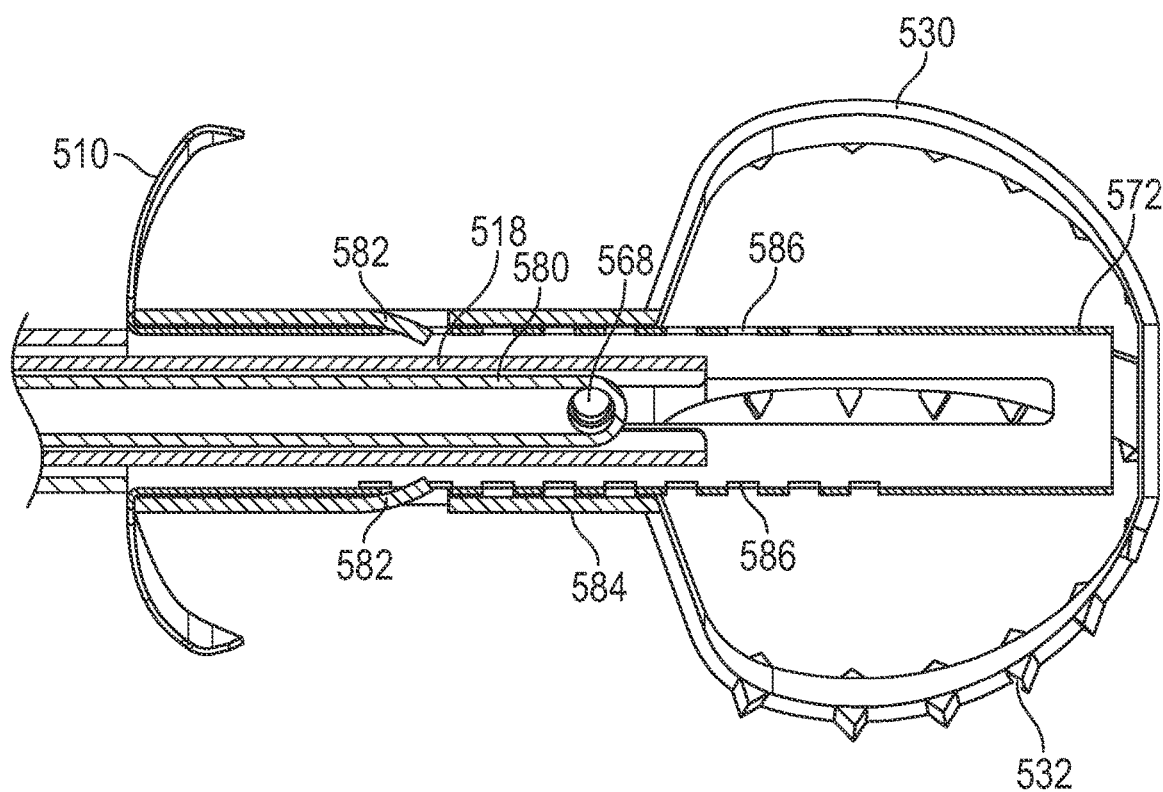
FIG. 21 is a section view of the treatment system shown in FIG. 18, taken through line 21-21 of FIG. 20.

In some embodiments, if the contact member 504 is maintained in a fixed position using the catheter or the core member 518, the user can move the securing element 510 from the first position to the second position by pulling back on or withdrawing the suture 580 (again, while the contact member 504 is held in a fixed position within the cavity) and advancing an outer tube 576 of the deliver catheter in a distal direction so as to push the securing element 576 distally. This would be done after the desired level of twisting of the cavity has been achieved by torqueing or twisting the core member 518 or other portion of the catheter. With reference to FIG. 19, this can, in some embodiments, cause the securing element 510 and body portion 572 of the securing element to advance distally relative to the contact member 504, thereby forcing the securing element into the tissue of the cavity or the tissue adjacent to the cavity or outside of the cavity so as to hold the tissue in the closed or contracted position.

Additionally, any embodiments of the device can be configured such that, as the securing element 510 is advanced into the second position, wherein the securing element 510 engages with the tissue and holds the cavity in an occluded or closed position, a retention member can be used to prevent the securing element from moving away from the second position toward the first position, thereby maintaining the position of the securing element and maintaining the occlusion in the cavity. For example and without limitation, one or more tabs 582 formed on or coupled with a body portion 584 of the contact member 504 can be biased to deflect into or engage with a respective depression or opening 586 of a plurality of depressions or openings 586 so as to prevent or inhibit the securing element 510 from moving back toward the first position relative to the contact member 504. The tabs 582 (which can be any other type of securing feature, such as ball and detent, or a zip tie type securing feature, or otherwise) can be configured such that the securing element 510 can freely move from the first, expanded position to the second, collapsed position, and to selectively prevent or inhibit movement from the second position to the first position, thereby essentially securing the securing element in the second position. Further, in any embodiments disclosed herein, the securing element and contact member can be held together using one or more sutures, wires, pins, or other components or fasteners, including, for example and without limitation, a suture with a slip knot which can be cinched during deployment. The suture can then be trimmed to length during final deployment, holding the securing element and contact member together to maintain the cavity in a closed or constricted state. Thereafter, the suture 580 can be removed, and the remaining components of the deployment device can be withdrawn from the patient's body, leaving the implant 502 in place.

In some embodiments, the implant device 502 can be configured such that the ratchet or retention mechanism formed by engagement of the tabs 582 and openings 586 is reversible or releasable, so that the securing element can be moved from the second to or toward the first position, for example, to disengage the securing element from the tissue for repositioning, for re-twisting the cavity, or otherwise. For example, some embodiments of the implant device 502 can be configured such that rotating or twisting the securing element (and, hence, the one or more tabs 582) relative to the body portion 584 of the contact member 504 so that the tabs 582 disengage the openings 586. Additionally, in some embodiments, the tabs can be positioned on the body portion 584 of the contact member 504 and the openings can be formed in a body portion of the securing element 510. Further, tabs can be formed in both directions so that the securing element can ratchet or be selectively securable in both axial movement directions. Further, in any embodiments disclosed herein, the tabs can be formed and configured so that the tabs can be moveable from a securing position or state to a non-securing (or sliding) state. Examples of these embodiments will be described below.

FIG. 22A shows another embodiment of a treatment system 600 having an implant device 602 wherein a contact member 604 is in a second, expanded state and a securing element 610 is in a first, retracted or pre-deployment state. FIG. 23 shows the embodiment of the implant device 602 wherein the securing element 610 has been moved to the second, deployed or locked state. FIGS. 24-35 illustrate an embodiment of a deployment method for the embodiment of the treatment system 600 illustrated in FIGS. 22-23. Any embodiments of the treatment system 600 or implant device 602 can have any of the components, features, or other details of any other implant device embodiments disclosed herein, including without limitation any of the embodiments of the implant device 100, 200, 300, 400, 500 described above, in any combination with any of the components, features, or details of the treatment system 600 or implant device 602 disclosed below. Similarly, any components, features, or other details of any of the other treatment system or implant device embodiments disclosed herein can have any of the components, features, or other details of any embodiments of the treatment system 600 or implant device 602 disclosed herein, in any combination, with any of the components, features, or details of the treatment system or implant device embodiments disclosed herein.

With reference to FIGS. 22A-22B, the securing element 610 can have a body portion 611 that can have a curved or helical (or corkscrew) shape that can extent from a proximal end portion 610a of the securing element 610 to a distal end portion 610b of the securing element 610, and can have a pointed distal tip 612 at the distal end portion 610b of the securing element 610 that can engage with (or, in some embodiments, penetrate at least partially through) the tissue of the cavity and/or the tissue of the space outside of or adjacent to the cavity after the contact member 604 has been rotated to the second position, thereby securing the tissue and closing or occluding the opening of cavity about the implant device, such as about a body portion 614 that is integral with or coupled with the contact member 604 or other portion of the implant device.

The securing element 610 can define an axial opening 615 therethrough. In some embodiments, the opening 615 can be larger than a distal portion of an inner core member of the catheter and/or a body portion 614 of the implant, so that a body portion 611 of the securing element 610 wraps around or curves around (helically or otherwise) and/or is rotatable around the inner core member of the catheter and/or the body portion 614 of the implant.

Figure 23A:
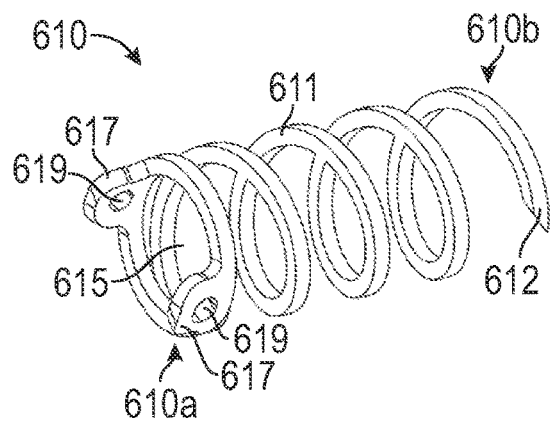
FIG. 23A shows an isometric view of another embodiment of a securing element.
Figure 23B:
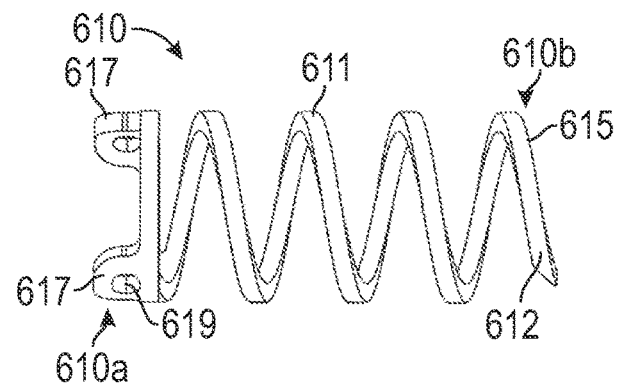
FIG. 23B shows a side view of the embodiment of the securing element shown in FIG. 23A.
Figure 23C:
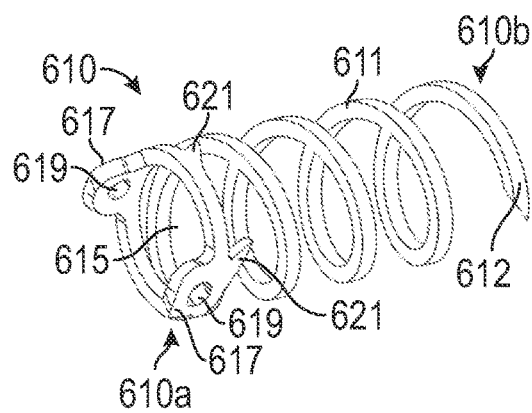
FIG. 23C shows an isometric view of another embodiment of a securing element.
Figure 23D:
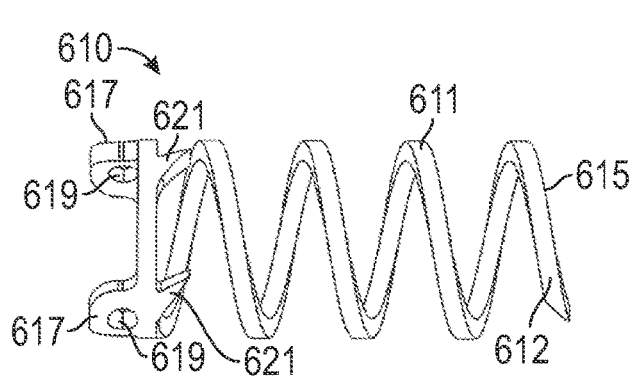
FIG. 23D shows a side view of the embodiment of the securing element shown in FIG. 23C.

FIGS. 23A-23B show another embodiment of a securing element 610 that can be used with any implant or delivery system embodiments and/or treatment methods disclosed herein. In any embodiments, a cross-section of the body portion 611 can be round, square (as shown), ovular, or have any other desired shape. In any embodiments, the body portion 611 can have from 2 to 15 or more coils (i.e., complete revolutions), or from 3 to 10 coils, or from 4 to 6 coils and can terminate at a distal end portion 610b of the securing element 610 in a sharp point, a blunt end, one or more tissue anchors or barbs, or otherwise. Additionally, any embodiments of the securing elements disclosed herein can have tissue anchors or barbs (not shown) along a length of the body portion 611 or body portions 611, in the embodiments having two or more body portions, such as described below, to engage with the tissue and prevent or inhibit the securing member 610 from backing out of the tissue after the securing element 610 has been advanced into such tissue. A proximal end portion 610a of the securing element 610 can have flanges 617, openings 619, and/or other features configured to connect the securing element 610 to the other portions of the implant 602.

Additionally, in any embodiments disclosed herein, the securing element 610 can also have rotational or axial lock features that can secure the securing element in a desired rotational position and/or desired axial position and/or inhibit the counter rotation of the securing element. The rotational or axial lock can be selectively reversible so that a user to return the securing element to a freely movable state, as desired. For example and without limitation, with reference to FIGS. 23C-23D, any embodiments of the securing elements disclosed herein can have one or more or a plurality of tissue anchors or barbs 621 extending away from a proximal end 610a of the securing element 610 that can improve the grip of the securing element in the target tissue, and/or prevent or inhibit the securing member 610 from backing out of the tissue after the securing element 610 has been advanced into such tissue. In any embodiments, the tissue anchors or barbs 621 can be axial facing, radially facing, or at an angle relative to the axial direction of the securing element 610. The tissue anchors or barbs 621 can be angled or otherwise configured to easily enter the tissue, and have a perpendicular face or otherwise be configured to engage with and/or lock with the tissue to prevent the counter-rotation of the securing element 610.

Figure 23E:
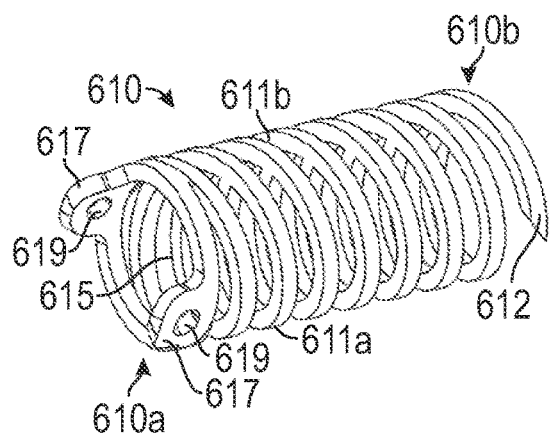
FIG. 23E shows an isometric view of another embodiment of a securing element.
Figure 23F:
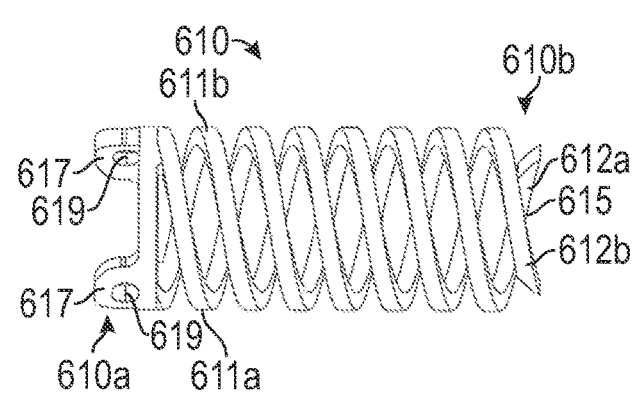
FIG. 23F shows a side view of the embodiment of the securing element shown in FIG. 23E.

Further, with reference to FIGS. 23E-23F, any embodiments of the securing elements disclosed herein can have two or more or a plurality of body portions 611 extending away from a proximal end 610a of the securing element. The embodiment of the securing element 610 shown in FIGS. 23E-23F has a first body portion 611a and a second body portion 611b that are both helically shaped, have the same or similar pitch, and can both extend a full length of the securing element 610. In other embodiments, one of the body portions 611 can have a different length (e.g., be shorter) than the other body portion 611. Additionally, in any embodiments disclosed herein, the one or more body portions 611 can have a pitch that changes (increases or decreases) along a length thereof from a proximal portion to a distal portion of the securing element. A body portion 611 having a pitch that decreases along a length of the securing element (such that the spacing increases along a length of the body portion) can result in the tissue between the coils being compressed more near a proximal end portion of the securing element than near a distal end portion of the securing element. In some embodiments, this may increase the retaining force of the securing element in the tissue. The first body portion 611a can have a distal end portion 612a and the second body portion 611b can have a distal end portion 612b.

As mentioned, in some embodiments, the securing element 610 can have two or more curved or helical (or corkscrew) shaped body portions 611, each of which can have a pointed distal tip that can engage with (or, in some embodiments, penetrate at least partially through) the tissue of the cavity and/or the tissue of the space outside of or adjacent to the cavity after the contact member has been rotated to the second position. In any embodiments disclosed herein, the securing element having a helical shape (such as the embodiment of the securing element 610 shown in FIGS. 22A-22B) can have two helically shaped body portions 611 that can be each configured to penetrate and engage the tissue that has constricted around a portion of the implant. In any embodiments, including the single and double helical securing element embodiments, the body portion or portions 611 can be long enough to engage the contact member, or shorter and just engage all or just a proximal portion of the tissue of the cavity and/or the tissue of the space outside of or adjacent to the cavity, such as from approximately 1 mm to approximately 2 mm of the tissue of the cavity and/or the tissue of the space outside of or adjacent to the cavity, or from approximately 2 mm to approximately 5 mm or more of the tissue of the cavity and/or the tissue of the space outside of or adjacent to the cavity.

Further, in any embodiments, the one or more body portions 611 may define a cylindrical shape along a length of the securing member 610, as shown, define a conical shape along a length of the securing member 610, or otherwise. For example and without limitation, in any embodiments, the one or more body portions 611 may define a conical shape that increases along a length of the securing member 610 so that the opening 615 is larger at the distal end portion 610b of the securing element 610. The conical shape can result in the tissue being gathered wide and brought together (i.e., radially inwardly) as the securing element 610 is advanced into the tissue of the cavity and/or the tissue of the space outside of or adjacent to the cavity.

With reference to FIG. 22B, the securing element 610 (which can be any of the securing element embodiments or have any combination of any of the features of the securing element embodiments disclosed herein) can be rotated (such as in a corkscrew fashion) and advanced so as to penetrate into and/or pass through the tissue of the cavity and/or the tissue of the space outside of or adjacent to the cavity that has gathered and/or constricted about the body portion 614 or other portion of the implant device 602. In this configuration, the securing element 610 is configured to be rotatable relative to the contact member 604 so that the securing element 610 can be rotated and passed through the tissue of the cavity and/or the tissue of the space outside of or adjacent to the cavity while the cavity is held generally stationary in the second rotational position by holding the contact member 604 in the stationary position. In any embodiments, a sleeve or other component of the catheter or delivery system can be coupled with the securing element (including, without limitation, securing element 610) to enable a user to move the securing element between a first state and a second state (which should be interpreted to also include moving from the second state to the first state), to rotate the securing element in either direction, to move the securing element between a first position and a second position, and/or to otherwise manipulate the securing element. In some embodiments, the catheter or delivery system can be configured to perform these operations independently of any other movements or operations of the catheter so that, for example, the securing element can be axially advanced toward the contact member while the contact member is held in a fixed position by the catheter.

The securing element 610 can thereby hold the tissue of the cavity and/or the tissue of the space outside of or adjacent to the cavity to hold the tissue of the cavity and/or the tissue of the space outside of or adjacent to the cavity in the constricted state about the implant device, so as occlude the cavity. Additionally, in some embodiments, as shown, the securing element 610 can be configured to also pass through one or more of the openings 620 that can be formed in or result in the contact member 604 when the contact member 604 is in the second, expanded state, thereby further securing the securing element 610 to the contact member 604 and preventing or inhibiting the contact member 604 from rotating toward the first position. In any embodiments, the securing element 610 and/or the contact member 604 can have one or a plurality of teeth, cleats, barbs, nubs, texture, studs, anchors or other tissue engaging features or anchor members about an outside surface of the securing element 610 to prevent or inhibit the securing element 610 from disengaging from the tissue of the cavity and/or the tissue outside of or adjacent to the cavity when in the second state. Further, in any embodiments, the securing element can be biased to the second positioned by a biasing member (not shown) such as an axially resilient member, or using one or more sutures, wires, ratchets, tabs and openings, or other securing features. However, in some embodiments, the engagement of the securing element 610 into the tissue of the cavity and/or the tissue outside of or adjacent to the cavity can be sufficient to secure the securing element 610 in the second position and maintain the cavity in the occluded state.

With respect to FIGS. 24-35, an embodiment of a deployment sequence will now be described. FIGS. 24-27 show the contact member 604 being advanced into the cavity. With reference to FIG. 27, the contact member 604 can be advanced to any desired depth, including to an end portion, of the cavity. In some embodiments, the contact member 610 can be advanced to the desired position relative to the cavity and then expanded to the second state so as to contact an inside surface or tissue of the cavity. Thereafter, the contact member 604 can be rotated in a first direction (represented by arrow A3 in FIGS. 28-29, which can be either the clockwise or counter-clockwise direction) toward the second position so as to twist the cavity in the first direction, as also indicated by arrow A3 in FIGS. 28-29, toward the second state. As described, the twisting can cause the opening of the cavity to constrict around a portion of a body of the implant device 602, so as to occlude the cavity from the LA, as shown in FIGS. 28-29.

Figure 30:
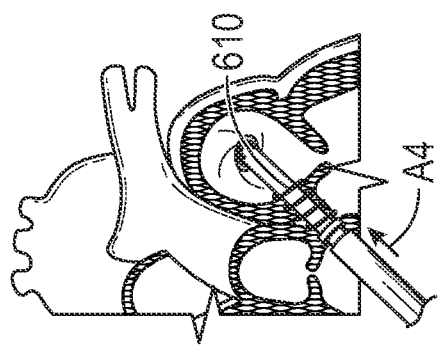
Figure 32:
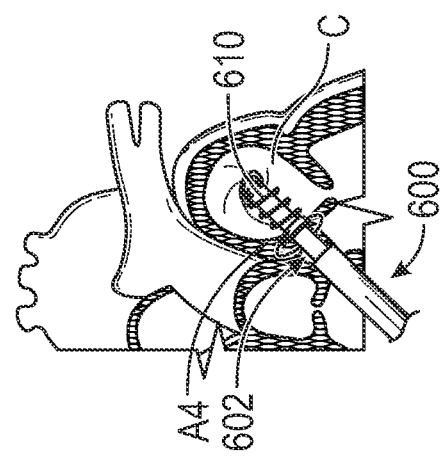
Figure 34:
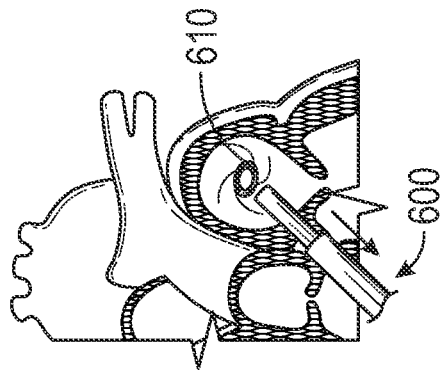
Figure 31:
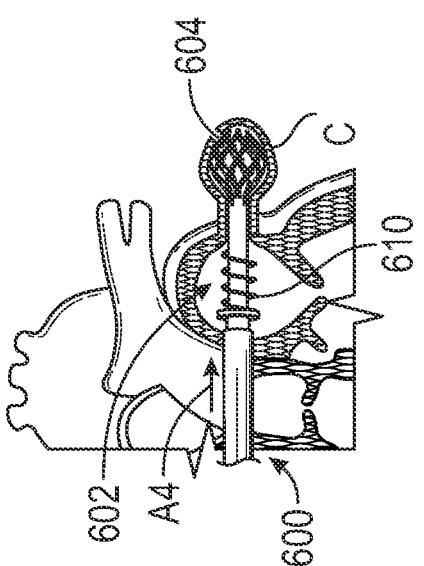
Figure 33:
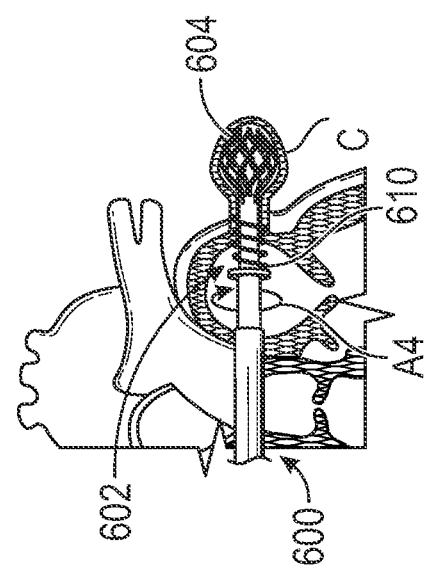
Figure 35:
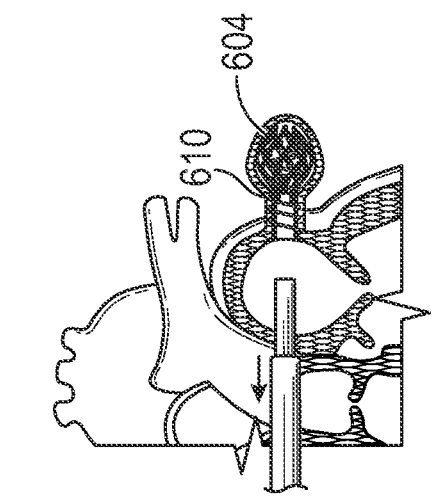

Thereafter, with reference to FIGS. 30-31, while maintaining the contact member 604 in the second rotational position and/or maintaining the tissue of the cavity and/or the tissue outside of or adjacent to the cavity in the occluded or constricted state and the cavity in the twisted position, the securing element 610 can be advanced distally (as indicated by arrow A4 in FIGS. 30-31) toward the tissue of the cavity and/or the tissue outside of or adjacent to the cavity that has constricted around the body of the implant device. Before a distal end of the securing element 610 reaches the tissue of the cavity and/or the tissue outside of or adjacent to the cavity, the securing element 610 can be rotated in a first direction (such as the rotational direction indicated by arrow A5 shown in FIGS. 32-33) while the securing element 610 is being advanced distally to cause the securing element 610 to penetrate into and/or engage with the tissue of the cavity and/or the tissue outside of or adjacent to the cavity that has constricted around the body portion of the implant device 602. In some embodiments, the securing element 610 can be advanced so as to penetrate completely through the tissue of the cavity and/or the tissue outside of or adjacent to the cavity, as shown in FIGS. 34-35. In some embodiments, the securing element 610 can be configured so as to engage and/or only partially penetrate into the tissue of the cavity and/or the tissue outside of or adjacent to the cavity. Thereafter, the implant device 602 can be released from the delivery catheter and the delivery catheter can be withdrawn from the space outside of or adjacent to the cavity, which can be the heart or any other organ or space within the body, as shown in FIGS. 34-35, leaving the cavity in the occluded position.

Figure 36:
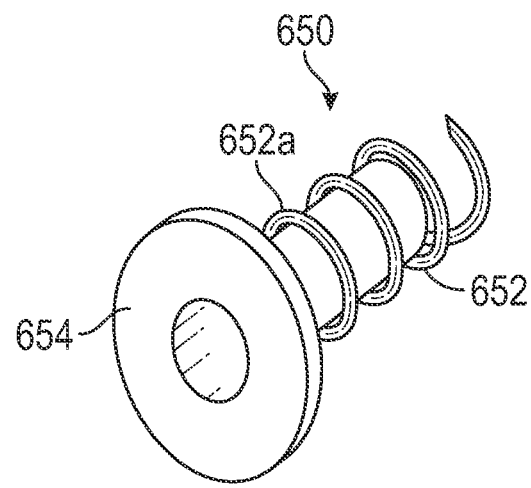
FIG. 36 shows another embodiment of an implant device wherein the retention member is engaging with a tissue surface surrounding an opening of the cavity.

FIG. 36 shows another embodiment of an implant device 650 having a different embodiment of a securing element 652 that can be used with any of the embodiments of the implant devices disclosed herein. As shown in FIG. 36, the securing element 650 can have a backing member 654 coupled with a proximal end 652a of the securing element 652 that can provide an additional seal against the tissue of the cavity and/or the tissue outside of or adjacent to the cavity when the securing element is in the second or deployed position.

Figure 37:
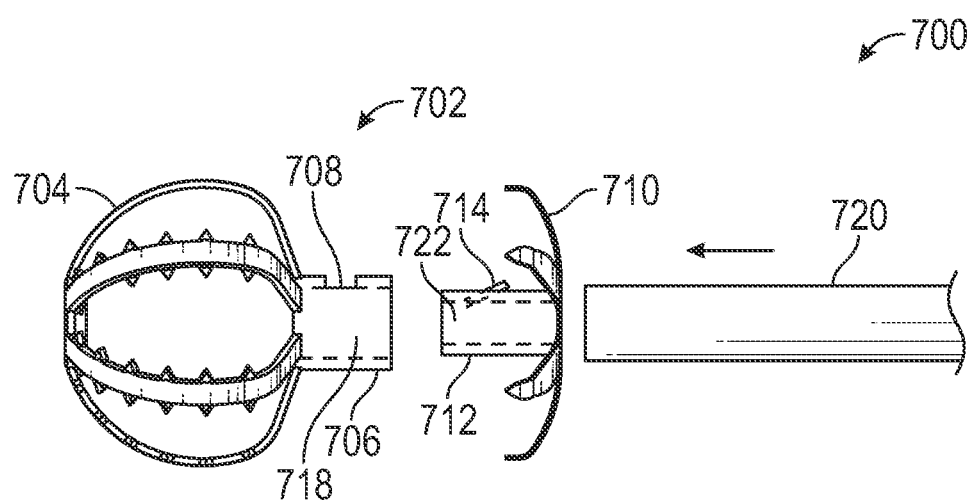
FIG. 37 shows another embodiment of a treatment system wherein a tab member of the securing element is in a first, engaged state.
Figure 38:
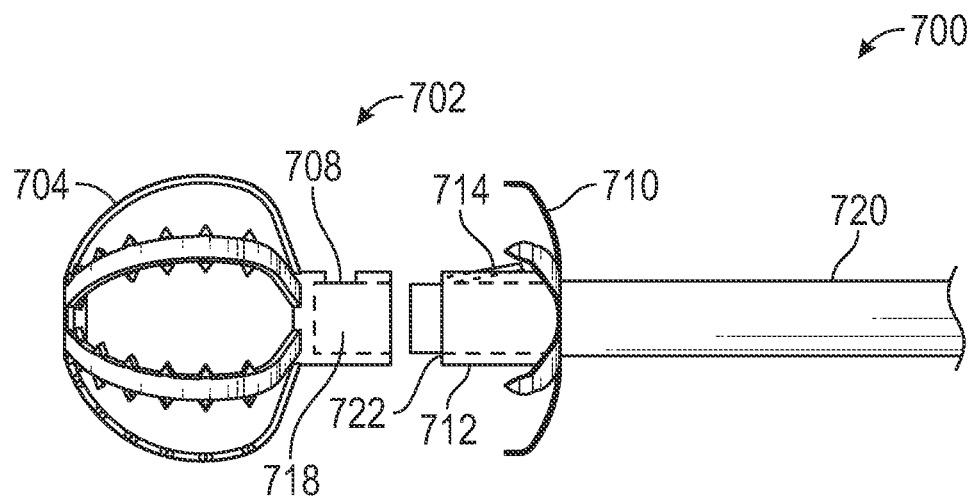
FIG. 38 shows the treatment system of FIG. 37, wherein the tab member is in a second, disengaged state.

FIGS. 37-38 show another embodiment of a treatment system 700 having an implant device 702 wherein the contact member 704 is in a second, expanded state, and the securing element 710 is in a second, open state. Any embodiments of the treatment system 700 or implant device 702 can have any of the components, features, or other details of any other treatment system or implant device embodiments disclosed herein, including without limitation any of the embodiments of the treatment system 100, 200, 300, 400, 500, 600 or implant device 102, 202, 302, 402, 502, 602 described above, in any combination with any of the components, features, or details of the treatment system 700 or implant device 702 disclosed below. Similarly, any components, features, or other details of any of the other treatment system or implant device embodiments disclosed herein can have any of the components, features, or other details of any embodiments of the treatment system 700 or implant device 702 disclosed herein, in any combination, with any of the components, features, or details of the treatment system or implant device embodiments disclosed herein.

In any embodiments, the contact member 704 can have a body portion 706 that can, but is not required to have, a cylindrical shape. An opening or recess 708 can be formed in the body portion 706 as part of a retaining element to retain the securing element 710 in a desired axial position relative to, or locked to, the coupling member 704. The securing element 710 can also have a body portion 712 that can, but is not required to have, a cylindrical shape. In some embodiments, the body portion 712 can extend into the body portion 706 of the contact member 704 even when the securing element 710 is in a first, retracted state. The body portion 706 can have an opening 708 extending therethrough, sized and configured to selectively receive the body portion 712 of the securing element 710. The body portion 712 can have an opening 722 extending therethrough, sized and configured to selectively receive a core member 720 of the delivery catheter of the treatment system 700.

Figure 39:
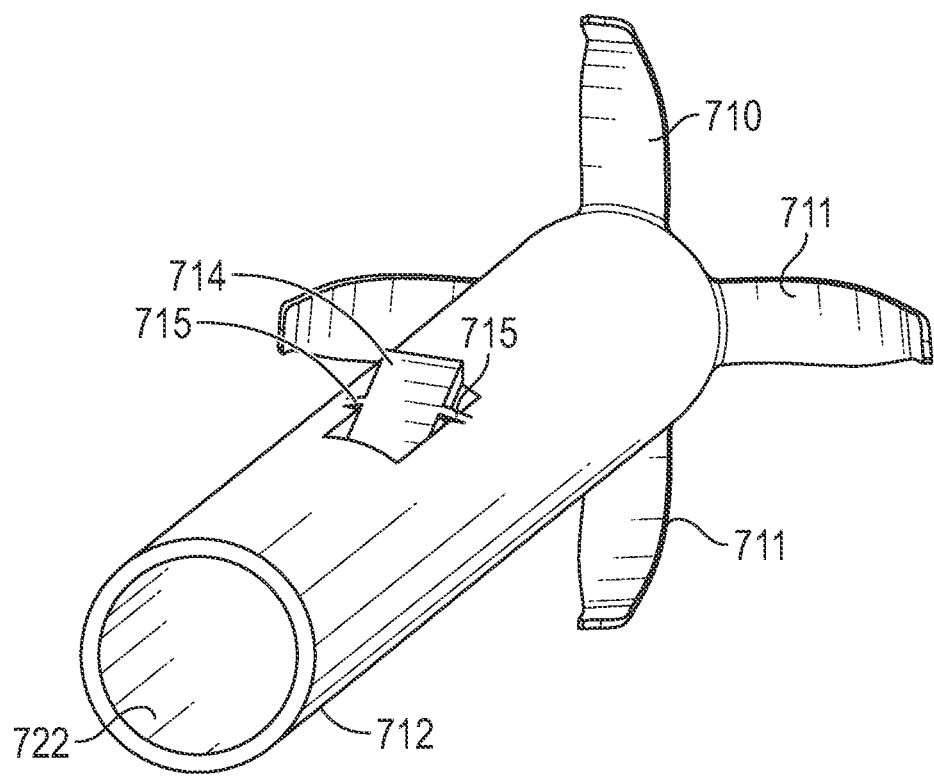
FIG. 39 shows the securing element of the treatment system of FIG. 37.

Additionally, with reference to FIG. 39, the securing element 710 can have a deflectable tab member 714 that can be movable or moved from a first, engaged position (as shown in FIG. 37) to a second, disengaged position (as shown in FIG. 38). The tab member 714 can be configured to rotate about a pin that can be coupled with the tab member 714 and the body portion 712, or can be configured to rotate about a thin strip of the material (referred to herein as a material strip 715) used to form the body portion 712 and/or the tab member 714. For example and without limitation, the body portion 712, the tab member 714, and the one or more material strips 715 (two being shown) can be integrally formed. Additionally, in some embodiments, the one or more arms 711 of the securing element 710 (four being shown) can also be integrally formed with the other features of the securing element 710. In some embodiments, the tab 714 can be biased toward the first, engaged position (as shown in FIGS. 37 and 39), but be physically deflectable or rotatable toward the second, disengaged position (as shown in FIG. 38) by advancing a core member 720 or other component through the opening 722 extending through the body portion 712 of the securing element 710. For example and without limitation, as shown in FIG. 38, the core member 720 can be advanced distally through the opening 722 of the securing element 710 to deflect or rotate the tab member 714, thereby moving the tab member 714 from the first, engaged position to the second, disengaged position.

When the tab member 714 is in the engaged position, the tab member 714 can engage with the opening 708 formed in the body portion 706 of the contact member to axially lock or couple the securing element 710 with the contact member 704, for example, after the contact member has twisted the cavity to a closed or occluded position or state, as described above. However, in some embodiments, if a user wishes to disengage or decouple the securing element 710 from the contact member 704, the user can achieve this by moving the tab member 714 to the second, disengaged position, such as, for example and without limitation, as described above, thereby disengaging the tab member 714 from the opening 708. Thereafter, the user can axially withdraw the securing element 710.

FIGS. 40-43 illustrate another embodiment of an implant device 732. Any embodiments of the implant device 732 can have any of the components, features, or other details of any other treatment system or implant device embodiments disclosed herein, including without limitation any of the embodiments of the treatment system 100, 200, 300, 400, 500, 600, 700 or implant device 102, 202, 302, 402, 502, 602 described above, in any combination with any of the components, features, or details of the implant device 732 disclosed below. Similarly, any components, features, or other details of any of the other treatment system or implant device embodiments disclosed herein can have any of the components, features, or other details of any embodiments of the implant device 732 disclosed herein, in any combination, with any of the components, features, or details of the treatment system or implant device embodiments disclosed herein.

Figure 40:
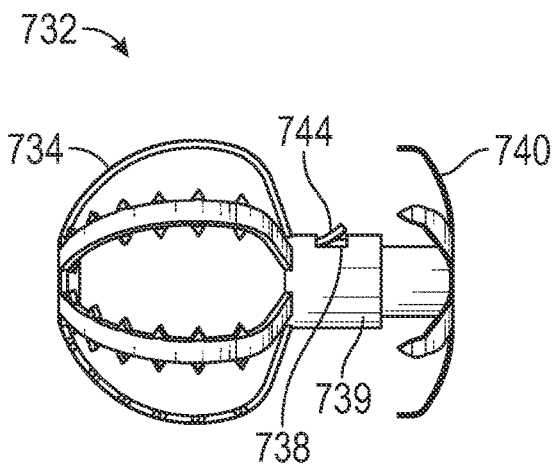
FIG. 40 shows the treatment system of FIG. 37, wherein the securing element is engaged with the contact member and the tab member of the securing element is in the first, engaged state.
Figure 41:
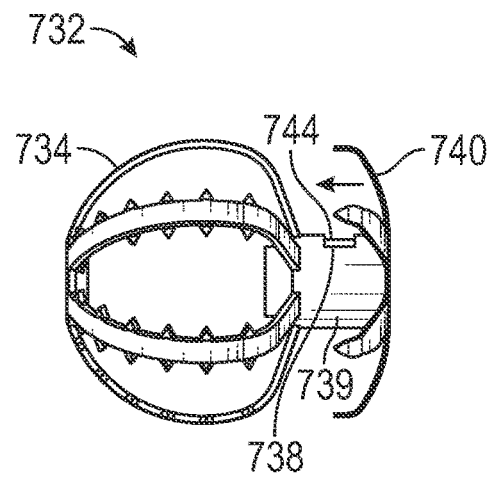
FIG. 41 shows the treatment system of FIG. 37, wherein the tab member of the securing element has been moved to the second, disengaged state by the axial advancement of a core member of the delivery system.
Figure 42:
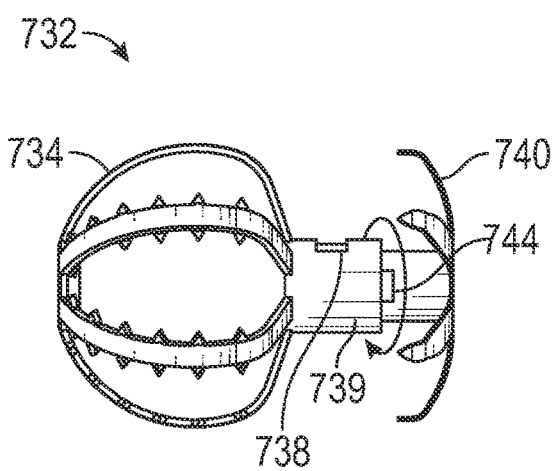
FIG. 42 shows the treatment system of FIG. 37, wherein the securing element has been rotated to misalign the tab member relative to the opening of the contact member and permit the withdrawal of the securing element from the contact member.
Figure 43:
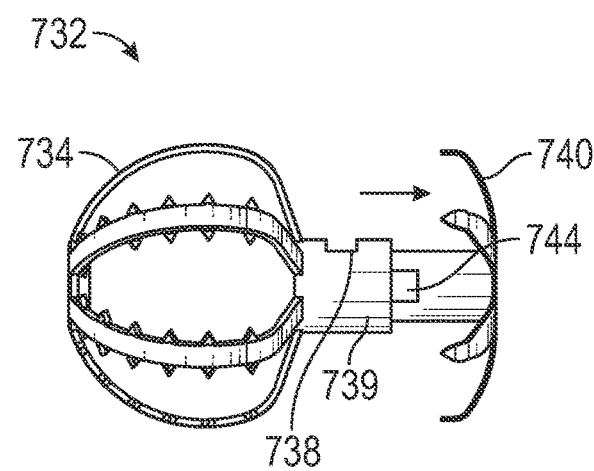
FIG. 43 shows the treatment system of FIG. 37, wherein the securing element has been withdrawn from the contact member.

As shown in FIG. 40, a deflectable tab member 744 of the implant device 732 is engaged with an opening 738 of the contact member 734, thereby causing the securing element 740 to be engaged with the contact member 734. In any embodiments, the deflectable tab member 744 can be movable or moved from a first, engaged position (as shown in FIG. 40) to a second, disengaged position (as shown in FIG. 41) by advancing the securing element 710 distally so that a body portion 739 of the contact member 734 causes the tab member 744 to deflect and move to the second, disengaged position, as shown in FIG. 41. Thereafter, the securing element 740 can be rotated in either direction (such as by 90 degrees) to a position in which the tab member 744 is not aligned with and therefore cannot engage with the opening 738, as shown in FIG. 42. The body portion 739 of the contact member 734 can hold the tab member 744 in the second, disengaged position while the securing element 740 is withdrawn away from or disengaged from the contact member, as shown in FIG. 43.

Figure 44A:
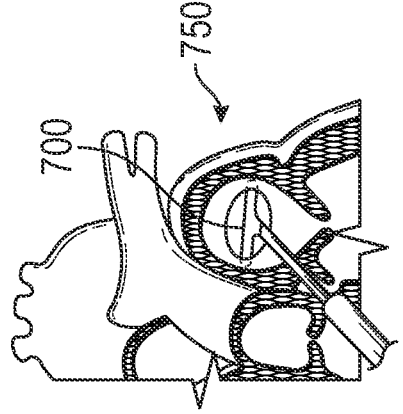
FIGS. 44A and 44B are a front view and a side view, respectively, of another embodiment of a treatment system configured to twist and close or occlude the cavity at the opening of the cavity.
Figure 45A:
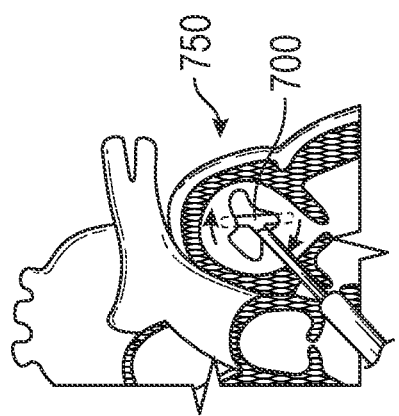
FIGS. 45A and 45B are a front view and a side view, respectively, of the treatment system of FIGS. 44A and 44B, showing the implant being used to twist the cavity to close or occlude the cavity at the opening.
Figure 46A:
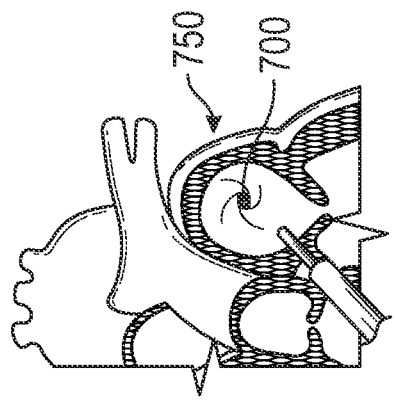
FIGS. 46A and 46B are a front view and a side view, respectively, of the treatment system of FIGS. 44A and 44B, showing the delivery device being removed from the implant device after the cavity has been occluded.
Figure 44B:
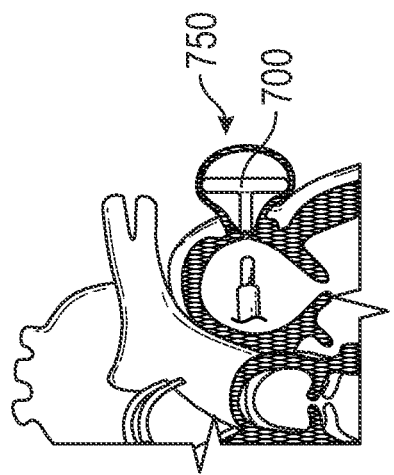
Figure 45B:
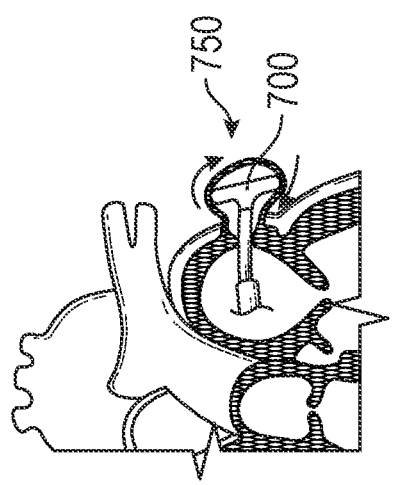
Figure 46B:
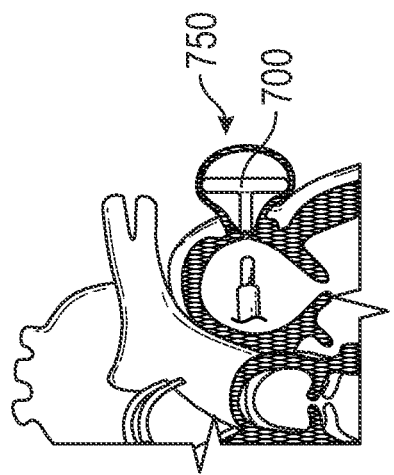
Figure 48A:
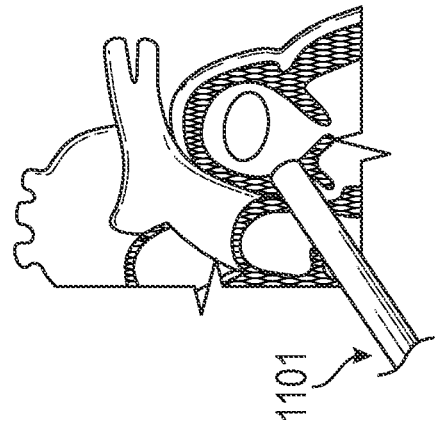
FIGS. 48A-48F show some stages or steps of an exemplifying deployment procedure of the expandable implant of FIGS. 47A-47F for treatment of a cavity.
Figure 48B:
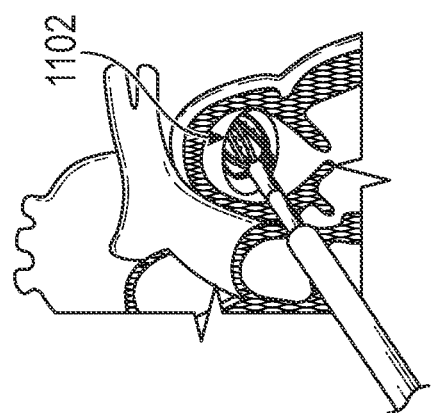
Figure 48C:
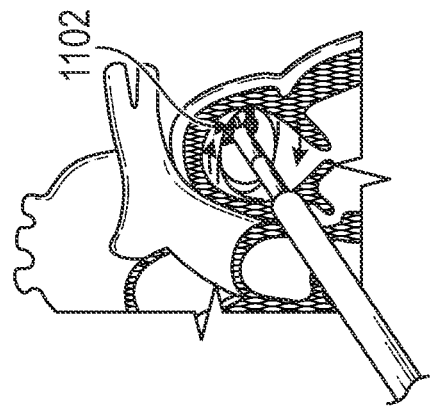
Figure 48D:
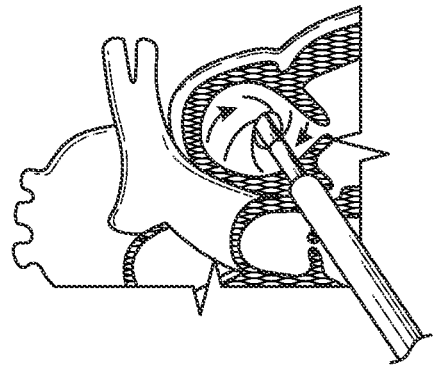
Figure 48E:
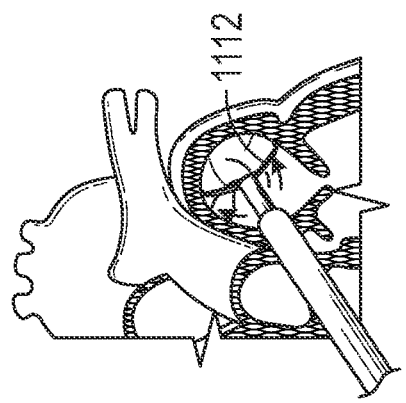
Figure 48F:
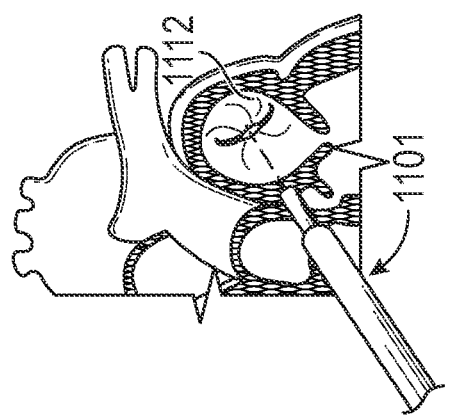

FIGS. 44A and 44B are a front view and a side view, respectively, of another embodiment of a treatment system 750 configured to twist and close or occlude the cavity at the opening of the cavity. FIGS. 45A and 45B are a front view and a side view, respectively, of the treatment system 750 of FIG. 44, showing the implant being used to twist the cavity to close or occlude the cavity at the opening. The opening of the cavity or the tissue of the cavity and/or the tissue of the space outside of or adjacent to the cavity that has constricted around the implant device can then be clipped or locked in the constricted state, as in any embodiments disclosed herein and using any securing features or components disclosed herein. FIGS. 46A and 46B are a front view and a side view, respectively, of the treatment system of FIG. 44, showing the delivery device being removed from the implant device after the cavity has been occluded.

In some embodiments, the steps of deployment and implantation can include, in any combination and in any combination with any other steps: (a) inserting catheter and implant device through an opening of the cavity; (b) rotating a contact member or other engaging component of the implant to twist the cavity, causing at least the opening of the cavity to collapse on itself, thereby closing or occluding the opening of the cavity; (c) clipping, holding, or securing the tissue of the cavity and/or the tissue outside of or adjacent to the cavity in the occluded or closed state; and/or (d) releasing and withdrawing the delivery catheter from the implant. As illustrated, the treatment system twists and closes the cavity at the opening, and then clip and hold that position, effectively closing the cavity. In some embodiments, the steps of deployment and implantation can include: Inserting catheter into middle of cavity opening, rotating the paddle of the implant to twist cavity and self-collapsing the cavity on itself, clipping and holding position to atrial wall, and releasing the delivery catheter from the implant.

FIGS. 47A-47F show another embodiment of a treatment system 1100 for closing or occluding an cavity having an embodiment of a delivery device 1101 and an embodiment of an expandable implant or implant 1102 for the cavity, in particular, showing the implant 1102 in a plurality of exemplifying expansion and deployment stages. The implant 1102 can have a body portion 1104 having a plurality of struts or arms 1106 that are expandable. The body portion 1104 can, in some embodiments, expand to an approximately spherical shape, or elongated spherical shape. The struts 1106 can each have a plurality of barbs or tissue anchors 1108 thereon (which can be or comprise any of the tissue anchors disclosed herein). Any embodiments of the implant disclosed herein can have a laser cut Nitinol body portion that is self-expanding and which is covered with micro-barbs.

The barbs 1108 can be configured to engage the tissue upon the twisting movement or motion of the body portion 1104 relative to an internal wall of the cavity after the body portion 1104 has been expanded from the first state to the second state, wherein, in the second state, the struts 1106 and barbs 1108 can be engaged with or in contact with the tissue on an inside wall of the cavity. Additionally, any embodiments of the implant 1102 can have one or more anchoring elements 1112 configured to engage with the tissue adjacent to or surrounding the cavity to prevent the implant 1102 from rotating back to the first rotational position after the implant 1102 has been rotated within the cavity to the second rotational position. In any embodiments, the anchoring elements 1112 can comprise two arms or members that can each engage a tissue surface and can each have a plurality of barbs thereon, configured to prevent the implant from rotating back to a first rotational position. FIGS. 48A-48E show some stages or steps of an exemplifying deployment procedure of the expandable implant 1102 of FIGS. 47A-47F as the implant 1102 is being deployed into a cavity.

FIGS. 49A-49G show an embodiment of an implant 1202 that can be used to close or substantially close a cavity. In some embodiments, the implant 1202 can be formed by laser cutting a tube of elastic material, such as Nitinol. The implant 1202 and any other implant embodiment disclosed herein can be self-expanding or mechanically expandable, such as using balloon expansion techniques. Further, any embodiment of the implant 1202 can have any of the same features, components, or details of any other implant embodiments disclosed herein in place of or in combination with any of the features, components, or other details of the embodiments of the implant 1202 disclosed herein. In some embodiments, the implant 1202 can have a contact member 1204 that can be covered with a plurality of micro-barbs or other tissue anchors 1208 and have a securing element 1212 (also referred to herein as an anchoring element) that can include a single folding clip anchor. The securing element 1212 can be configured to lock the implant 1202 in a fixed rotational position after the implant has rotated the cavity to the desired level of twist and closure or occlusion.

Figure 50A:
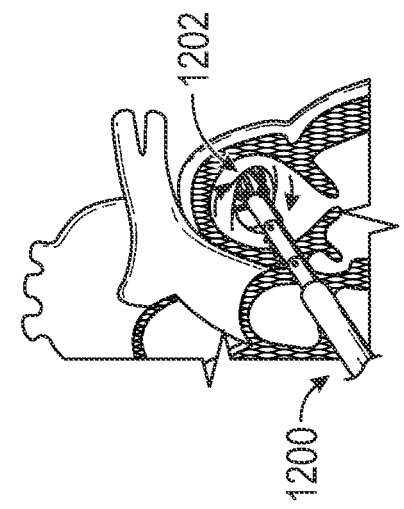
FIGS. 50A-50F show some stages or steps of an exemplifying deployment procedure of the expandable implant of FIGS. 49A-49G for treatment of a cavity.
Figure 50B:
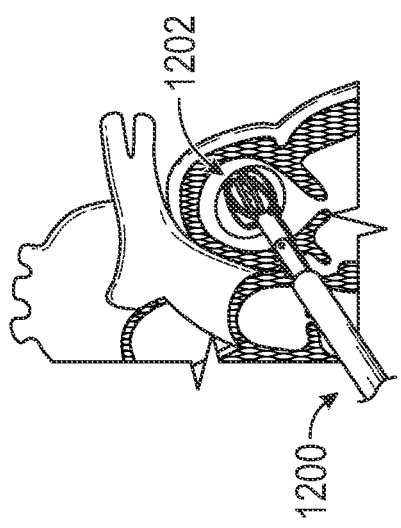
Figure 50C:
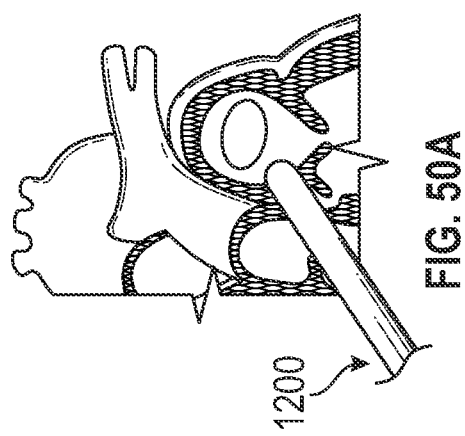
Figure 50D:
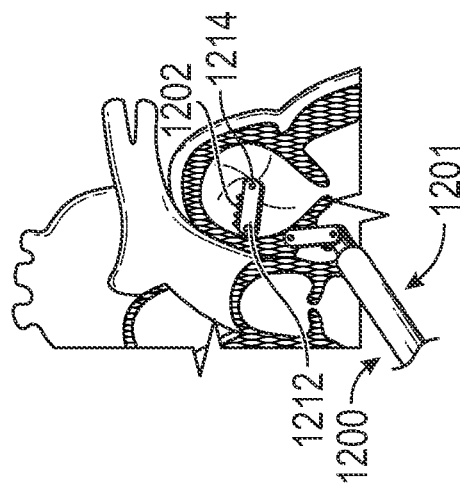
Figure 50E:
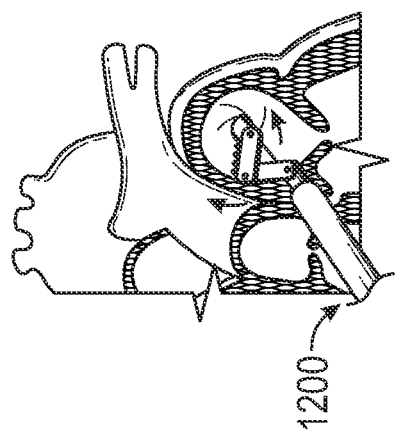
Figure 50F:
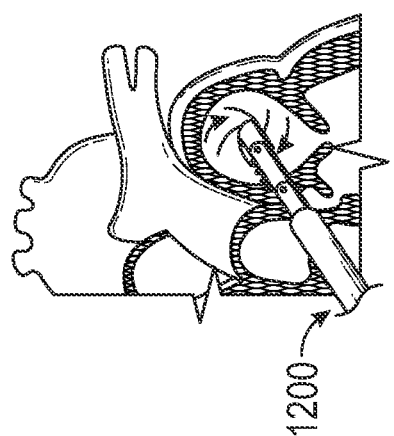

FIGS. 50A-50F show some exemplifying stages of an embodiment of a deployment procedure of the expandable implant 1202 of FIGS. 49A-49G as the implant 1202 is being deployed into a cavity. In any embodiments, the implant 1202 can be advanced into the cavity, expanded, and then rotated from a first rotational position to a second rotational position so as to twist the cavity and cause an opening and/or other tissue of the cavity to constrict or occlude about a portion of the implant 1202. The implant or any implant disclosed herein can be configured to be rotated clockwise (and can be rotated clockwise and/or counterclockwise during any procedures disclosed herein) to twist and close or substantially close the opening of the cavity or constrict the opening of the cavity about a portion of the implant 1202. After the desired level of occlusion is reached, the securing element 1212 can be rotated or folded (such as, for example and without limitation, about an axis or a hinge 1214) to a lateral side of the cavity so as to be approximately perpendicular to the axial centerline of the implant, and forced into engagement with the tissue adjacent to the cavity adjacent to the opening of the cavity to prevent unwinding of the implant and the opening of the cavity. A body portion of the securing element 1212 can also have tissue anchors 1216 thereon or coupled or integrally formed therewith that can engage with, penetrate, and/or grip the tissue of the cavity and/or the tissue outside of or adjacent to the cavity that has constricted as a result of the twisting of the cavity. In any embodiments disclosed herein, the securing element 1212 can be configured to be biased toward and/or securable in a second, locked state (such as is shown in FIG. 49G or FIG. 50F, using springs, shape memory material, sutures, ties, or other components. The delivery device can be disconnected from the implant and removed from the patient's body after deployment of the securing element 1212, as shown in FIG. 50F.

Figure 51:
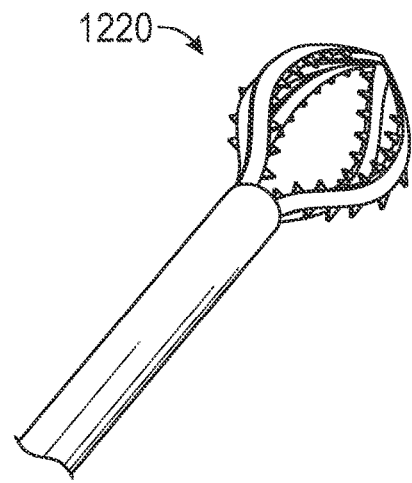
FIG. 51 shows another embodiment of a contact member that can be used with any treatment system embodiments disclosed herein.
Figure 52:
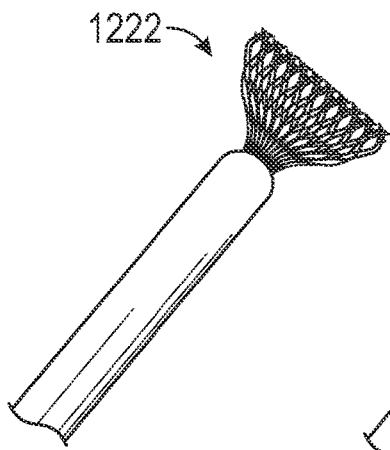
FIG. 52 shows another embodiment of a contact member that can be used with any treatment system embodiments disclosed herein.
Figure 53:
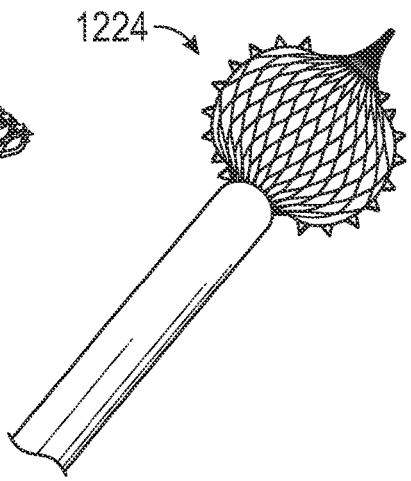
FIG. 53 shows another embodiment of a contact member that can be used with any treatment system embodiments disclosed herein.

FIGS. 51, 52, and 53 show additional embodiments of implant devices 1220, 1222, and 1224 (note that implant devices are also referred to herein as implants) that can be used with any of the embodiments of the treatment systems, delivery devices or procedures disclosed herein to treat an cavity. The implant device 1220 shown in FIG. 51 can have ribbons or struts made from Nitinol or any other suitable material which are configured to expand to an approximately spherical or elongated spherical shape, and which can be covered with small barbs or cleats (or other tissue anchors). The tissue anchors can be pointing in one or both circumferential directions. The implant device shown in FIG. 52 can have a stent-like body made from Nitinol or any other suitable material which can self-expand or be balloon expandable to an approximately spherical or elongated spherical shape. The body of the implant can be covered uniformly or otherwise with small barbs or cleats (or other tissue anchors). The implant device 1224 shown in FIG. 53 can have a woven wire body, which can be made from Nitinol or any other suitable material, and which can be configured to expand to an approximately spherical or elongated spherical shape. The body of the implant device 1224 can be covered uniformly or otherwise with small barbs or cleats (or other tissue anchors).

Figure 54:
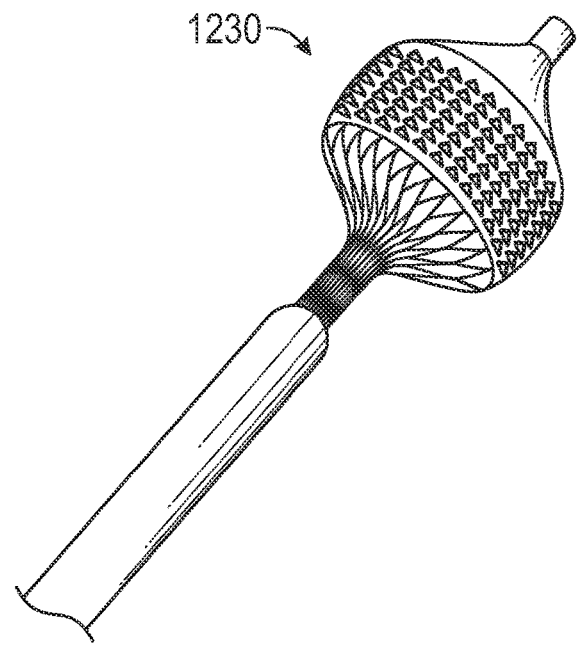
FIG. 54 shows another embodiment of a contact member that can be used with any treatment system embodiments disclosed herein.

FIG. 54 shows another embodiment of an implant device 1230 which can expand (or be expanded) to an approximately spherical or elongated spherical shape. For example and without limitation, the implant device 1230 can be configured to cover an inflatable balloon that can be inflated to expand the implant device 1230 into contact with the tissue of the cavity when the implant device 1230 is in a desired position within the cavity. The implant body 1230 covered with small barbs or cleats or other tissue anchors.

Figure 55:
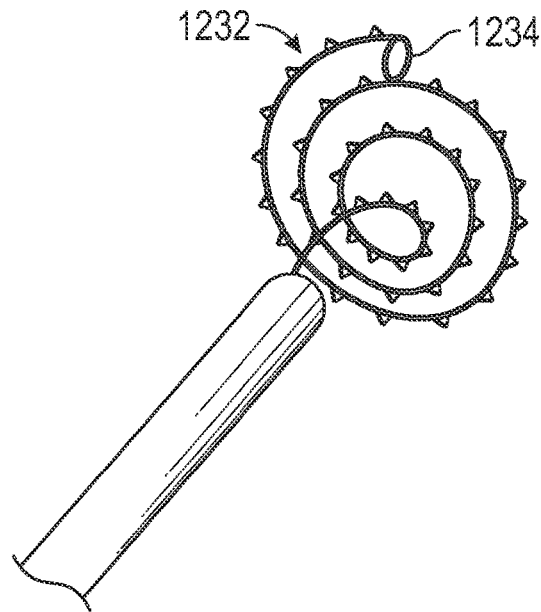
FIG. 55 shows another embodiment of a contact member that can be used with any treatment system embodiments disclosed herein.

FIG. 55 shows another embodiment of an implant device 1232 that can be used with any of the treatment system embodiments disclosed herein. In some embodiments, the implant device 1232 can have spiral shaped body at least when in a second, expanded state that can be used to exert the torque and twisting effect on the cavity. The implant device 1232 can be made from Nitinol, and can be covered with or have a plurality of small barbs, cleats, or other tissue anchors. The implant device 1232 can be self-expanding and can have a half-dome shape when in the second state. In some embodiments, the implant device 1232 can have a rounded end 1234 that can be approximately the same size as an internal lumen of the delivery system, or can be smaller, or larger and expandable.

FIGS. 56A-56B show an embodiment of treatment system 1240 having an implant device 1242, with the implant device 1242 being mostly contained with a catheter body 1244 of the treatment system 1240 in FIG. 56A, and at least a contact member 1246 of the implant device 1242 being in a second, expanded state in FIG. 56B. The contact member 1246 can have a plurality of barbs or anchor members about an outside surface thereof, and can be configured to expand to an approximately spherical or elongated spherical shape. The contact member 1246 can be self-expanding, or mechanically expandable, and can have a half-dome shape with a rounded distal end portion 1248. In some embodiments, the rounded end portion 1248 can be approximately the same size as an internal lumen of the delivery system, or can be smaller, or larger and expandable.

FIGS. 57-61 show additional different embodiments of anchoring elements or securing elements that can be used with any of the other components of the implant device embodiments disclosed herein. FIG. 57A shows an embodiment of a double arm securing element. FIG. 57B shows the double arm securing element of FIG. 57A being advanced into the tissue of the cavity and/or the tissue outside of or adjacent to the cavity adjacent to the opening of the cavity that has constricted around a body portion of the implant device.

Figure 58A:
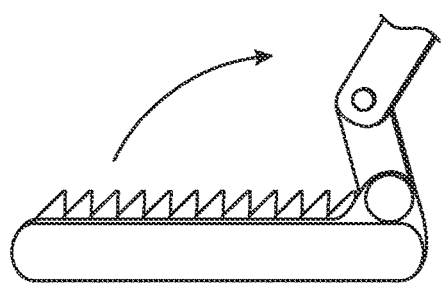
FIGS. 58A-58B show another embodiment of a securing element that can be used with any treatment system embodiments disclosed herein.
Figure 58B:
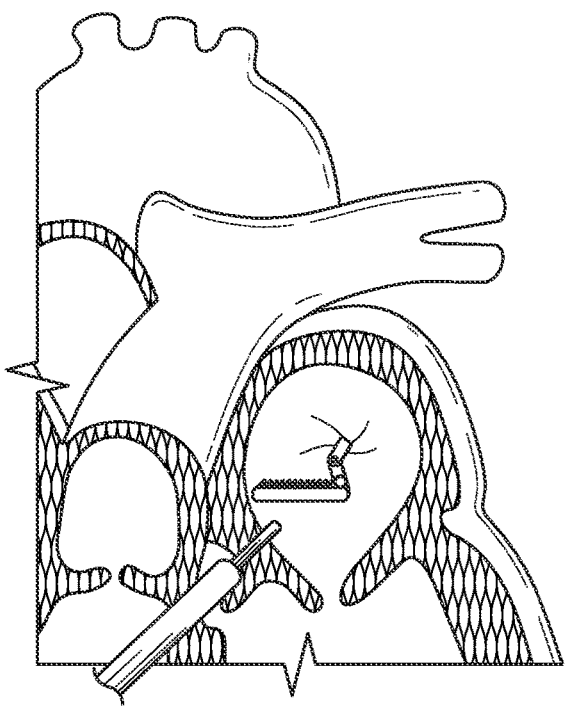
Figure 59A:
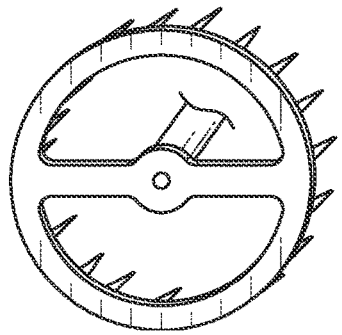
FIGS. 59A-59B show another embodiment of a securing element that can be used with any treatment system embodiments disclosed herein.
Figure 59B:
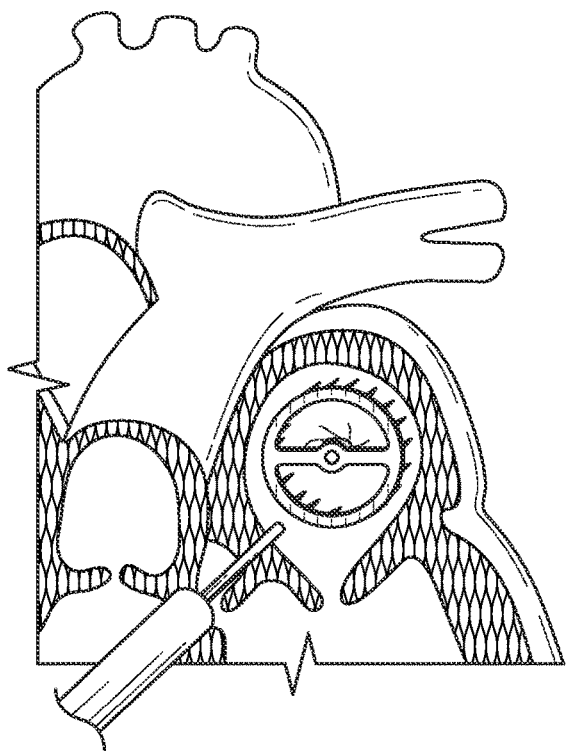

FIG. 58A shows an embodiment of a single folding clip anchor or securing element. FIG. 58B shows the single arm securing element of FIG. 58A being rotated against or clipped against the tissue of the cavity and/or the tissue outside of or adjacent to the cavity adjacent to the opening of the cavity that has constricted around a body portion of the implant device. In any embodiments, the securing element can be biased to remain in the secured or locked position. FIG. 59A shown an embodiment of a round disk anchor or securing element. FIG. 59B shows the round disk securing element of FIG. 59A being advanced toward the tissue of the cavity and/or the tissue outside of or adjacent to the cavity adjacent to the opening of the cavity that has constricted around a body portion of the implant device so that one or more tissue anchors of the securing element of FIG. 59A can engage with and/or penetrate into the tissue of the cavity and/or the tissue outside of or adjacent to the cavity adjacent to the opening of the cavity.

Figure 60A:
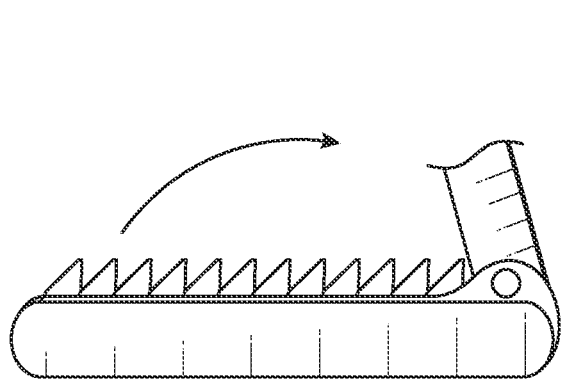
FIGS. 60A-60B show another embodiment of a securing element that can be used with any treatment system embodiments disclosed herein.
Figure 60B:
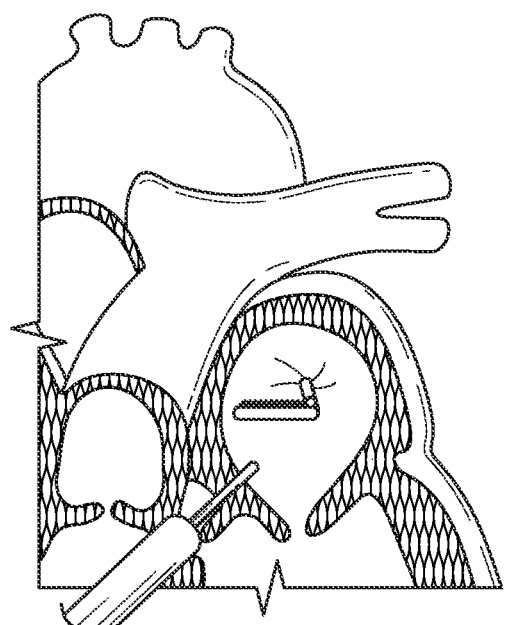
Figure 61A:
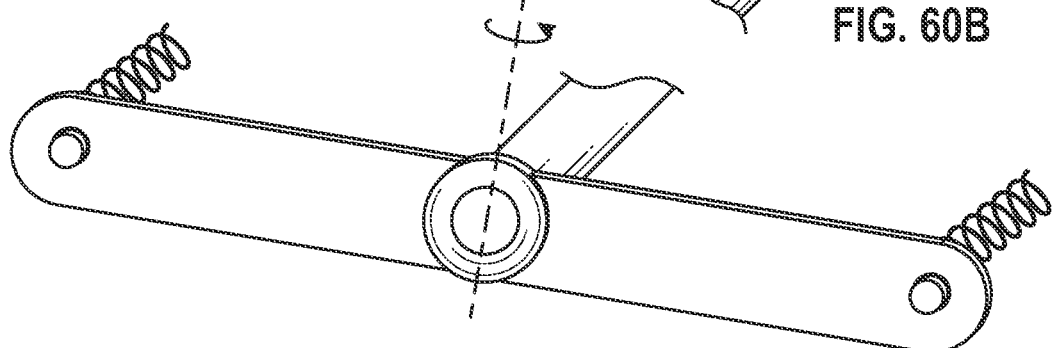
FIGS. 61A-61B show another embodiment of a securing element that can be used with any treatment system embodiments disclosed herein.
Figure 61B:
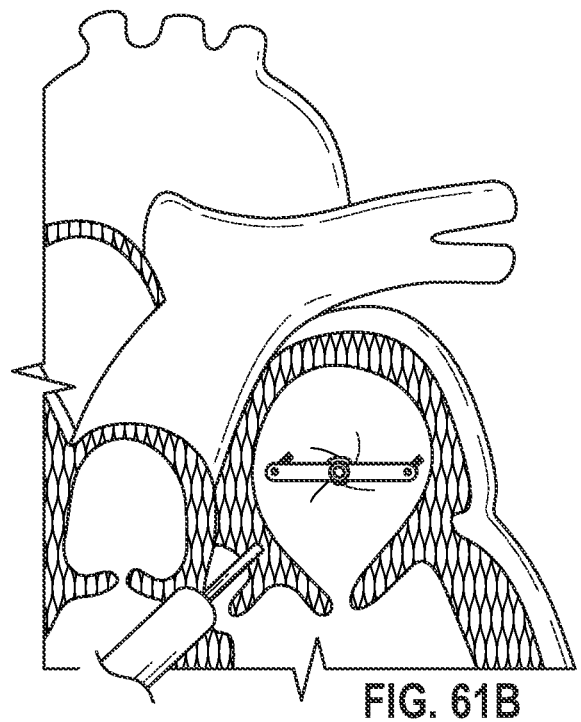

FIG. 60A shows an embodiment of a single folding clip anchor or securing element with a helical or screw type tissue anchor that can be used to engage with and/or penetrate into the tissue of the cavity and/or the tissue outside of or adjacent to the cavity adjacent to the opening of the cavity that has constricted around a body portion of the implant device. FIG. 60B shows the single folding clip anchor or securing element of FIG. 60A being rotated against or clipped against the tissue of the cavity and/or the tissue outside of or adjacent to the cavity adjacent to the opening of the cavity that has constricted around a body portion of the implant device. In any embodiments, the securing element can be biased to remain in the secured or locked position. FIG. 61A shows a double arm securing element with two helical or screw type tissue anchors. FIG. 61B shows the double arm securing element of FIG. 61A being rotated against the tissue of the cavity and/or the tissue outside of or adjacent to the cavity adjacent to the opening of the cavity that has constricted around a body portion of the implant device so that the tissue anchors on the arms can engage with and/or penetrate into the tissue. Both arms of the securing element of FIG. 61A-61B can collapse toward a body portion or axial centerline of the securing element, and can be configured to automatically deploy when extended past a distal end of the delivery catheter.

Figure 62A:
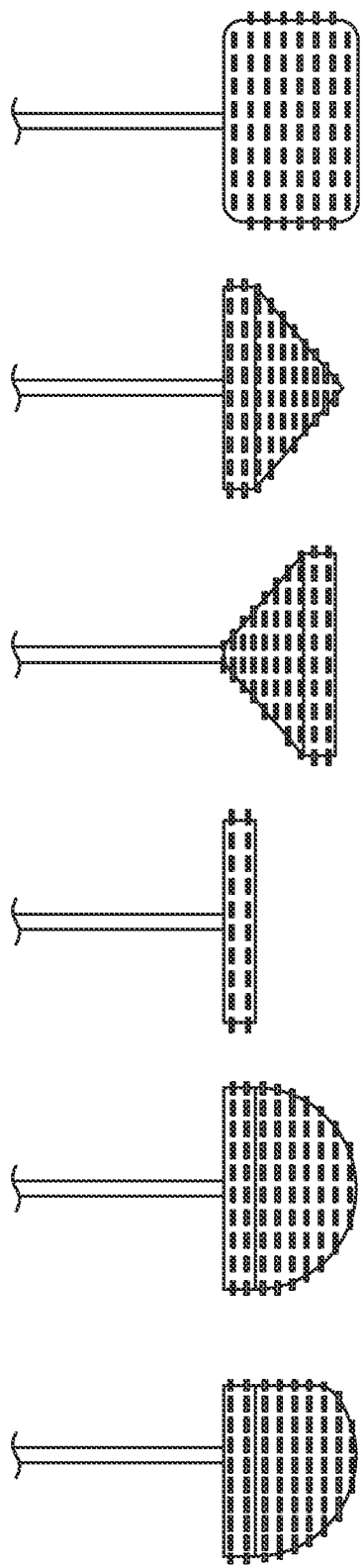
FIGS. 62A-62B show additional embodiments of contact members that can be used with any treatment system embodiments disclosed herein.
Figure 62B:
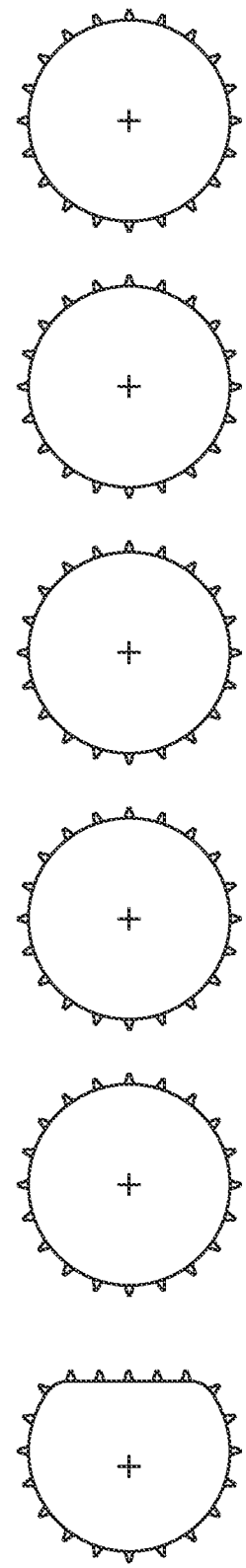
Figure 63:
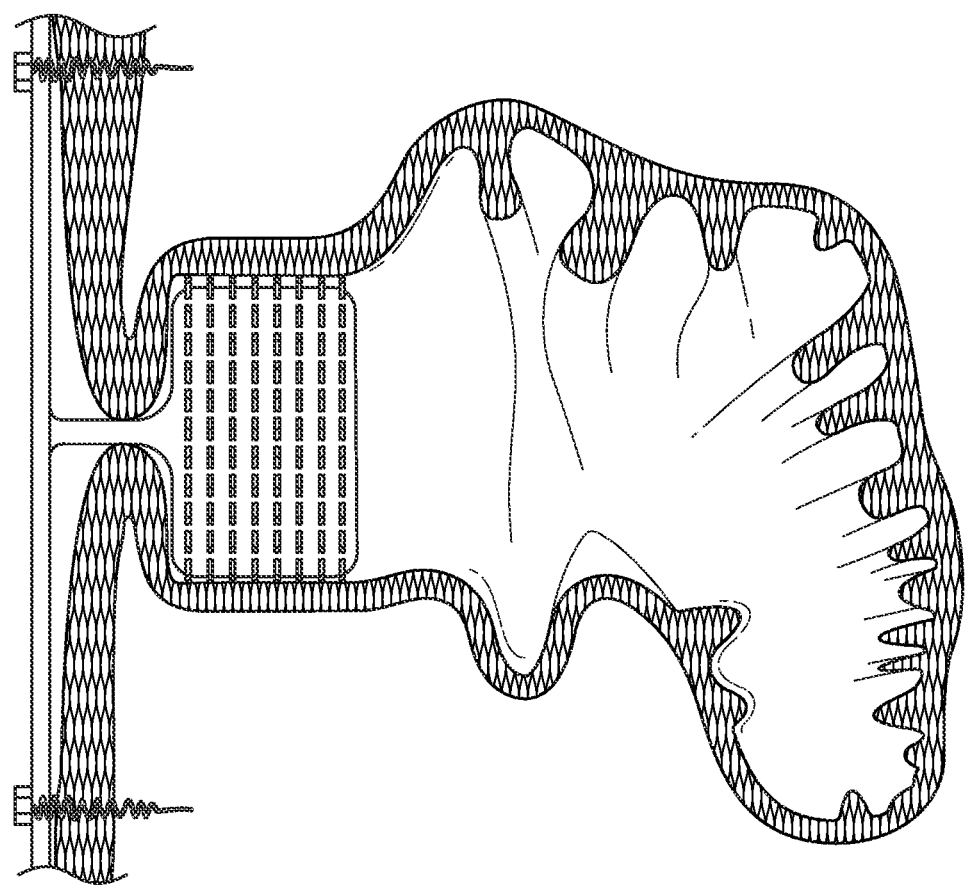
FIG. 63 shows a side view of an embodiment of a contact member.

FIGS. 62A-62B show side view and end views of different embodiments of contact member that can be deployed within the cavity to engage the tissue of the cavity so as to cause the cavity to twist when a torque is applied to the contact member. FIGS. 62A-62B show embodiments of contact members having cylindrical or thick disc shaped body portions, spherical shaped body portions, conical shaped body portions, and semi-spherical and/or half-spherical shaped body portions that are configured to better engage or couple with cavity tissue. Any of the embodiments of the contact members shown in FIGS. 62A-62B can have a plurality of barbs, micro-barbs, or other tissue anchors on an outside surface thereof. Additionally, any of the embodiments of the contact members shown in FIGS. 62A-62B can have outside surfaces that are uniformly covered with barbs, micro-barbs, or other tissue anchors. Further, any of the embodiments of the body portions disclosed herein, including without limitation the half-sphere shaped body portion shown in FIGS. 62A-62B, can have a flat area on one portion thereof to allow for a lower profile. FIG. 63 shows a side view of an embodiment of a contact member expanded against a tissue surface of the cavity, after a torque has been applied to the contact member that has caused a constriction of the tissue of the LA/cavity around a portion of the body of the implant device. FIG. 63 also shows the tissue anchors of the implant device advanced into the tissue of the LA/cavity to secure the cavity in the second position.

Additionally, any embodiment of the implant disclosed herein can have drug coatings, fabric or other at least substantially impermeable coverings (such as and similar to, without limitation, cover member 121 described above), electrical contacts to eliminate the conduction of electrical signals causing Afib, or other features to improve the performance of the implant. Some embodiments of the implant can be transseptally delivered via catheter and a disconnectable element between the implant element and the delivery system which would allow for permanent disconnection and therefore permanent implantation of the implant. Additionally, in any embodiments disclosed herein, the implant can be delivered without the use of a catheter, such as surgically, or otherwise.

Some embodiments include a device for closing or occluding an cavity, having an expandable implant that is configured to move between a first state in which the implant is substantially collapsed and a second state in which the implant is expanded, and a catheter configured to advance the implant into the cavity. The implant can be advanced into the cavity when the implant is in the first state and to cause the implant to move from the first state to the second state so that at least some of the plurality of tissue anchors engage an inner wall surface of the cavity after the implant has been advanced into the cavity. Any embodiments of the implant or insert can have a plurality of tissue anchors on an outside surface thereof.

Additionally, the catheter can be configured to rotate the implant in a first direction from a first rotational position to a second rotational position so that the implant can twist the wall of the cavity. As mentioned above, the catheter can rotate the implant from as little as a quarter turn to more than one turn. In any embodiments, the delivery device (which can be, in any embodiments disclosed herein, a catheter or can be any other suitable deployment or surgical device or system) can be configured such that a user can rotate the implant as many times as is necessary or desired to close, occlude, or collapse the cavity on itself or about an outside surface of the implant.

Any embodiments of the implant can be self-expandable such that the implant automatically expands when a restraint is removed from the implant, such as when the implant automatically expands when the implant is advanced past a distal end of an outer sleeve of the catheter. The implant can be biased to remain in an expanded state after deployment into the cavity.

Additionally, any embodiments of the implant or systems disclosed herein can be configured such that the implant can engage or automatically engage with a tissue or tissue surface when rotated or turned in one (or a first) direction. The implant of any embodiments disclosed herein can also be configured to disengage with any tissue that it is engaged with when turned in a second direction (the second direction being opposite to the first direction). In this embodiment, a user can engage the tissue or wall surface of the cavity by rotating the implant in a first direction, and disengage (if needed for any reason, including without limitation repositioning the implant) by rotating the implant in a second direction, the second direction being opposite to the first direction.

In any embodiments, as has been described, the implant can be configured to prevent the contact member from rotating back to the first rotational position after the contact member has been fully deployed. For example, as described above, any embodiments of the implant can have a securing element or anchoring element that can be configured to engage with tissue surrounding the cavity, such as the tissue of an internal wall of the space outside of the cavity. Some embodiments of the implant can have a securing element having a plurality of tissue anchors configured to engage with an internal wall of the space outside of or adjacent to the cavity.

For example and without limitation, the implant of any device, apparatus, and method embodiments disclosed herein can include a securing element configured to engage with an internal wall of the space outside of or adjacent to the cavity. The securing element can have one or a plurality of arms and/or tissue anchors configured to engage with an internal wall of the space outside of or adjacent to the cavity, or can be configured to be sutured to or otherwise coupled with an internal wall of the space outside of or adjacent to the cavity. In any embodiments, the implant can be configured to prevent or inhibit counter-rotation of the contact member or other portions of the implant back to the first rotational position after the contact member or other portion(s) of the implant has been fully deployed. In any embodiments, the implant can be configured to rotate or permit rotation of the contact member in a first direction from the first rotational position to the second rotational position, and to prevent or inhibit rotation of the implant in a second direction after the contact member or other portion of the implant has been fully deployed, the second direction being opposite to the first direction.

Any embodiments disclosed herein can include an implant for deployment within a cavity or vessel, having an expandable body (which can, but is not required to, have any of the features or characteristics of the contact member), a plurality of tissue anchors on an outside surface of the expandable body configured to engage with an inner wall surface of the cavity or vessel, and an anchor element coupled with the expandable body configured to engage with a tissue surface adjacent to the inner wall surface of the cavity or vessel.

Some embodiments of methods of closing or occluding a cavity using any embodiments of the implants disclosed herein will now be described. The method or procedure can include advancing a deployment device having an implant having an expandable member or contact member into the patient's space outside of or adjacent to the cavity, moving or expanding a portion of the implant from a first state to a second state within the cavity or within the space outside of the cavity, wherein the expandable member or contact member is substantially collapsed in the first state and expanded in the second state, engaging a wall portion on an inside of the cavity with the expandable member or contact member (which can, but is not required to have one or more tissue anchors on an outside surface thereof), rotating the expandable member or contact member from a first rotational position to a second rotational position to twist the wall portion on the inside of the cavity, and preventing the expandable member or contact member from rotating back to the first rotational position. Any portion of the implant, including but not limited to the expandable member or contact member, can be self-expanding, wherein moving the expandable member or contact member from the first state to the second state comprises advancing the expandable member or contact member out of a distal end of the deployment device.

Additionally, in any embodiments disclosed herein, engaging a wall portion on an inside of the cavity can include engaging a wall portion on an inside of the cavity with one or more tissue anchors positioned on an outside surface of the expandable member or contact member or other portion of the implant. Further, preventing the implant from rotating back to the first rotational position can include engaging a tissue wall outside of the cavity with an anchor element or securing element. In some embodiments, the anchor element or securing element can be rotationally fixed to the expandable member or contact member and/or other portion of the implant to prevent relative movement between the anchor element and the expandable member or contact member and/or other portion of the implant. Preventing the expandable member or contact member and/or other portion of the implant from rotating back to the first rotational position can include engaging a tissue wall of the space outside of or adjacent to the cavity with an anchor element or securing element, wherein the anchor element can be rotationally fixed relative to the implant and configured to prevent the expandable member or contact member and/or other portion of the implant from rotating back to the first rotational position, or engaging an internal wall of the outside of the cavity with an anchor element or securing element. In any embodiments, the anchor element or securing element can include a plurality of tissue anchors on at least one surface thereof, the tissue anchors configured to engage with the internal wall of the space outside of or adjacent to the cavity.

In any embodiments disclosed herein, the implant can be configured to automatically rotate from the first rotational position to the second rotational position after the contact member and/or other portion of the implant is in the second state, or can be activated to self-rotate at any desired time. For example and without limitation, the implant could have a spring or other torsional member configured to rotate the contact member and/or other portion of the implant or other portion of the body of the implant upon release or activation of the spring, or could be configured to be pre-wound or pre-twisted when the implant or contact member and/or other portion of the implant is in a first state. The self-rotation or self-twisting could be done, for example, after the contact member and/or other portion of the implant has been secured to a wall portion surrounding the cavity, and after a portion of the implant has engaged with at least a portion of an inside wall surface of the cavity so that the rotation or twisting of a portion of the implant causes a twisting of the cavity, thereby causing the opening of the cavity to close or substantially close.

Therefore, in any embodiments, the implant can be configured to automatically rotate or self-rotate from the first rotational position to the second rotational position upon a release of a restraint holding the implant in the first rotational position, or upon a triggering or actuation of the rotational mechanism, which can be a spring or other torsional member. In some embodiments, a shaft extending through the implant can be configured to be wound or rotated relative to a securing portion or base of the implant, or can have a spring around the shaft, so that a rotation of the shaft relative to the securing portion or base of the implant as a result of the release of the torsion in the shaft or the spring surrounding at least a portion of the shaft, can result in the twisting of the cavity.

In other embodiments, the implant can have a shaft or body portion that extends from a base, wherein the shaft can be rotated (either manually, by the catheter, or can be self-rotating) relative to the base from the first rotational position to the second rotational position, and wherein a ratchet mechanism or other securing mechanism can be used to secure the shaft or body portion in the second rotational position relative to the base. The base can be configured to engage with and be secured to a wall or tissue of the space outside of or adjacent to the cavity before the shaft or body portion engages an inner wall portion of the cavity and before the shaft or body portion is rotated to the second position.

Additionally, in any apparatus, implant device, method, or other embodiments disclosed herein, the second rotational position can be at least one-eighth or approximately one-eighth of a complete rotation (i.e., 45 degrees or approximately 45 degrees) relative to the first rotational position, one-quarter or approximately one-quarter of a complete rotation (i.e., 90 degrees or approximately 90 degrees) relative to the first rotational position, or at least one-half or approximately one-half of a complete rotation (i.e., 180 degrees or approximately 180 degrees) relative to the first rotational position, or wherein the second rotational position can be from one-eighth or approximately one-eighth of a complete rotation (i.e., 45 degrees or approximately 45 degrees) to one-half or approximately one-half of a complete rotation (i.e., 180 degrees or approximately 180 degrees) relative to the first rotational position. In any apparatus, implant device, method, or other embodiments disclosed herein, the second rotational position can be from one-quarter or approximately one-quarter of a complete rotation (i.e., 90 degrees or approximately 90 degrees) to one or more or approximately one or more complete rotations (i.e., 360 degrees or approximately 360 degrees or more) relative to the first rotational position, or from one-quarter or approximately one-quarter of a complete rotation (i.e., 90 degrees or approximately 90 degrees) to two, three, or more complete rotations or approximately one or more complete rotations (i.e., 360 degrees or approximately 360 degrees or more) relative to the first rotational position, one-eight or approximately one-eighth of a complete rotation (i.e., 45 degrees or approximately 45 degrees) to one, two, three, or more complete rotations or approximately one or more complete rotations (i.e., 360 degrees or approximately 360 degrees or more) relative to the first rotational position, or any value or ranges of values within any of the foregoing ranges. In any embodiments disclosed herein, the twisting movement or step can be accomplished by a torque catheter.

Further, in any apparatus, implant device, or method embodiments disclosed herein, the catheter can be configured to exert a torque on the implant to rotate the implant from the first rotational position until a threshold predetermined torque level is reached, or until the user decides to stop the rotation, whichever comes first. In some embodiments, the threshold predetermined torque level can be from 0.25 in-oz of torque or approximately 0.25 in-oz of torque to 10 in-oz of torque or approximately 10 in-oz of torque, or from 0.5 in-oz of torque or approximately 0.5 in-oz of torque to 5 in-oz of torque or approximately 5 in-oz of torque.

In any embodiments disclosed herein, without limitation, the contact member can have an outer diameter or size when in the first or collapsed state of from approximately 3 mm to approximately 8 mm (approximately 9 Fr to approximately 24 Fr), or from approximately 4 mm to approximately 6 mm, or of any values or ranges of values between any of the foregoing ranges, and/or a length (of the arm or strut members) from approximately 20 mm to approximately 60 mm, or from approximately 30 mm to approximately 50 mm, or of any values or ranges of values between any of the foregoing ranges. Further, in any embodiments disclosed herein, without limitation, the contact member can have an outer diameter or size when in the second or expanded state of from approximately 6 mm to approximately 14 mm (approximately 18 Fr to approximately 42 Fr), or of any values or ranges of values between any of the foregoing ranges, or from approximately 9 mm to approximately 11 mm, or of any values or ranges of values between any of the foregoing ranges, and/or a length (of the arm or strut members) from approximately 10 mm to approximately 40 mm, or from approximately 20 mm to approximately 30 mm, or of any values or ranges of values between any of the foregoing ranges.

In any embodiments disclosed herein, without limitation, the securing element can have an outer diameter or size when in the first or collapsed state of from approximately 3 mm to approximately 8 mm (approximately 9 Fr to approximately 24 Fr), or of any values or ranges of values between any of the foregoing ranges, or from approximately 4 mm to approximately 6 mm, and/or a length from approximately 4 mm to approximately 12 mm, or from approximately 6 mm to approximately 8 mm, or of any values or ranges of values between any of the foregoing ranges. Further, in any embodiments disclosed herein, without limitation, the securing element can have an outer diameter or size when in the second or expanded state of from approximately 6 mm to approximately 18 mm (approximately 18 Fr to approximately 54 Fr), or from approximately 9 mm to approximately 15 mm, or of any values or ranges of values between any of the foregoing ranges, and/or a length (of the arm or strut members) from approximately 4 mm to approximately 8 mm, or from approximately 4 mm to approximately 6 mm, or of any values or ranges of values between any of the foregoing ranges. Further, any embodiments of the securing elements disclosed herein can have tissue engaging tips or portions (i.e., the portion configured to penetrate or engage with the tissue) having a length of from approximately 0.2 mm to approximately 2 mm, or from approximately 0.5 mm to approximately 1 mm, or of any values or ranges of values between any of the foregoing ranges.

Another embodiment of an implant device 1920 is configured to fold or kink the cavity at the opening, and then clip and hold that position, effectively closing the cavity. FIGS. 64A-64D shows one variation of a sequence of steps to accomplish that. In some embodiments, the steps of deployment and implantation can include: inserting catheter into a middle of the cavity opening, flexing a portion of the implant 1920 in a first direction (which can be up, as shown in the figures); clipping and holding the position of the bent portion of the implant 1920 to the atrial wall (additional anchoring can be used to anchor implant to lower atrial wall); and/or releasing the delivery catheter from the implant 1920.

Further, any embodiments of the devices and methods disclosed herein can be adapted or modified for use with robotic surgical devices or apparatuses. For example without limitation, any of the deployment catheters disclosed herein can be modified for use with such robotic surgical devices and apparatuses. All such applications of devices and methods disclosed herein for use with robotic systems are contemplated as forming part of the disclosure herein.

Also described herein are novel devices, systems, and methods for reshaping, closing, or occluding a cavity, occluding or closing holes, slits, valves and other openings in the body such as tissue or vessels, valves, passageways, organs, and other tissue bodies, and/or treating other conditions in which closure or occlusion is desired. In any embodiments disclosed herein, the cavity, opening, vessel, valve, and/or tissue can be of a surface wound, an internal wound, a chamber, valve or cavity in the heart, lungs, stomach, or other organ, a gastrointestinal chamber or cavity, a blood vessel or other vessel, or other chamber or enclosure within the body (which can be the body of any living creature), including chambers and pockets in the body that are created by the methods and devices disclosed herein such as for volume reduction of the chamber or tissue gathering as will be further described below. All such conditions for which any embodiments of the devices and methods disclosed herein can be configured to treat are collectively referred to herein as a cavity, such that any use of the term cavity is meant to include any of the conditions or abnormalities described above, unless specifically noted otherwise.

Some embodiments comprise a method that includes advancing a treatment system to the cavity (whether internal or external), advancing and deploying an contact member (which can be, in some embodiments, covered with barbs, texture, or other tissue engaging features or, alternatively, can be smooth) and which can have a generally spherical or orb shaped shape into the cavity, allowing the contact member to engage distally and/or radially with inner wall surfaces of the cavity, applying a rotation to an inner catheter member connected to the contact member to twist the cavity to close and/or occlude the cavity. The cavity can be closed near the entry of the opening of the cavity. For surface wounds, the cavity can be closed near the surface of the wound so as to draw the tissue surrounding the wound together to close the wound.

By reshaping, closing and/or occluding the cavity, some embodiments disclosed herein can effectively seal the wound to reduce the risk of exposure or infection of the wound, and stop blood loss through the wound. Any methods of deployment disclosed herein can also include deployment of a securing element (which is also referred to herein as a locking element or anchoring element) that is configured to inhibit or prevent the unwinding of the contact member, thereby inhibiting or preventing the untwisting of the tissue that has been drawn together by the treatment device. When used to treat an internal cavity and/or when applied to an external surface of the body, the securing element of any embodiments disclosed herein can have a low profile so as to limit the amount of the implant that projects away from the tissue surface, thereby reducing the impact of the implant on the function of the organ in which the implant is disposed. For example, in the stomach, the securing element can be configured to be flush or approximately flush with the inside tissue surface, in some embodiments, or protrude by only a small amount (e.g., in some embodiments, approximately 5% or less of the overall length of the implant in the implanted state, or approximately 10% or less of the overall length of the implant in the implanted state, or approximately 15% or less of the overall length of the implant in the implanted state) away from the tissue surface. In some embodiments configured to treat surface wounds, the securing element can be configured to be flush or approximately flush with the epidermis, or protrude by only a small amount (e.g., in some embodiments, approximately 5% or less of the overall length of the implant in the implanted state, or approximately 10% or less of the overall length of the implant in the implanted state, or approximately 15% or less of the overall length of the implant in the implanted state) away from the tissue surface. In some embodiments, the entire implant can be surrounded by tissue of the cavity tissue so that no portion, or only a minimal portion (for example, less than 10% of the surface area, or less than 40% of the surface area) of the implant is exposed to blood flow within the cavity. Any of the devices used in any of the methods described here may be advanced under any of a variety of visualization techniques, e.g., fluoroscopic visualization, ultrasound, etc.

The implant of any embodiments disclosed herein can have an expandable atraumatic shaped contact member with tissue gripping features located on the outer edges of the shape, coupled to a securing element feature which can hold the final closed position of the implant. The implant of any embodiments disclosed herein can be configured to grip the internal tissue of the cavity with radial force as well. The contact member of any embodiments disclosed herein can have an atraumatic shape that can be spherical, dome shaped, or comprise a coil of wire in the shape of a disk, can have expanded cut pattern in the shape of a stent, or anything else which can have rounded edges. In some embodiments, a surface of the contact member, such as an outside surface of the contact member, can have the barbs (which can be tissue anchors), metal hooks, plastic cleats, rough texture or surface features, a coating or activated adhesive configured to grip the inside surface of the cavity, teeth, cleats, barbs, nubs, texture, studs, anchors or other tissue engaging features or other similar features configured to penetrate or engage the tissue of the cavity (all collectively referred to herein as tissue anchors, which use of this term is meant to describe and include any of the foregoing features individually and/or any combination of these features). Additionally, in any embodiments disclosed herein, the tissue anchors can be positioned on or adjacent to an end portion of the implant to engage with an end portion of the cavity. In any embodiments, the barbs can be directional allowing for tissue engagement in one rotational direction and a disengagement in the opposite rotational direction for a possible repositioning, resizing, or removal from the cavity.

The rotation used to twist closed or occluded (completely or substantially) the cavity for any embodiments disclosed herein may be as little as a quarter of a turn (i.e., revolution), a half turn, a complete turn, up to as much as multiple turns for deeper or longer cavities or applications that require additional turns, such as volume reduction of the stomach chamber. The securing feature or element (also referred to herein as an anchoring element) in any embodiments disclosed herein can have a single arm or multiple arms which can be coupled with the implant body that is positioned and rotated within the closed or substantially closed cavity. The securing feature or element can be configured to engage tissue adjacent to the cavity. In any embodiments, the securing element can have multiple arms or members, or any other suitable shaped anchors configured to engage the tissue and prevent the tissue from untwisting or unraveling. In some embodiments, the securing element can have an annular ring, can have a disk or other cover member, for example, a disk that is proximal to the arms and is configured to provide a cover or seal over the implant. In some embodiments, the securing element can also have a small diameter ring which can be configured to clamp to or engage with the tissue which contacts to the center hub of the implant (adjacent to the opening of the cavity) or it can also have a clip which folds and clips the implant to the side of the wall of the space outside of or adjacent to the cavity.

Figure 65A:
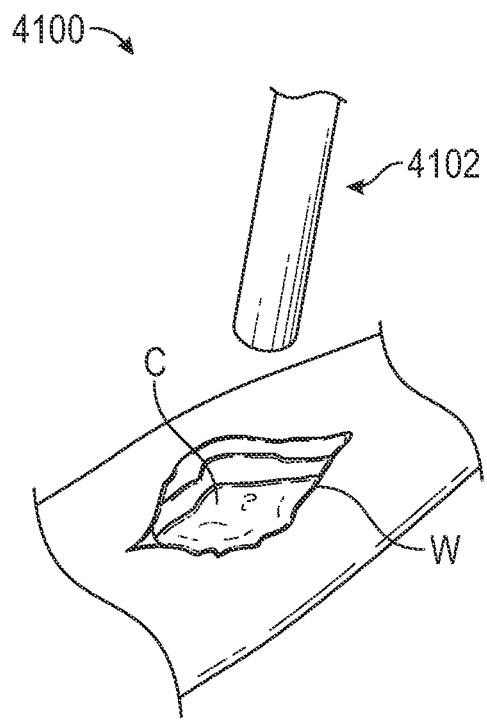
FIGS. 65A-65H show an embodiment of a device and an embodiment of a method for closing or occluding a wound.
Figure 65B:
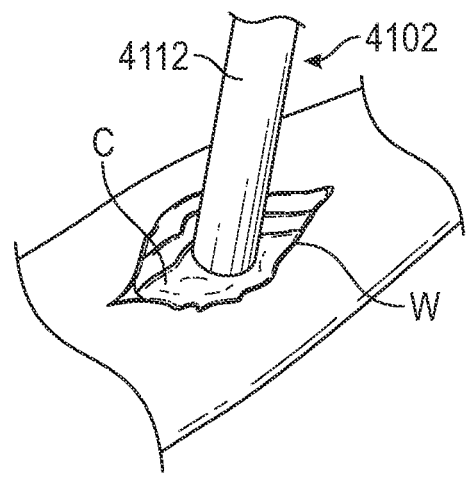
Figure 65C:
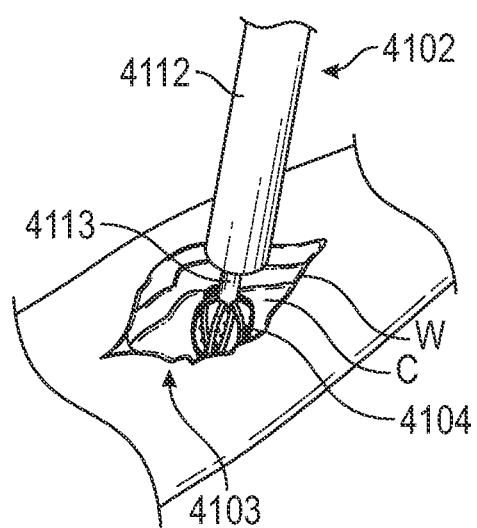

FIG. 65A shows a wound on a surface of a body and an embodiment of the treatment system 4100 having a delivery catheter or other delivery device 4102 being advanced toward the wound W having a cavity C. An implant device 4103 is supported within or by the delivery device 4102. As used herein, a wound can be a chronic wound, a surface wound of any kind including gunshot wounds, trauma wounds, combat wounds, or otherwise, an internal wound inside the body, or other condition in which there is a separation of tissue that is intended to be joined. The delivery device 4102 can be advanced into the cavity C of the wound W, as shown in FIG. 65B. Thereafter, a sheath or sleeve 4112 of the delivery device 4102 (which can be intermediate sleeve or an outer sleeve) can be retracted to expose a contact member 4104 that can be expanded in the cavity C of the wound. In some embodiments, the contact member can have a series of self-expanding struts or arms made out of a shape memory material such as Nitinol, or can be any other expandable device such as an expansion balloon used for expanding stents or other expandable implant or otherwise.

The user of the treatment system 4100 can further advance the contact member into the cavity and position the contact member 4104 at any desired depth. In any embodiments disclosed herein, the contact member 4104 can be self-expanding such that it expands against one or more walls of tissue within the cavity as it is advanced out of the sleeve 4112 of the delivery device. In other embodiments, the contact member 4104 can be an expandable device that is mechanically expanded using a balloon or other mechanical mechanism to expand arms or an outer surface of the contact member against the tissue surface.

Figure 65D:
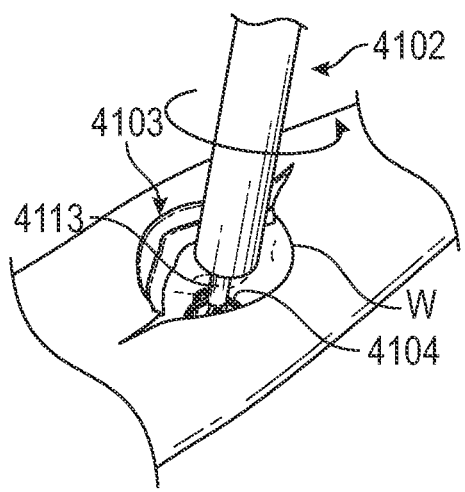
Figure 65E:
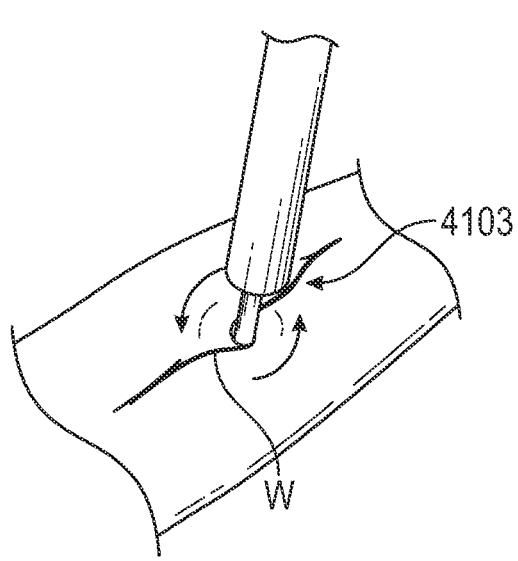

Once the contact member 4104 is in the desired position within the cavity C such that the contact member 4104 is in contact with one or more surfaces of the cavity, a core member 4113 of the delivery device 4102 that is rotationally coupled with the contact member 4104 can be rotated to rotate the contact member 4104 as indicated by the arrow in FIG. 65D to twist the tissue associated with the cavity. The contact member can be rotated in either direction. As shown in FIG. 65E, the twisting of the tissue within the cavity can cause the tissue to collapse about the implant device 4103 such as a body portion of the implant device 4103 that can be used to couple the contact member 4104 with a securing element, or a portion of the delivery device, such as the core member 4113 or otherwise. In any of the embodiments disclosed herein, the collapse of the tissue of the cavity or wound can result in a complete closure of the cavity or wound, a significantly complete closure of the cavity, a significant occlusion of the cavity, and/or a significant reduction in the surface area of the surface of the wound, for example, for surface wounds (the foregoing states are collectively referred to as the second state).

Figure 65F:
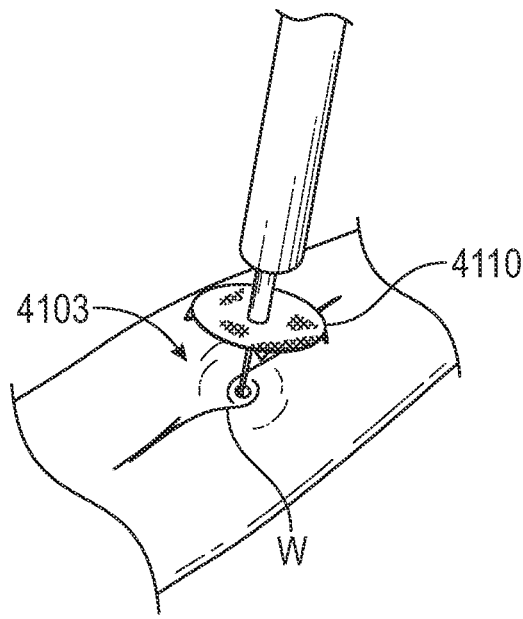
Figure 65G:
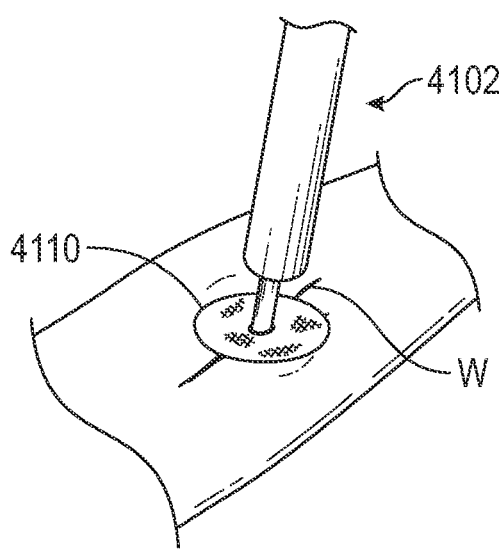
Figure 65H:
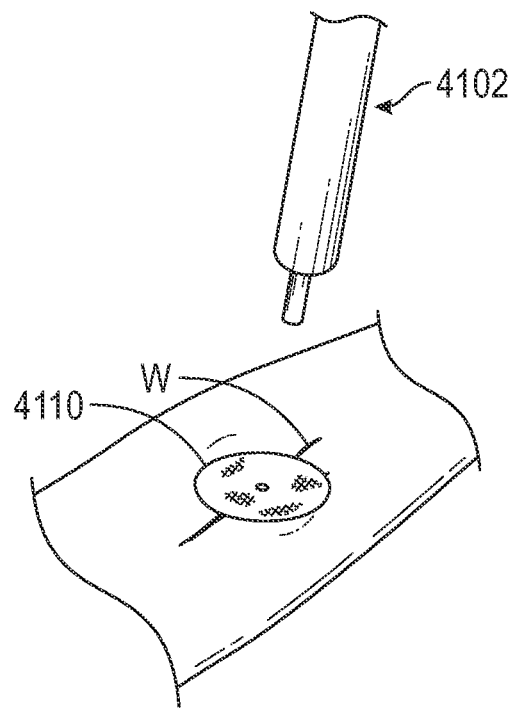

Thereafter, sutures, staples, or other tissue fasteners can be used to hold the edges of the cavity together or in the position that resulted from the twisting or rotation of the contact member. Or, in some embodiments, with reference to FIGS. 65F-65G, a securing element 4110 can be deployed from the delivery device 4102 that can engage with and couple with the tissue surrounding the cavity or insecure or the tissue surrounding the cavity or wound in the position that resulted from the twisting or rotation of the contact member. The securing element 4110 can have any form of tissue anchor or anchors thereon extending away from a tissue facing surface of the securing element 4110 comprising any of the features of any of the other tissue anchors disclosed herein with respect to any other embodiments disclosed herein. Additionally, in some embodiments, the securing element 4110 can comprise a mesh cover having tissue anchors that can engage with the tissue surrounding the cavity. After the securing element 4110 has engaged with the tissue surrounding the cavity or wound, the securing element 4110 can be disengaged from the delivery device 4102 and the procedure can be complete, as shown in FIG. 65H. As desired, the user can apply any form of treatment substance under the securing element 4110, such as antimicrobial or antibiotic substance.

In any embodiments disclosed herein, a retaining member such as or similar to any of the other retaining members disclosed with respect to any of the other implant embodiments disclosed herein can be used to couple the securing element 4110 to the contact member 4104. Additionally, in some embodiments, the retaining member can be used to bias the securing element 4110 toward the tissue surface and/or the contact member 4104, or be used to control the positioning or spacing between the securing element 4110 and the contact member 4104.

In any embodiments disclosed herein, the implant device 4103 can be configured such that the contact member can be removed from the cavity or wound after the cavity has been secured in the closed, substantially closed, reduced, or occluded state (e.g., in the second state) by the securing element or elements or other devices or connectors, such as staples, sutures, or other tissue anchors, as desired. For example and without limitation, the contact member can be collapsed or deflated and removed from the cavity after the cavity has been secured in the second state. For example without limitation, the implant device 4103 can have a hollow tube or opening in a body portion thereof that the contact member can be withdrawn through. Thereafter, the securing elements can be used to cover not only the collapsed cavity but also the opening. Alternatively, a plug or other device can be positioned within the opening of the hollow to or body portion that the contact member has been withdrawn through as part of the process of removing the contact member such as, for example, a plug that automatically is pulled into the opening of the hollow tube or body portion as the contact member is withdrawn or a separate plug is inserted after the contact member has been withdrawn. In other embodiments, the contact member can remain within the cavity in the expanded state. In some embodiments, the contact member can be collapsed or deflated (for example, if the contact member is an expandable balloon) and allowed to remain within the cavity. In any embodiments disclosed herein, the contact member can be biodegradable or bioabsorbable such that the contact member can disintegrate within the body over time, which may be particularly useful in the case of treating wounds. In other embodiments, the system can be configured such that the contact member is removable after the securing element has been positioned to secure the wound closed. In any embodiments disclosed herein, the contact member can have surface coatings that can be drug eluding, have antimicrobial or antibacterial properties, or other therapeutic advantages or benefits to the cavity or wound.

Any embodiments of the treatment system 4100, the delivery device 4102, the implant device 4103, the contact member 4104, the securing element 4110, and/or any other components disclosed herein can have any of the components, features, or other details of any other treatment system, delivery device, implant device, securing element, or any other component embodiments disclosed herein, including without limitation, any of the components of any of the embodiments of the treatment system 100, 200, 300, 400, implant device 102, 202, 302, 402, and/or securing element 110, 210, 310, 410 described above, in any combination with any of the components, features, or details of the treatment system 4100, the delivery device 4102, the implant device 4103, the securing element 4110, and/or any other components of the treatment system 4100 disclosed herein. For example and without limitation, in any embodiments, the contact member can have any of a number of arms or struts, tissue anchors or other tissue engaging features, or can be just an expandable balloon having a smooth surface or with a textured surface or other gripping features thereon.

FIGS. 66A-66H illustrate another embodiment of a treatment system 4200 that can be used for repairing mitral valves or tricuspid valves and another embodiment of a use of the embodiments of the treatment systems disclosed herein for repairing mitral valves. Any embodiments of the treatment system 4200 or implant device 4203 can have any of the components, features, or other details of any other treatment system or implant device embodiments disclosed herein, including without limitation any of the embodiments of the treatment system 100, 200, 300, 400 or implant device 102, 202, 302, 402 described above, in any combination with any of the components, features, or details of the treatment system 4200 or implant device 4203 disclosed below. Similarly, any components, features, or other details of any of the other treatment system or implant device embodiments disclosed herein can have any of the components, features, or other details of any embodiments of the treatment system 4200 or implant device 4203 disclosed herein, in any combination, with any of the components, features, or details of the other treatment system or implant device embodiments disclosed herein.

Some embodiments of the devices disclosed herein for treating the mitral valve can include a first implant that has at least a contact member and a securing element, wherein the contact member can be configured to move between a first state and a second state. The contact member can be configured to engage at least a portion of a tissue of a commissure of the mitral valve after the contact member has been advanced into the mitral valve, and can be configured to rotate at least in a first direction from a first position to a second position to twist at least a portion of the tissue of the commissure of the mitral valve to draw the tissue in the commissure together to reduce a size of the mitral valve annulus. The contact member can be rotated by, for example and without limitation, rotating a core member or other member of the delivery device coupled with the contact member. A suture, staple, and/or a securing element can be implanted adjacent to or in contact with the contact member to prevent a rotation of the tissue that has been drawn together by the contact member in a second direction that is opposite to the first direction. The contact member and/or the securing element can have any of the features, components, and/or details of any of the other embodiments of the contact member and the securing element disclosed here. In some embodiments, the device can have a second contact member of a second implant configured to engage at least a portion of a tissue of a second commissure of the mitral valve after the contact member has been advanced into the mitral valve, and can be configured to rotate at least in a first direction from a first position to a second position to twist at least a portion of the tissue of the second commissure of the mitral valve to draw the tissue in the second commissure together to reduce a size of the mitral valve annulus. In some embodiments, a connecting bar or connecting member can be used to couple the second implant to the first implant to maintain a desired spacing between the first and second implants. A length of the connecting member can be adjustable to draw together or push apart the first and second implants and, consequently, the first and second commissures.

Figure 66A:
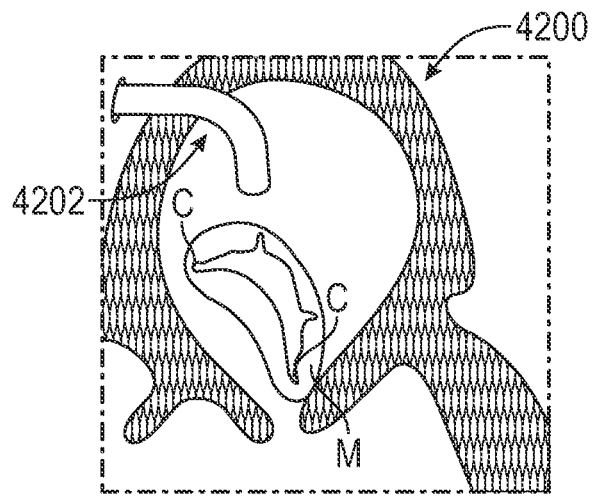
FIGS. 66A-66H show an embodiment of a device and an embodiment of a method for repairing a mitral valve.
Figure 66B:
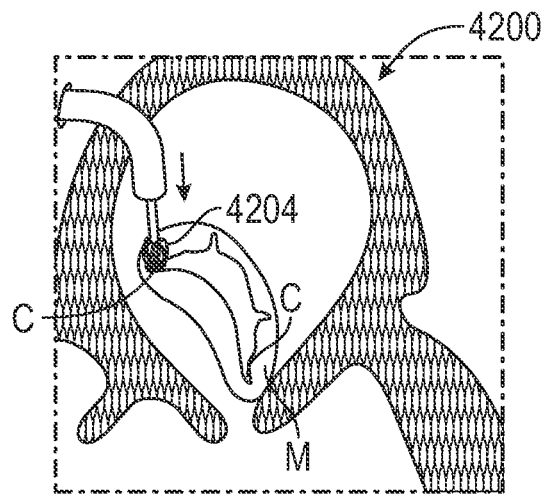

With reference to FIG. 66A-66B, the delivery device 4202 can be advanced through the patient's heart toward the mitral valve M to perform a repair of the tissue in the commissures C of the mitral valve. The term commissure describes the area where the anterior and posterior leaflets of the mitral valve come together at their insertion into the annulus. FIG. 66B shows the contact member 4204 being advanced into a first commissure of the mitral valve. The contact member 4204 can be advanced into the space adjacent to the commissure and then expanded to the second state of the contact member 4204 so that the contact member 4204 expands against one or more tissue surfaces in the commissure. In other embodiments, the contact member 4204 can be expanded to the second state of the contact member 4204 and then advanced into the space adjacent to the commissure and into contact with one or more tissue surfaces in the commissure.

A similar device could be used in the tricuspid valve with similar rotational implants at the commissures to gather tissue and reduce the annular distance by gathering the tissue at each commissure. The septal and posterior leaflets are generally smaller than the anterior leaflet and therefore should be rotated accordingly. The septal implant could be rotated clockwise and the posterior leaflet rotated counterclockwise to pull the posterior leaflet back into coaptation. A connection member could also connect the implants whereas the member could be adjustable, thus drawing one closer to the other for additional annular reduction. Some embodiments can be configured to push apart the implants, thereby elongating the valve opening. A third implant between the septal and posterior could add further plication or reduction.

Figure 66C:
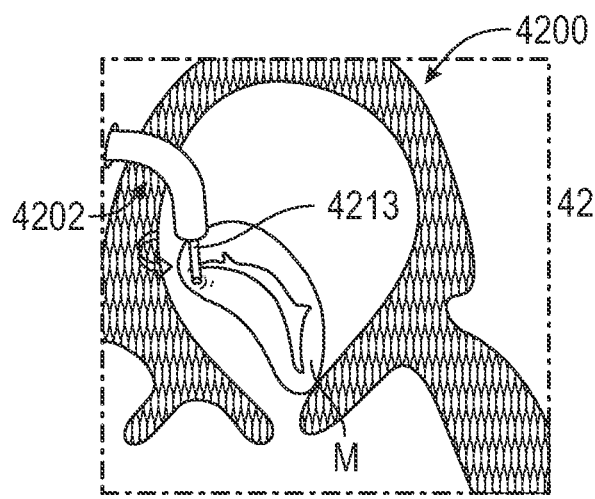
Figure 66D:
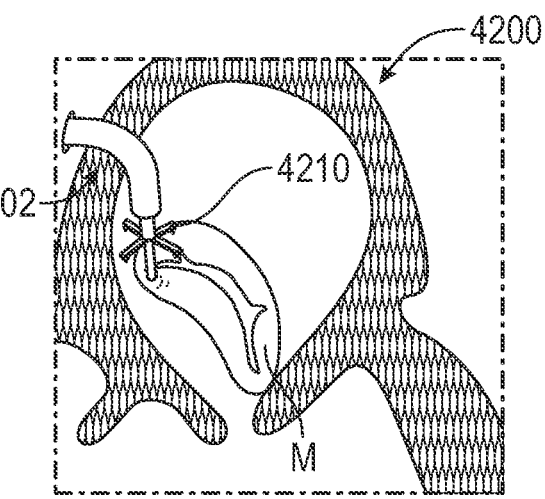

With reference to FIG. 66C, the contact member 4204 can thereafter be rotated by for example and without limitation, a rotation of a core member or other member 4213 of the delivery device 4202 so as to twist the tissue in the commissure and draw such tissue together to resize the mitral valve annulus. As with any of the other embodiments disclosed herein, in some embodiments used for treatment of the mitral valve, the contact member 4204 can be rotated by at least one-eighth or approximately one-eighth of a complete rotation (i.e., 45 degrees or approximately 45 degrees) relative to the first rotational position (which can be an initial position—i.e., an initial rotational position), by one-quarter or approximately one-quarter of a complete rotation (i.e., 90 degrees or approximately 90 degrees) relative to the first rotational position, or by at least one-half or approximately one-half of a complete rotation (i.e., 180 degrees or approximately 180 degrees) relative to the first rotational position, or wherein the second rotational position can be from one-eighth or approximately one-eighth of a complete rotation (i.e., 45 degrees or approximately 45 degrees) to one-half or approximately one-half of a complete rotation (i.e., 180 degrees or approximately 180 degrees) relative to the first rotational position. In any apparatus, implant device, method, or other embodiments disclosed herein, the second rotational position can be from one-quarter or approximately one-quarter of a complete rotation (i.e., 90 degrees or approximately 90 degrees) to one or more or approximately one or more complete rotations (i.e., 360 degrees or approximately 360 degrees or more) relative to the first rotational position, or from one-quarter or approximately one-quarter of a complete rotation (i.e., 90 degrees or approximately 90 degrees) to two, three, or more complete rotations or approximately one or more complete rotations (i.e., 360 degrees or approximately 360 degrees or more) relative to the first rotational position, one-eight or approximately one-eighth of a complete rotation (i.e., 45 degrees or approximately 45 degrees) to one, two, three, or more complete rotations or approximately one or more complete rotations (i.e., 360 degrees or approximately 360 degrees or more) relative to the first rotational position, or any value or ranges of values within any of the foregoing ranges. Note that the first rotational position and the second rotational position can be referred to the first position and second position, respectively, herein. In any embodiments disclosed herein, the twisting movement or step can be accomplished by a torque catheter.

Further, in any apparatus, implant device, or method embodiments disclosed herein, the catheter can be configured to exert a torque on the contact member 4204 and/or other component of the implant to rotate the contact member 4204 and/or other component of the implant from the first rotational position until a threshold predetermined torque level is reached, or until the user decides to stop the rotation, whichever comes first. In some embodiments, the threshold predetermined torque level can be from 0.25 in-oz of torque or approximately 0.25 in-oz of torque to 10 in-oz of torque or approximately 10 in-oz of torque, or from 0.5 in-oz of torque or approximately 0.5 in-oz of torque to 5 in-oz of torque or approximately 5 in-oz of torque.

Figure 66E:
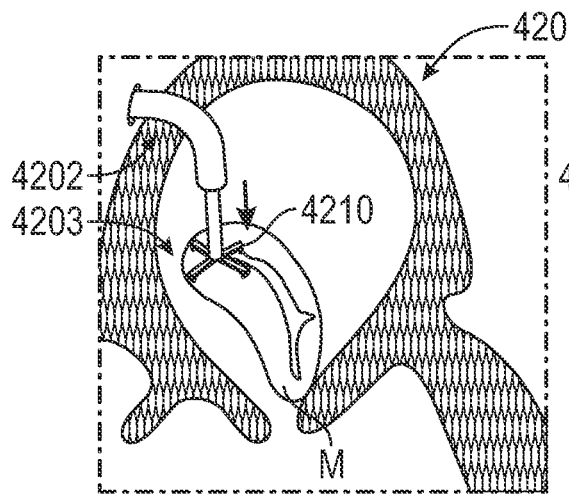
Figure 66F:
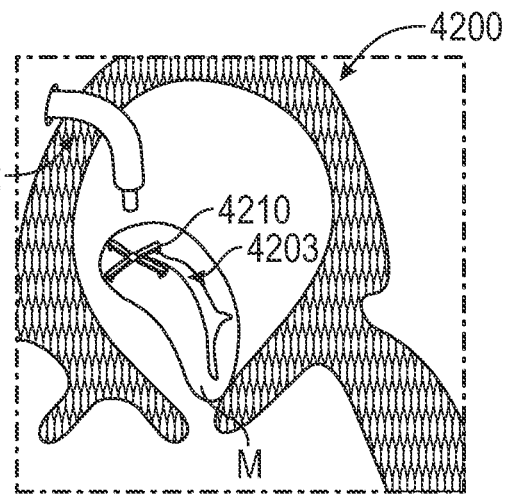
Figure 66G:
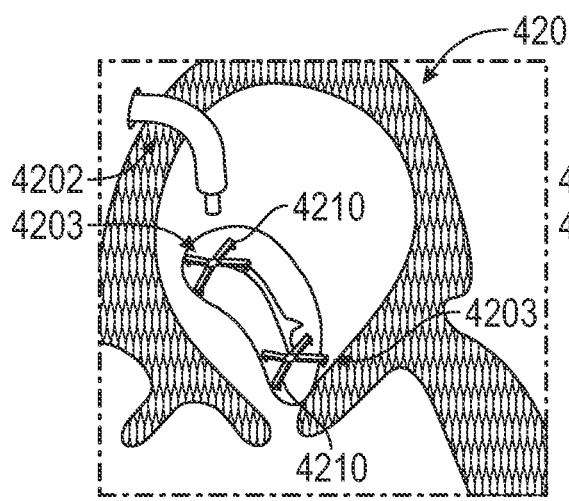

When a sufficient or desired degree of tissue closure, resizing, or reduction at the commissure has been achieved by the rotation of the contact member 4204, the tissue that has been drawn together can be secured using any desired or available techniques including, without limitation, sutures, staples, or other fasteners, or by deploying a securing element 4210 to cover and engage with the tissue that has been drawn together, for example and without limitation, as shown in FIGS. 66E-66F. After the tissue that has been drawn together is sufficiently secured, the delivery device 4202 can be disengaged from the implant member 4203 so that the implant member 4203 remains in position in the commissure of the mitral valve. In some embodiments, the contact member 4204 can be removed from the mitral valve before completion of the procedure. In some embodiments, a second implant 4203 can be deployed into the second commissure of the mitral valve, as needed or desired.

In any embodiments disclosed herein, a retaining member such as or similar to any of the other retaining members disclosed with respect to any of the other implant embodiments disclosed herein can be used to couple the securing element 4210 to the contact member 4204. In other embodiments, the securing element 4210 can be separate and/or independent from the contact member 4204. Additionally, in some embodiments, the retaining member can be used to bias the securing element 4210 toward the tissue surface and/or the contact member 4204, and/or be used to control the positioning or spacing between the securing element 4210 and the contact member 4204.

Figure 66H:
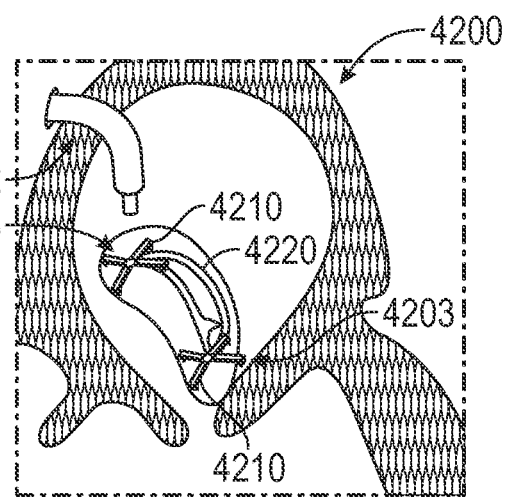

With reference to FIG. 66H, in some embodiments, the treatment system 4200 can be configured to implant a first implant device 4203 that can have a securing element 4210 in or adjacent to a first commissure and a second implant device 4203 that can have a securing element 4210 in or adjacent to a second commissure, and a bar or other connecting member 4220 coupled with the first and second implant devices 4203. The connecting member 4220 can be used to maintain a desired spacing between the first and second implant devices, be adjustable to draw one closer to the other thus applying additional tissue reduction 4203, or to push apart the implant devices, as mentioned above. In some embodiments, the connective member 4220 can have any desired shape, including a curved shape, and can be used to reshape the mitral valve. The connecting member could be used secure the rotational implants to their respective position and also hold them proximate to the mitral annulus. The connecting member could also be adjustable in length to move the rotational members toward or away from one another. As shown in FIG. 66H, in any embodiments, the connection member 4220 can be positioned such that it does not block blood flow through the valve but can be placed in-plane with the mitral valve on the posterior side (for example and without limitation, it can be positioned opposite the Aortic valve).

FIGS. 67A-67G illustrate another embodiment of a treatment system 4300 that can be used for weight loss surgery (for example, stomach reshaping/reducing) or another embodiment of a use of the other treatment system embodiments disclosed herein for weight loss surgery. Any embodiments of the treatment system 4300 or implant device 4303 can have any of the components, features, or other details of any other treatment system or implant device embodiments disclosed herein, including without limitation any of the embodiments of the treatment system 100, 200, 300, 400 or implant device 102, 202, 302, 402 described above, in any combination with any of the components, features, or details of the treatment system 4300 or implant device 4303 disclosed below. Similarly, any components, features, or other details of any of the other treatment system or implant device embodiments disclosed herein can have any of the components, features, or other details of any embodiments of the treatment system 4300 or implant device 4303 disclosed herein, in any combination, with any of the components, features, or details of the treatment system or implant device embodiments disclosed herein.

Figure 67A:
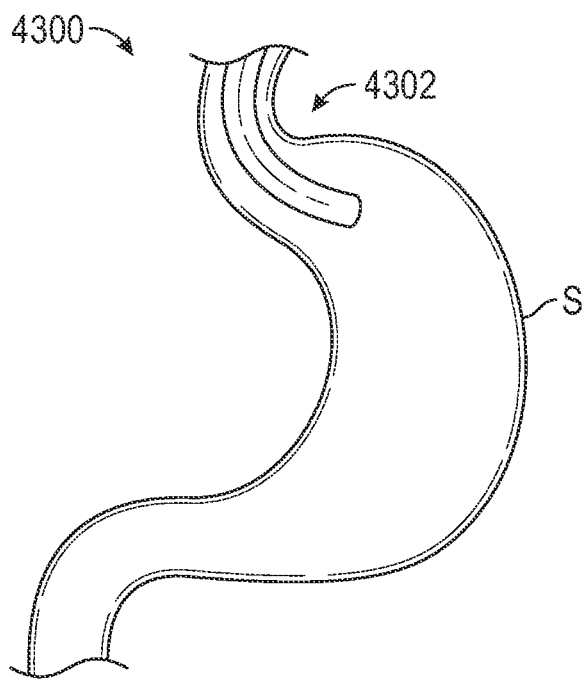
FIGS. 67A-67G show an embodiment of a device and an embodiment of a method for stomach resizing or reshaping.
Figure 67B:
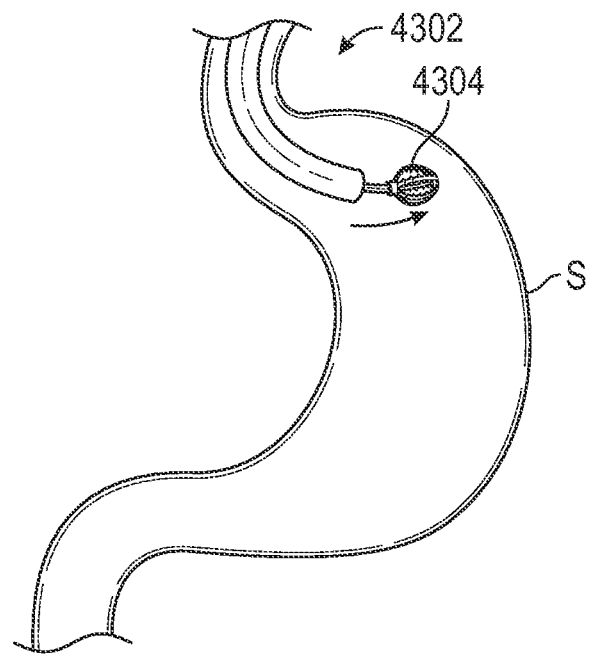
Figure 67C:
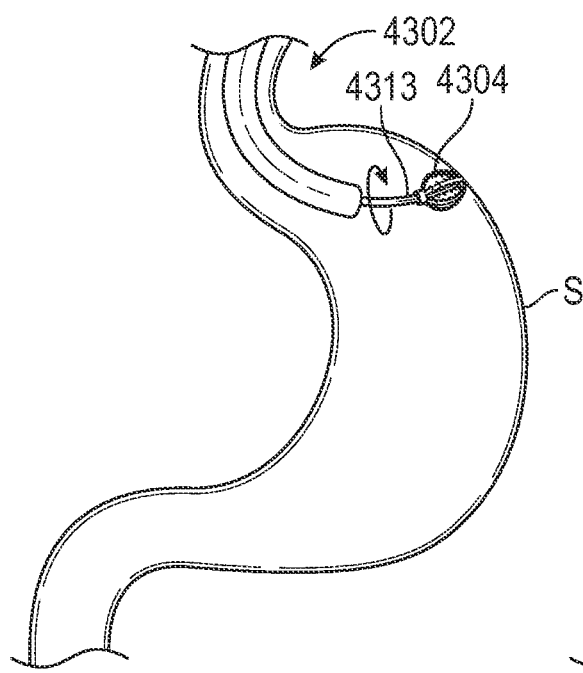
Figure 67D:
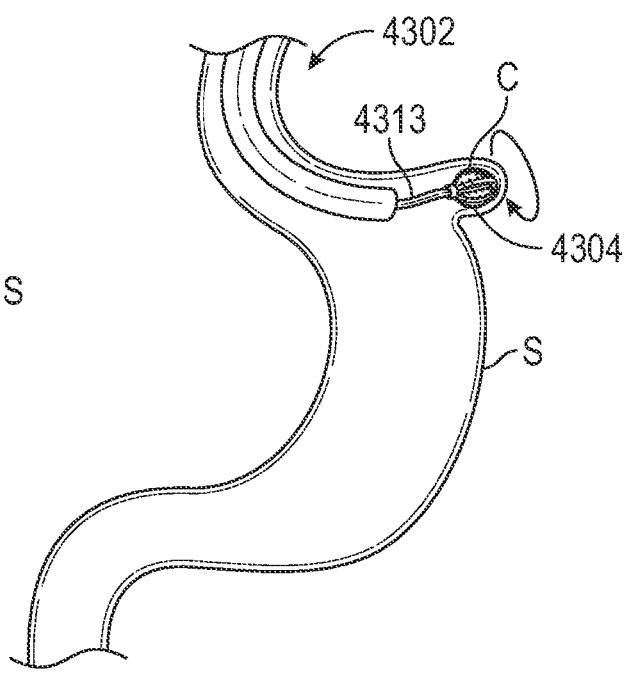

With reference to FIG. 67A-67B, the delivery device 4302 can be advanced through the patient's body toward the stomach S or other intestinal cavities (collectively referred to herein as the stomach). FIG. 67B shows the contact member 4304 being advanced toward a wall of the stomach so that at least an end portion of the contact member 4304 is placed in contact with the wall of the stomach. The contact member 4304 can be advanced further against the wall of the stomach so as to deflect the wall of the stomach and create a cavity C within the stomach S that can be closed by rotating the contact member 4304 and drawing the tissue of the stomach together so as to occlude or close the cavity C, as shown in FIG. 67D, similar to the other applications described herein. In some embodiments, the contact member 4304 can be rotated as it is being forced axially against the wall of the stomach. As shown in FIG. 67D as compared to FIG. 67C, creating and closing the cavities C can reduce the overall size and volume of the stomach S.

Figures 67E, 67F:
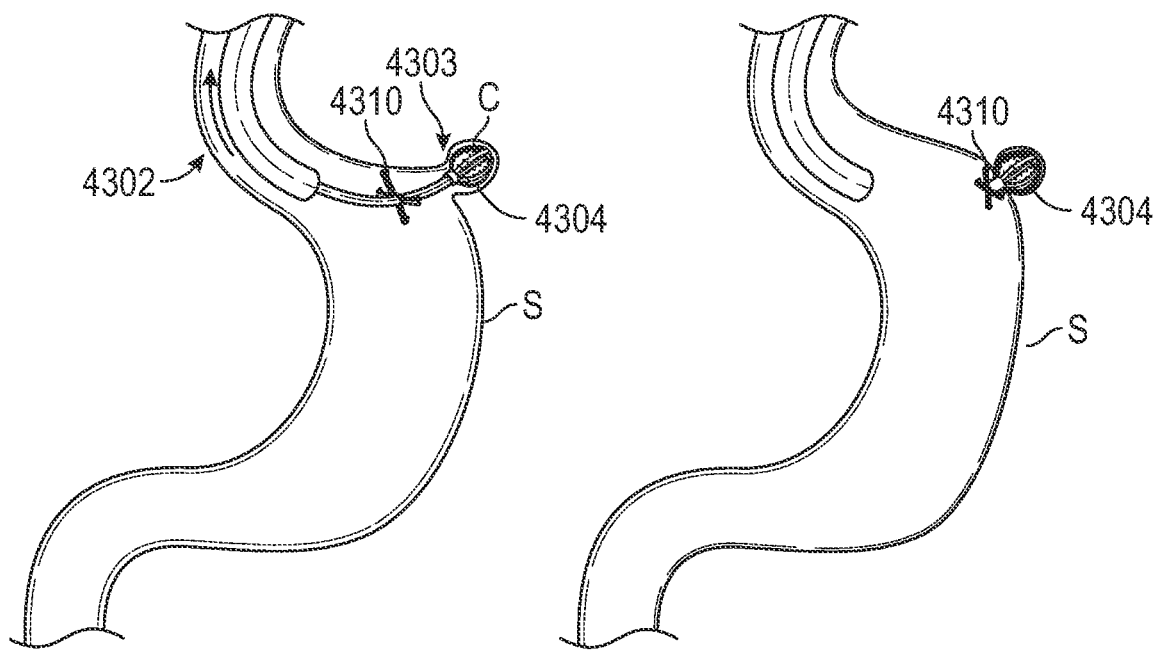
Figure 67G:
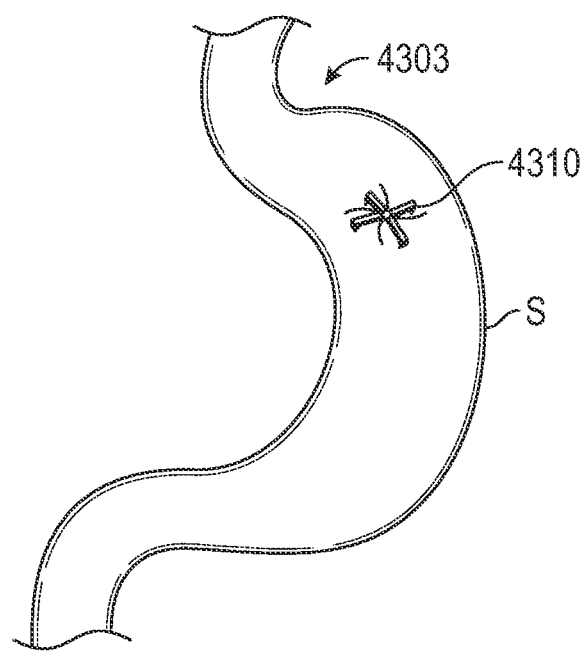

Thereafter, with reference to FIG. 67E, when the desired level of twisting and tissue gathering has been achieved, a securing element 4310 can be deployed from the delivery device 4302 to maintain the gathered tissue in the gathered state or second state and also to hold the cavity C that has been created in the second or gathered state. In other embodiments, sutures, staples, or other tissue fasteners or anchors can be used to hold the tissue in the gathered state. Once the tissue has been secured by the securing element 4310 or otherwise, the implant 4303 can be disengaged from the delivery device and the delivery device can be removed from the body, as shown in FIG. 67G. This procedure can be repeated multiple times to create multiple cavities to reduce the volume of the stomach as desired.

In any embodiments disclosed herein, a retaining member such as or similar to any of the other retaining members disclosed with respect to any of the other implant embodiments disclosed herein, can be used to couple the securing element 4310 to the contact member 4304. Additionally, in some embodiments, the retaining member can be used to bias the securing element 4310 toward the tissue surface and/or the contact member 4304, or be used to control the positioning or spacing between the securing element 4310 and the contact member 4304.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree. The ranges disclosed herein also encompass any and all overlap, sub-ranges, and combinations thereof, and any specific values within those ranges. Language such as "up to," "at least," "greater than," "less than," "between," and the like includes the number recited. Numbers and values used herein preceded by a term such as "about" or "approximately" include the recited numbers. For example, "approximately 7 mm" includes "7 mm" and numbers and ranges preceded by a term such as "about" or "approximately" should be interpreted as disclosing numbers and ranges with or without such a term in front of the number or value such that this application supports claiming the numbers, values and ranges disclosed in the specification and/or claims with or without the term such as "about" or "approximately" before such numbers, values or ranges such, for example, that "approximately two times to approximately five times" also includes the disclosure of the range of "two times to five times." The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A device for reshaping, closing, or occluding a cavity, comprising:
    an implant comprising:
        a contact member configured to move between a first state and a second state, the contact member including one or more anchor features, the contact member being positioned along a longitudinal axis;
        a retaining member; and
        a securing element coupled with the contact member via the retaining member;
    wherein:
        the contact member is configured to engage a wall portion of the cavity after the contact member has been advanced into the cavity;
        the contact member is configured to rotate at least in a first angular direction from a first position to a second position;
        the contact member is configured to twist at least a portion of the wall portion of the cavity in the first angular direction when the contact member is engaged with the wall portion of the cavity and is rotated from the first position to the second position to twist tissue of the wall portion of the cavity through engagement between the one or more anchor features and the tissue and thereby draw at least a first portion of the wall portion of the cavity toward a second portion of the wall portion of the cavity; and
        the securing element is configured to prevent a rotation of the wall portion of the cavity in a second angular direction when the securing element is implanted in an operable state, to thereby maintain the tissue in a twisted state, wherein the second angular direction is opposite to the first angular direction about the longitudinal axis.

2. The device of claim 1, wherein the contact member is self-expandable such that at least a portion of the contact member automatically expands from the first state to the second state when a restraint is removed from the contact member.

3. The device of claim 1, wherein the contact member is biased to remain in the second state after deployment into the cavity.

4. The device of claim 1, wherein the contact member is configured to be removable from the cavity after the securing element is implanted.

5. The device of claim 1, wherein the contact member is configured to be rotated in a clockwise or in a counter-clockwise direction, or configured to be rotated in a clockwise or in a counter-clockwise direction after the contact member has engaged with a wall portion of the cavity.

6. The device of claim 1, wherein the device is configured to cause a tissue of the cavity to constrict around an outer surface of a body portion of the device when the contact member is rotated to the second position, and the securing element configured to engage with the tissue of the cavity that has constricted around the outer surface of the body portion of the device or a tissue adjacent to the cavity to prevent rotation of the contact member and/or the tissue in the second angular direction.

7. The device of claim 6, wherein the securing element has a plurality of tissue anchors configured to engage with a portion of a tissue of the cavity that has constricted around the outer surface of the body portion of the device or a tissue adjacent to the cavity to prevent rotation of the contact member and/or the tissue in the second angular direction.

8. The device of claim 7, wherein the plurality of tissue anchors on the outside surface of the contact member are configured to engage an inner wall surface of the cavity after the contact member has been moved to the second state.

9. The device of claim 1, wherein the securing element has a helical shape and is configured to rotate about a body portion of the implant during implantation.

10. The device of claim 1, wherein the second position is from approximately one-quarter of a complete rotation to one or more complete rotations relative to the first position.

11. The device of claim 1, the retaining member being configured to bias the securing element toward the contact member.

12. The device of claim 1, wherein the retaining member comprises a threaded shaft.

13. The device of claim 1, wherein the contact member is configured to rotate at least in the first angular direction from the first position to the second position when a torque is applied to the contact member.

14. The device of claim 1, wherein the securing element is structurally configured such that only a portion of the securing element extends out of the cavity after deployment of the device, and all other portions of the device are internal to the cavity after deployment of the device.

15. The device of claim 1, wherein the device is structurally configured such that only approximately 10% or less of an overall length of the device extends out of the cavity after deployment of the device.

16. The device of claim 1, wherein at least a portion of the contact member is inflatable and deflatable.

17. The device of claim 1, wherein the contact member comprises a balloon.

18. The device of claim 1, wherein the securing element is removably coupleable with the contact member.

19. The device of claim 1, wherein the device is configured and operable to reshape, close, or occlude a cavity that comprises a wound or a wound cavity.

20. The device of claim 1, further comprising a catheter configured to advance the contact member into the cavity when the contact member is in the first state and to cause the contact member to move from the first state to the second state so that an outside surface of the contact member expands against an inner wall surface of the cavity after the contact member has been advanced into the cavity, wherein the catheter is configured to exert a torque on the contact member when at least a portion of the catheter is rotated until a predetermine torque level is reached to rotate the contact member from the first position to the second position so that the contact member twists at least a portion of the cavity.

21. A method of reshaping, closing, or occluding a cavity, comprising:
advancing a deployment device having the device for reshaping, closing, or occluding a cavity of claim 1 into the cavity;
moving the implant of the device for reshaping, closing, or occluding a cavity so as to move at least a portion of an outside surface of the implant or one or more tissue anchors extending away from an outer surface of the implant against an inner wall surface of the cavity;
rotating the contact member of the implant from a first position to a second position to twist the cavity; and
preventing the contact member from rotating back to the first position.

22. The method of claim 21, wherein the contact member is self-expanding and wherein moving the contact member from the first state to the second state comprises advancing the contact member out of a distal end of the deployment device.

23. The method of claim 21, comprising engaging a wall portion on an inside of the cavity with one or more tissue anchors positioned on an outside surface of the contact member.

24. The method of claim 21, wherein preventing the contact member from rotating back to the first position comprises engaging a tissue wall with an anchor element to prevent relative movement between the contact member and the tissue wall.

25. The method of claim 21, comprising rotating the contact member in a first direction from a first position to a second position by rotating a core member or other member of the device coupled with the contact member.

26. The method of claim 21, wherein the cavity is a space in a commissure of a mitral valve, and the method comprises reducing an annular diameter of the mitral valve or bringing a posterior leaflet closer to an anterior leaflet by reducing an annular space of the mitral valve.

27. The device of claim 1, wherein the device is configured and operable to reshape, close, or occlude a cavity that comprises an opening, a hole, a cut, a slit, a vessel, a passageway, a chamber, a heart chamber, or a tissue void within a patient.

28. The device of claim 1, wherein the device is configured and operable to reshape, close, or occlude a cavity that comprises a cavity of a stomach.

29. The device of claim 1, wherein the device is configured and operable to reshape, close, or occlude a cavity that comprises a mitral valve or commissure of the mitral valve.

30. The device of claim 1, wherein:
the device is configured and operable to reshape, close, or occlude a cavity that comprises a mitral valve or a commissure of the mitral valve;
the contact member is configured to rotate in at least the first direction from the first position to the second position to twist at least a portion of a tissue of the commissure of the mitral valve to draw the tissue in the commissure together to reduce a size of an annulus of the mitral valve.

31. The device of claim 30, further comprising a second implant comprising a second contact member and a second securing element coupled with the second contact member, wherein:
the second contact member is configured to rotate to twist at least a portion of a tissue of a second commissure of the mitral valve to draw the tissue in the second commissure together to reduce the size of the annulus of the mitral valve; and
the second securing element is configured to prevent a rotation of the wall portion of the tissue of the second commissure when the second securing element is implanted in an operable state.

32. A method of reshaping a cavity, wherein the cavity is a commissure of a mitral valve, comprising:
advancing the contact member of the device of claim 1 into the commissure of the mitral valve;
engaging at least a portion of a tissue of the commissure of the mitral valve with the contact member; and
rotating the contact member in a first direction from a first position to a second position to twist at least the portion of the tissue of the commissure of the mitral valve to draw the tissue of the commissure together to reduce a size of an annulus of the mitral valve.

33. A method of reshaping a cavity, wherein the cavity is a commissure of a heart valve, comprising:
advancing the contact member of the device of claim 1 into a first commissure of the heart valve;
engaging at least a portion of a tissue of the first commissure of the heart valve with the contact member;
rotating the contact member in a clockwise direction to twist at least the portion of the tissue of the first commissure of the heart valve to draw the tissue of the first commissure together to reduce a size of an annulus of the heart valve;
advancing a second contact member into a second commissure of the heart valve, the second;
engaging at least a portion of a tissue of the second commissure of the heart valve with the second contact member; and
rotating the second contact member in a counter-clockwise direction from a first position of the second contact member to a second position of the second contact member to twist at least the portion of the tissue of the second commissure of the heart valve to draw the tissue of the second commissure together to reduce a size of an annulus of the heart valve; and
preventing the second contact member from rotating back to the first position of the second contact member.

34. The method of claim 33, wherein preventing the contact member from rotating back to the first position of the contact member comprises engaging a tissue wall with an anchor element to prevent the contact member from rotating relative to the tissue wall.

35. A device for reshaping, closing, or occluding a cavity, comprising:
an implant comprising:
a contact member configured to move between a first state and a second state, the contact member having a shape selected from the group consisting of bulbous and spherical when in the second state, the contact member including one or more anchor features; and
a securing element coupled with the contact member;
wherein:
the contact member is configured to engage a wall portion of the cavity after the contact member has been advanced into the cavity;
the contact member is configured to rotate at least in a first angular direction from a first position to a second position;
the contact member is configured to twist at least a portion of the wall portion of the cavity in the first angular direction when the contact member is engaged with the wall portion of the cavity and is rotated from the first position to the second position to twist tissue of the wall portion of the cavity through engagement between the one or more anchor features and the tissue and thereby draw at least a first portion of the wall portion of the cavity toward a second portion of the wall portion of the cavity; and
the securing element is configured to prevent a rotation of the wall portion of the cavity in a second angular direction when the securing element is implanted in an operable state, to thereby maintain the tissue in a twisted state, wherein the second angular direction is opposite to the first angular direction.

36. A device for reshaping, closing, or occluding a cavity, comprising:
an implant comprising:
a contact member configured to move between a first state and a second state, the contact member including one or more anchor features, the contact member being positioned along a longitudinal axis; and
a securing element coupled with the contact member, the securing element being positioned along the longitudinal axis;
wherein:
the contact member is configured to engage a wall portion of the cavity after the contact member has been advanced into the cavity;
the contact member is configured to rotate at least in a first angular direction from a first position to a second position;
the contact member is configured to twist at least a portion of the wall portion of the cavity in the first angular direction when the contact member is engaged with the wall portion of the cavity and is rotated from the first position to the second position to twist tissue of the wall portion of the cavity through engagement between the one or more anchor features and the tissue and thereby draw at least a first portion of the wall portion of the cavity toward a second portion of the wall portion of the cavity; and
the securing element is configured to prevent a rotation of the wall portion of the cavity in a second angular direction when the securing element is implanted in an operable state, to thereby maintain the tissue in a twisted state, wherein the second angular direction is opposite to the first angular direction.

* * * * *